US011202851B2

(12) United States Patent
Zlotkin

(10) Patent No.: US 11,202,851 B2
(45) Date of Patent: *Dec. 21, 2021

(54) DISPERSION AND DETACHMENT OF CELL AGGREGATES

(71) Applicant: DISPERSEBIO LTD., Tel Aviv (IL)

(72) Inventor: Amir Zlotkin, Tel Aviv (IL)

(73) Assignee: DISPERSEBIO LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/645,941

(22) Filed: Jul. 10, 2017

(65) Prior Publication Data

US 2018/0153172 A1 Jun. 7, 2018

Related U.S. Application Data

(60) Continuation of application No. 14/950,951, filed on Nov. 24, 2015, now Pat. No. 9,700,058, which is a division of application No. 14/123,455, filed as application No. PCT/IB2012/001061 on May 31, 2012, now Pat. No. 9,284,351.

(60) Provisional application No. 61/491,756, filed on May 31, 2011.

(51) Int. Cl.

| *A01N 63/10* | (2020.01) |
|---|---|
| *A61L 27/22* | (2006.01) |
| *A61L 31/10* | (2006.01) |
| *A61L 31/16* | (2006.01) |
| *C07K 14/435* | (2006.01) |
| *C09D 5/16* | (2006.01) |
| *A61L 27/34* | (2006.01) |
| *A61L 27/54* | (2006.01) |
| *A61L 29/04* | (2006.01) |
| *A61L 29/08* | (2006.01) |
| *A61L 29/16* | (2006.01) |
| *A61L 31/04* | (2006.01) |
| *C07K 7/08* | (2006.01) |
| *C07K 14/47* | (2006.01) |
| *A61K 38/00* | (2006.01) |
| *A01N 63/50* | (2020.01) |

(52) U.S. Cl.
CPC ............ *A61L 27/227* (2013.01); *A01N 63/50* (2020.01); *A61L 27/34* (2013.01); *A61L 27/54* (2013.01); *A61L 29/048* (2013.01); *A61L 29/085* (2013.01); *A61L 29/16* (2013.01); *A61L 31/047* (2013.01); *A61L 31/10* (2013.01); *A61L 31/16* (2013.01); *C07K 7/08* (2013.01); *C07K 14/43595* (2013.01); *C07K 14/47* (2013.01); *C09D 5/1625* (2013.01); *C09D 5/1687* (2013.01); *A61K 38/00* (2013.01); *A61L 2300/252* (2013.01); *A61L 2300/404* (2013.01)

(58) Field of Classification Search
CPC ....... A01N 63/50; A61L 27/227; A61L 31/10; A61L 31/16; A61L 27/34; A61L 27/54; A61L 29/048; A61L 29/085; A61L 29/16; A61L 31/047; A61L 2300/252; A61L 2300/404; C07K 14/43595; C07K 7/08; C07K 14/47; C09D 5/1625; C09D 5/1687; A61K 38/00

See application file for complete search history.

(56) References Cited

U.S. PATENT DOCUMENTS

| 2002/0143149 | A1 | 10/2002 | Duckworth et al. |
|---|---|---|---|
| 2006/0269564 | A1 | 11/2006 | Emery et al. |
| 2007/0293422 | A1* | 12/2007 | Barbero ................ A61P 7/04 514/17.8 |
| 2010/0267638 | A1 | 10/2010 | Kalafatis |
| 2011/0070376 | A1 | 3/2011 | Wales et al. |

FOREIGN PATENT DOCUMENTS

| CN | 101213292 A | 7/2008 |
|---|---|---|
| CN | 101835668 A | 9/2010 |
| JP | 2008-528512 A | 7/2008 |
| WO | WO-96/11706 | 4/1996 |
| WO | WO-2006/079076 A2 | 7/2006 |
| WO | WO-2007/089272 A2 | 8/2007 |
| WO | WO-2009/154988 A2 | 12/2009 |
| WO | WO-2010/035107 A2 | 4/2010 |
| WO | WO-2010/076642 A1 | 7/2010 |
| WO | WO-2011/057336 A1 | 5/2011 |
| WO | WO-2012/164380 A2 | 12/2012 |

OTHER PUBLICATIONS

Blast search result of SEQ ID No. 6, from https://blast.ncbi.nlm.nih.gov/Blast.cgi, pp. 1-15, accessed Nov. 3, 2020.*
Blast search result of SEQ ID No. 8 in Barbero et al, from https://blast.ncbi.nlm.nih.gov/Blast.cgi, pp. 1-18, accessed Nov. 4, 2020.*
Blast search result of the cyclized unnamed protein product [Tetraodon nigroviridis] (CAG02807.1) in Zlotkin et al, from https://blast.ncbi.nlm.nih.gov/Blast.cgi, pp. 1-15, accessed Nov. 4, 2020.*
Blast search result of the cyclized hypothetical protein isoform 1 [Gallus gallus] (XP_001231839.1) in Zlotkin et al, from https://blast.ncbi.nlm.nih.gov/Blast.cgi, pp. 1-15, accessed Nov. 4, 2020.*
Namjoshi et al., "Cyclic Peptides as Potential Therapeutic Agents for Skin Disorders," Peptide Science, vol. 94, No. 5, 2010, pp. 673-680.
Aparna et al., Biofilms: Microbes and Disease, The Brazilian Journal of Infectious Diseases, 2008, 12, pp. 526-530.
Bjarnsholt, The role of bacterial biofilms in chronic infections, APMIS, 2013, 121 (Suppl. 136), pp. 1-51.

(Continued)

*Primary Examiner* — Li N Komatsu
(74) *Attorney, Agent, or Firm* — The Roy Gross Law Firm, LLC; Roy Gross

(57) ABSTRACT

Compositions comprising a protein or isolated peptide, and methods using the same for preventing, dispersing or detaching a biofilm, are disclosed.

14 Claims, 28 Drawing Sheets

Specification includes a Sequence Listing.

(56) References Cited

OTHER PUBLICATIONS

Carmen et al., "Treatment of biofilm infections on implants with low-frequency ultrasound and antibiotics," American Journal of Infectious Control, vol. 33, 2005, pp. 78-82.
Daep et al.; "Structural Characterization of Peptide-Mediated Inhibition of Porphyromonas gingivalis Biofilm Formation"; Infection and Immunity, 74(10): 5756-5762 (Oct. 2006).
Devemy et al.; "Identification of a novel dual E- and N-cadherin antagonist"; Peptides, 30(8): 1539-1547 (May 2009).
Echotoxin B2 [Monoplex echo], from http://www.ncbi.nlm.nih.gov/protein/290350685, p. 1, accessed Sep. 22, 2016.
European Patent Office examination report issued in application No. 12 732 869.8 dated Dec. 2, 2016.
F7IMU4, from http://www.uniprot.org/uniprot/F7IMU4, pp. 1-5, accessed Apr. 8, 2015.
Hall-Stoodley et al.; "Bacterial biofilms: From the natural environment to infectious diseases"; Nature Reviews, Microbiology, 2(2): 95-108 (Feb. 2004).
Hou et al.; "Effects of Trp- and Arg-Containing Antimicrobial-Peptide Structure on Inhibition of *Escherichia coli* Planktonic Growth and Biofilm Formation"; Applied and Environmental Microbiology, 76(6): 1967-1974 (Mar. 2010).
Johansson et al.; "Inhibition and Dispersion of Pseudomonas aeruginosa Biofilms by Glycopeptide Dendrimers Targeting the Fucose-Specific Lectin LecB"; Chemistry and Biology, 15(12): 1249-1257 (Dec. 2008).
Joo, Cyclic Peptides as Therapeutic Agents and Biochemical Tools, Biomol Ther, 2012, 20, pp. 19-26.
Kaplan; "Biofilm Dispersal: Mechanisms, Clinical Implications, and Potential Therapeutic Uses"; Journal of Dental Research, 89(3): 205-218 (Mar. 2010).
Medications A-Z List-A on MedicineNet, from http://www.medicinenet.com/medications/alpha_a.htm, pp. 1-12, accessed Apr. 8, 2015.
Overhage et al.; "Human Host Defense Peptide LL-37 Prevents Bacterial Biofilm Formation"; Infection and Immunity, 76(9): 4176-4182 (Sep. 2008).
Parsek et al., Bacterial Biofilms: An Emerging Link to Disease Pathogenesis, Annu. Rev. Microbiol., 2003, 57, pp. 677-701.
Tkacheva et al., New Actinoporins from Sea Anemone Heteractis crispa: Cloning and Functional Expresion, Biochemistry, vol. 76, 2011, pp. 1131-1139.
Wang et al.; "*Staphylococcus epidermidis* surfactant peptides promote biofilm maturation and dissemination of biofilm-associated infection in mice"; Journal of Clinical Investigation, 121(1): 238-248 (Jan. 2011).
O'Toole et al., "Biofilm Formation as Microbial Development," Annual Review of Microbiology, 2000, pp. 49-79 vol. 54, Annual Reviews.
Tang et al., "Formation and Regulatory Mechanism of Bacterial Biofilms" (Chinese), Journal of Biology (Chinese), 26(2): 48-50 and 53.

\* cited by examiner

*Pseudomonas aeruginosa adherence prevention by various peptides*

*Pseudomonas aeruginosa detachment by various peptides*

*Staphylococcus aureus adherence prevention by various peptides*

*Staphylococcus aureus detachment by various peptides*

*Candida albicans adherence prevention by various peptides*

*Candida albicans detachment by various peptides*

*Escherichia coli adherence prevention by various peptides*

*Escherichia coli detachment by various peptides*

2h starter $OD_{600}=0.16$, 2.5h biofilm with the peptide at 37°C

*Congo Red staining of Eqt2Z-Cyc incubated with Pseudomonas aeruginosa*

Bacteria + peptide incubation: 24h at $37^0C$

Buffer: TPM

Bacterial $OD_{600}$ at $T_0$: 0.27

Dye: Congo Red

Incubation with the dye: 30min at $25^0C$

Congo Red staining of grZ14s-nvCyc incubated with Pseudomonas aeruginosa

Bacteria + peptide incubation: 24h at 37$^0$C

Buffer: TPM

Bacterial $OD_{600}$ at $T_0$: 0.27

Dye: Congo Red

Incubation with the dye: 30min at 25$^0$C

Trypan Blue staining of grZ14s-nvCyc incubated with Pseudomonas aeruginosa

Bacteria + peptide incubation: 24h at $37^0$C

Buffer: TPM

Bacterial $OD_{600}$ at $T_0$: 0.27

Dye: Trypan Blue

Incubation with the dye: 30min at $25^0$C

*Congo Red staining of grZ14s-nvCyc incubated with Candida albicans*

Bacteria: *C. albicans* ATCC14053

Peptide: grZ14s-nvCyc

*C.a* incubation: 4hr at 37°C

Staining with Congo red

*Congo Red staining of Eqt2Z-Cyc incubated with Candida albicans*

Congo Red staining of grZ14s-nvCyc incubated with Staphylococcus aureus

Bacteria: *Staphylococcus aureus* ATCC25923

Peptide: grZ14s-nvCyc

Bacterial incubation: 4hr at $37^0C$

Staining with Congo red

SEQUENCE LISTING

```
<160> NUMBER OF SEQ ID NOS: 158

<210> SEQ ID NO 1
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (1)..(1)
<223> OTHER INFORMATION: /replace="Asn" or "Ile" or "Val" or "Arg" or
      "Lys" or "Gln" or "Leu"
<220> FEATURE:
<221> NAME/KEY: VARIANT
<222> LOCATION: (2)..(2)
<223> OTHER INFORMATION: /replace="Ile" or "Ala" or "Asn" or "Leu" or
      "Gln"
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: VARIANT
<222> LOCATION: (4)..(4)
<223> OTHER INFORMATION: /replace="Phe" or "Trp"
<220> FEATURE:
<221> NAME/KEY: VARIANT
<222> LOCATION: (5)..(5)
<223> OTHER INFORMATION: /replace="Asn" or "Gln" or "Glu"
<220> FEATURE:
<221> NAME/KEY: VARIANT
<222> LOCATION: (6)..(6)
<223> OTHER INFORMATION: /replace="Phe" or "Arg" or "Trp" or "Val" or
      "His" or "Leu" or "Lys" or "Ile"
<220> FEATURE:
<221> NAME/KEY: VARIANT
<222> LOCATION: (7)..(7)
<223> OTHER INFORMATION: /replace="Ser" or "Gly" or "Asp" or "His" or
      "Glu" or "Gln" or "Ile"
<220> FEATURE:
<221> NAME/KEY: VARIANT
<222> LOCATION: (8)..(8)
<223> OTHER INFORMATION: /replace="Leu" or "Phe" or "Met" or "Ser" or
      "Thr" or "Arg" or "Ala" or "Gly" or "Val" or "Pro" or "Tyr" or
      "Ile" or "Lys"
<220> FEATURE:
<221> NAME/KEY: VARIANT
<222> LOCATION: (9)..(9)
<223> OTHER INFORMATION: /replace="Asn" or "Phe" or "Lys" or "Leu" or
      "Arg" or "Ile" or "Val" or "Trp" or "Gln"
<220> FEATURE:
```

```
<221> NAME/KEY: VARIANT
<222> LOCATION: (10)..(10)
<223> OTHER INFORMATION: /replace="Lys" or "Asn" or "Thr" or "Glu" or
      "Arg" or "Leu" or "Gln" or "Ile" or "Val" or "Asp" or "Lys"
<220> FEATURE:
<221> NAME/KEY: VARIANT
<222> LOCATION: (11)..(11)
<223> OTHER INFORMATION: /replace="Glu" or "Asp" or "Gln" or "Ser" or
      "Ala" or "Ile"
<220> FEATURE:
<221> NAME/KEY: VARIANT
<222> LOCATION: (12)..(12)
<223> OTHER INFORMATION: /replace="Arg" or "Val" or "Leu" or "Ile" or
      "Lys" or "Phe" or "Glu"
<220> FEATURE:
<221> NAME/KEY: misc_feature
<222> LOCATION: (4)..(12)
<223> OTHER INFORMATION: /note="Residues given in the sequence have no
      preference with respect to those in the annotations for said
      positions"
<220> FEATURE:
<221> NAME/KEY: misc_feature
<222> LOCATION: (1)..(12)
<223> OTHER INFORMATION: /note="see specification as filed for detailed
      description of substitutions and preferred embodiments wherein the
      peptide is not 'SVPYDYNWYSNW'"

<400> SEQUENCE: 1

Ser Val Pro Tyr Asp Tyr Asn Trp Tyr Ser Asn Trp
1               5                   10

<210> SEQ ID NO 2
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Val Pro Tyr Asp Tyr Asn Trp Tyr Ser Asn Trp
1               5                   10

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (1)..(1)
<223> OTHER INFORMATION: /replace="Asn" or "Thr" or "Lys" or "Arg" or
      "His" or "Glu" or "Ile" or "Gln" or "Asp"
<220> FEATURE:
<221> NAME/KEY: VARIANT
<222> LOCATION: (2)..(2)
<223> OTHER INFORMATION: /replace="Ile" or "Leu" or "Tyr" or "Gly" or
      "Phe" or "Trp"
<220> FEATURE:
<221> NAME/KEY: VARIANT
<222> LOCATION: (3)..(3)
<223> OTHER INFORMATION: /replace="Asn" or "Gln" or "Glu" or "Asp" or
      "Ser"
<220> FEATURE:
<221> NAME/KEY: VARIANT
<222> LOCATION: (4)..(4)
<223> OTHER INFORMATION: /replace="Pro" or "Ala" or "Thr"
<220> FEATURE:
<221> NAME/KEY: VARIANT
<222> LOCATION: (5)..(5)
<223> OTHER INFORMATION: /replace="Trp" or "Tyr"
```

```
<220> FEATURE:
<221> NAME/KEY: VARIANT
<222> LOCATION: (6)..(6)
<223> OTHER INFORMATION: /replace="Asn" or "Glu" or "Gln"
<220> FEATURE:
<221> NAME/KEY: VARIANT
<222> LOCATION: (7)..(7)
<223> OTHER INFORMATION: /replace="Phe" or "Trp"
<220> FEATURE:
<221> NAME/KEY: VARIANT
<222> LOCATION: (8)..(8)
<223> OTHER INFORMATION: /replace="Gly" or "Glu"
<220> FEATURE:
<221> NAME/KEY: VARIANT
<222> LOCATION: (9)..(9)
<223> OTHER INFORMATION: /replace="Phe" or "Tyr"
<220> FEATURE:
<221> NAME/KEY: VARIANT
<222> LOCATION: (10)..(10)
<223> OTHER INFORMATION: /replace="Phe" or "Trp"
<220> FEATURE:
<221> NAME/KEY: VARIANT
<222> LOCATION: (11)..(11)
<223> OTHER INFORMATION: /replace="Gln"
<220> FEATURE:
<221> NAME/KEY: VARIANT
<222> LOCATION: (12)..(12)
<223> OTHER INFORMATION: /replace="Ile" or "Leu"
<220> FEATURE:
<221> NAME/KEY: misc_feature
<222> LOCATION: (1)..(12)
<223> OTHER INFORMATION: /note="Residues given in the sequence have no
      preference with respect to those in the annotations for said
      positions"
<220> FEATURE:
<221> NAME/KEY: misc_feature
<222> LOCATION: (1)..(12)
<223> OTHER INFORMATION: /note="see specification as filed for detailed
      description of substitutions and preferred embodiments wherein the
      peptide is not 'SVHSFDYDWYNV'"

<400> SEQUENCE: 3

Ser Val His Ser Phe Asp Tyr Asp Trp Tyr Asn Val
1               5                   10

<210> SEQ ID NO 4
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Val His Ser Phe Asp Tyr Asp Trp Tyr Asn Val
1               5                   10

<210> SEQ ID NO 5
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Val Pro Phe Asp Tyr Asn Leu Tyr Ser Asn Trp
1               5                   10

<210> SEQ ID NO 6
<211> LENGTH: 12
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ser Ala Pro Tyr Asn Phe Asn Phe Tyr Ser Asn Trp
1               5                   10

<210> SEQ ID NO 7
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Asn Ile Pro Phe Asn Phe Ser Leu Asn Lys Glu Arg
1               5                   10

<210> SEQ ID NO 8
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Val Pro Tyr Gln Tyr Asn Trp Tyr Ser Asn Trp
1               5                   10

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Val Pro Trp Glu Tyr Asn Phe Tyr Ser Asn Trp
1               5                   10

<210> SEQ ID NO 10
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Arg Ile Pro Tyr Asp Arg Gly Met Ile Val Asn Val
1               5                   10

<210> SEQ ID NO 11
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 11

Lys Val Pro Tyr Asp Trp Asp Ser Val Ile Asn Leu
1               5                   10

<210> SEQ ID NO 12
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Leu Pro Tyr Asp Val His Thr Tyr Asn Asp Trp
1               5                   10

<210> SEQ ID NO 13
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Leu Ala Pro Tyr Asp His Asn Arg Tyr Thr Gln Trp
1               5                   10

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Asn Pro Tyr Asp Leu Glu Ala Tyr Glu Asn Trp
1               5                   10

<210> SEQ ID NO 15
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Val Pro Tyr Asp Tyr Gln Gly Tyr Arg Asn Ile
1               5                   10

<210> SEQ ID NO 16
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16
```

```
Ser Val Pro Tyr Asp Tyr Asn Val Tyr Leu Asn Lys
1               5                   10

<210> SEQ ID NO 17
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ile Gln Pro Tyr Asp Lys Asn Tyr Phe Gln Asn Phe
1               5                   10

<210> SEQ ID NO 18
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Val Val Pro Tyr Asp Ile Asn Ile Lys Asp Asn Trp
1               5                   10

<210> SEQ ID NO 19
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Val Pro Tyr Asp Tyr Asn Pro Tyr Ser Asn Trp
1               5                   10

<210> SEQ ID NO 20
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Val Pro Tyr Asp Tyr Asn Lys Leu Lys Asn Trp
1               5                   10

<210> SEQ ID NO 21
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Val Pro Tyr Asp Tyr Asn Trp Arg Ser Ser Trp
1               5                   10
```

```
<210> SEQ ID NO 22
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Val Pro Tyr Asp Tyr Asn Trp Trp Ser Ala Trp
1               5                   10

<210> SEQ ID NO 23
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Val Pro Tyr Asp Tyr Asn Trp Gln Ser Asn Trp
1               5                   10

<210> SEQ ID NO 24
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Glu Leu Ser Ser Phe Asn Phe Asp Trp Tyr Asn Val
1               5                   10

<210> SEQ ID NO 25
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Arg Tyr Ser Ser Phe Asp Tyr Asp Trp Tyr Asn Val
1               5                   10

<210> SEQ ID NO 26
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asn Val His Ser Phe Asp Tyr Asp Trp Tyr Asn Val
1               5                   10

<210> SEQ ID NO 27
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Arg Val Glu Ser Phe Asn Tyr Asp Trp Tyr Asn Val
1               5                   10

<210> SEQ ID NO 28
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Arg Val Glu Ser Phe Asp Phe Asp Trp Tyr Asn Ile
1               5                   10

<210> SEQ ID NO 29
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Arg Ile Asn Ser Phe Asp Tyr Asp Trp Tyr Asn Val
1               5                   10

<210> SEQ ID NO 30
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Thr Val Asn Ser Phe Asp Tyr Asp Trp Tyr Asn Val
1               5                   10

<210> SEQ ID NO 31
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Lys Val Asn Ser Phe Asp Tyr Asp Trp Tyr Asn Val
1               5                   10

<210> SEQ ID NO 32
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 32

Thr Val His Ser Phe Asp Tyr Asp Trp Tyr Asn Val
1               5                   10

<210> SEQ ID NO 33
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Val His Ser Trp Asp Tyr Asp Trp Tyr Asn Val
1               5                   10

<210> SEQ ID NO 34
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ser Val His Ser Tyr Asp Phe Asp Trp Tyr Asn Val
1               5                   10

<210> SEQ ID NO 35
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Thr Leu Gln Ala Phe Asn Tyr Glu Trp Tyr Gln Leu
1               5                   10

<210> SEQ ID NO 36
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Lys Tyr Glu Thr Phe Glu Tyr Gly Trp Tyr Asn Ile
1               5                   10

<210> SEQ ID NO 37
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

His Gly Asp Ser Phe Gln Tyr Glu Trp Tyr Asn Leu
1               5                   10

<210> SEQ ID NO 38
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ser Val His Ser Phe Asp Trp Asp Trp Tyr Asn Val
1               5                   10

<210> SEQ ID NO 39
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ser Val His Ser Phe Asp Tyr Asp Tyr Tyr Asn Val
1               5                   10

<210> SEQ ID NO 40
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ser Val His Ser Phe Asp Tyr Asp Phe Tyr Asn Val
1               5                   10

<210> SEQ ID NO 41
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ser Val His Ser Phe Asp Tyr Asp Trp Phe Asn Val
1               5                   10

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Val His Ser Phe Asp Tyr Asp Trp Trp Asn Val
1               5                   10

```
<210> SEQ ID NO 43
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ile Phe Asn Pro Phe Asp Tyr Asp Trp Tyr Asn Val
1               5                   10

<210> SEQ ID NO 44
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gln Trp His Ser Phe Asp Tyr Asp Trp Tyr Asn Val
1               5                   10

<210> SEQ ID NO 45
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asp Val His Pro Phe Asp Tyr Asp Trp Tyr Asn Val
1               5                   10

<210> SEQ ID NO 46
<211> LENGTH: 6
<212> TYPE: PRT
<213> ORGANISM: Homo sapiens

<400> SEQUENCE: 46

Phe Asp Tyr Asp Trp Tyr
1               5

<210> SEQ ID NO 47
<211> LENGTH: 26
<212> TYPE: PRT
<213> ORGANISM: Ciona intestinalis

<400> SEQUENCE: 47

Ser Pro Leu Arg Cys Ser Glu Leu Ser Ser Phe Asn Phe Asp Trp Tyr
1               5                   10                  15

Asn Val Ser Asp Gln Ala Asp Leu Val Asn
            20                  25

<210> SEQ ID NO 48
<211> LENGTH: 6
<212> TYPE: PRT
<213> ORGANISM: Ciona intestinalis

<400> SEQUENCE: 48

Phe Asn Phe Asp Trp Tyr
1               5
```

```
<210> SEQ ID NO 49
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Tyr Asp Tyr Asn Trp Tyr
1               5

<210> SEQ ID NO 50
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Tyr Asp Tyr Asn Leu Tyr
1               5

<210> SEQ ID NO 51
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Phe Asp Tyr Asn Phe Tyr
1               5

<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Phe Asp Tyr Asn Leu Tyr
1               5

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Trp Asp Tyr Asn Leu Tyr
1               5

<210> SEQ ID NO 54
<211> LENGTH: 6
```

```
-continued

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Phe Asp Tyr Asn Trp Tyr
1               5

<210> SEQ ID NO 55
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Tyr Asp Trp Asn Leu Tyr
1               5

<210> SEQ ID NO 56
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Tyr Asp Trp His Leu Tyr
1               5

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Tyr Asp Tyr Ser Phe Tyr
1               5

<210> SEQ ID NO 58
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Leu Phe Ser Val Pro Tyr Asp Tyr Asn Trp Tyr Ser Asn Trp Trp
1               5                   10                  15

<210> SEQ ID NO 59
<211> LENGTH: 15
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 59

Leu Phe Ser Val Pro Tyr Asp Tyr Asn Trp Tyr Ser Asn Trp Trp
1               5                   10                  15

<210> SEQ ID NO 60
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Phe Ser Val Pro Tyr Asp Tyr Asn Leu Tyr Ser Asn Trp Trp
1               5                   10

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Met Phe Ser Val Pro Tyr Asp Tyr Asn Leu Tyr Ser Asn Trp Val
1               5                   10                  15

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Met Phe Ser Val Pro Phe Asp Tyr Asn Phe Tyr Ser Asn Trp Trp
1               5                   10                  15

<210> SEQ ID NO 63
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Leu Phe Ser Val Pro Phe Asp Tyr Asn Phe Tyr Ser Asn Trp Trp
1               5                   10                  15

<210> SEQ ID NO 64
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64
```

Met Phe Ser Val Pro Phe Asp Tyr Asn Leu Tyr Ser Asn Trp Trp
1               5                   10                  15

<210> SEQ ID NO 65
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Met Phe Ser Val Pro Phe Asp Tyr Asn Leu Tyr Thr Asn Trp Trp
1               5                   10                  15

<210> SEQ ID NO 66
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Met Trp Ser Val Pro Phe Asp Tyr Asn Leu Tyr Ser Asn Trp Trp
1               5                   10                  15

<210> SEQ ID NO 67
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Met Phe Ser Val Pro Phe Asp Tyr Asn Leu Tyr Lys Asn Trp Leu
1               5                   10                  15

<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Leu Phe Ser Val Pro Phe Asp Tyr Asn Leu Tyr Ser Asn Trp Trp
1               5                   10                  15

<210> SEQ ID NO 69
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Leu Phe Ser Ile Pro Phe Asp Tyr Asn Leu Tyr Ser Asn Trp Trp
1               5                   10                  15

```
<210> SEQ ID NO 70
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Met Phe Ser Val Pro Trp Asp Tyr Asn Leu Tyr Lys Asn Trp Leu
1               5                   10                  15

<210> SEQ ID NO 71
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Met Phe Ser Val Pro Trp Asp Tyr Asn Leu Tyr Lys Asn Trp Phe
1               5                   10                  15

<210> SEQ ID NO 72
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Met Phe Ser Val Pro Phe Phe Asp Tyr Asn Trp Tyr Ser Asn Trp Trp
1               5                   10                  15

<210> SEQ ID NO 73
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Met Ala Ser Ile Pro Tyr Asp Trp Asn Leu Tyr Gln Ser Trp Ala
1               5                   10                  15

<210> SEQ ID NO 74
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Met Ala Ser Ile Pro Tyr Asp Trp Asn Leu Tyr Ser Ala Trp Ala
1               5                   10                  15

<210> SEQ ID NO 75
<211> LENGTH: 15
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Met Ala Ser Ile Pro Tyr Asp Trp His Leu Tyr Asn Ala Trp Ala
1               5                   10                  15

<210> SEQ ID NO 76
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Phe Asp Phe Asp Trp Tyr
1               5

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ser Phe Asp Tyr Asp Trp Tyr
1               5

<210> SEQ ID NO 78
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Ser Phe Asp Tyr Asp Trp Tyr Asn
1               5

<210> SEQ ID NO 79
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

His Ser Phe Asp Tyr Asp Trp Tyr Asn
1               5

<210> SEQ ID NO 80
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 80

His Ser Phe Asp Tyr Asp Trp Tyr Asn Val
1               5                   10

<210> SEQ ID NO 81
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Val His Ser Phe Asp Tyr Asp Trp Tyr Asn Val
1               5                   10

<210> SEQ ID NO 82
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Val His Ser Phe Asp Tyr Asp Trp Tyr Asn Val Ser
1               5                   10

<210> SEQ ID NO 83
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ser Val His Ser Phe Asp Tyr Asp Trp Tyr Asn Val Ser
1               5                   10

<210> SEQ ID NO 84
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ser Val His Ser Phe Asp Tyr Asp Trp Tyr Asn Val Ser Asp
1               5                   10

<210> SEQ ID NO 85
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

```
Lys Ser Val His Ser Phe Asp Tyr Asp Trp Tyr Asn Val Ser Asp
1               5                   10                  15
```

<210> SEQ ID NO 86
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

```
Lys Ser Val His Ser Phe Asp Tyr Asp Trp Tyr Asn Val Ser Asp Gln
1               5                   10                  15
```

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

```
Asn Lys Ser Val His Ser Phe Asp Tyr Asp Trp Tyr Asn Val Ser Asp
1               5                   10                  15

Gln
```

<210> SEQ ID NO 88
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

```
Asn Lys Ser Val His Ser Phe Asp Tyr Asp Trp Tyr Asn Val Ser Asp
1               5                   10                  15

Gln Ala
```

<210> SEQ ID NO 89
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

```
Gln Asn Lys Ser Val His Ser Phe Asp Tyr Asp Trp Tyr Asn Val Ser
1               5                   10                  15

Asp Gln Ala
```

<210> SEQ ID NO 90
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 90

Gln Asn Lys Ser Val His Ser Phe Asp Tyr Asp Trp Tyr Asn Val Ser
1               5                   10                  15

Asp Gln Ala Asp
            20

<210> SEQ ID NO 91
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ser Gln Asn Lys Ser Val His Ser Phe Asp Tyr Asp Trp Tyr Asn Val
1               5                   10                  15

Ser Asp Gln Ala Asp
            20

<210> SEQ ID NO 92
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ser Gln Asn Lys Ser Val His Ser Phe Asp Tyr Asp Trp Tyr Asn Val
1               5                   10                  15

Ser Asp Gln Ala Asp Leu
            20

<210> SEQ ID NO 93
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Phe Ser Gln Asn Lys Ser Val His Ser Phe Asp Tyr Asp Trp Tyr Asn
1               5                   10                  15

Val Ser Asp Gln Ala Asp Leu
            20

<210> SEQ ID NO 94
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Phe Ser Gln Asn Lys Ser Val His Ser Phe Asp Tyr Asp Trp Tyr Asn
1               5                   10                  15

Val Ser Asp Gln Ala Asp Leu Lys
            20
```

<210> SEQ ID NO 95
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ser Phe Ser Gln Asn Lys Ser Val His Ser Phe Asp Tyr Asp Trp Tyr
1               5                   10                  15

Asn Val Ser Asp Gln Ala Asp Leu Lys
            20                  25

<210> SEQ ID NO 96
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ser Phe Ser Gln Asn Lys Ser Val His Ser Phe Asp Tyr Asp Trp Tyr
1               5                   10                  15

Asn Val Ser Asp Gln Ala Asp Leu Lys Asn
            20                  25

<210> SEQ ID NO 97
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Cys Ser Phe Ser Gln Asn Lys Ser Val His Ser Phe Asp Tyr Asp Trp
1               5                   10                  15

Tyr Asn Val Ser Asp Gln Ala Asp Leu Lys Asn
            20                  25

<210> SEQ ID NO 98
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Cys Ser Phe Ser Gln Asn Lys Ser Val His Ser Phe Asp Tyr Asp Trp
1               5                   10                  15

Tyr Asn Val Ser Asp Gln Ala Asp Leu Lys Asn Cys
            20                  25

<210> SEQ ID NO 99
<211> LENGTH: 214
<212> TYPE: PRT
<213> ORGANISM: Actinia equina -continued

<400> SEQUENCE: 99

```
Met Ser Arg Leu Ile Ile Val Phe Ile Val Thr Met Ile Cys Ser
1               5                   10                  15

Ala Thr Ala Leu Pro Ser Lys Lys Ile Ile Asp Glu Asp Glu Asp
            20                  25                  30

Glu Lys Arg Ser Ala Asp Val Ala Gly Ala Val Ile Asp Gly Ala Ser
        35                  40                  45

Leu Ser Phe Asp Ile Leu Lys Thr Val Leu Glu Ala Leu Gly Asn Val
    50                  55                  60

Lys Arg Lys Ile Ala Val Gly Val Asp Asn Glu Ser Gly Lys Thr Trp
65                  70                  75                  80

Thr Ala Leu Asn Thr Tyr Phe Arg Ser Gly Thr Ser Asp Ile Val Leu
                85                  90                  95

Pro His Lys Val Pro His Gly Lys Ala Leu Leu Tyr Asn Gly Gln Lys
            100                 105                 110

Asp Arg Gly Pro Val Ala Thr Gly Ala Val Gly Val Leu Ala Tyr Leu
        115                 120                 125

Met Ser Asp Gly Asn Thr Leu Ala Val Leu Phe Ser Val Pro Tyr Asp
130                 135                 140

Tyr Asn Trp Tyr Ser Asn Trp Trp Asn Val Arg Ile Tyr Lys Gly Lys
145                 150                 155                 160

Arg Arg Ala Asp Gln Arg Met Tyr Glu Glu Leu Tyr Tyr Asn Leu Ser
                165                 170                 175

Pro Phe Arg Gly Asp Asn Gly Trp His Thr Arg Asn Leu Gly Tyr Gly
            180                 185                 190

Leu Lys Ser Arg Gly Phe Met Asn Ser Ser Gly His Ala Ile Leu Glu
        195                 200                 205

Ile His Val Ser Lys Ala
210
```

<210> SEQ ID NO 100
<211> LENGTH: 175
<212> TYPE: PRT
<213> ORGANISM: Stichodactyla helianthus

<400> SEQUENCE: 100

```
Ala Leu Ala Gly Thr Ile Ile Ala Gly Ala Ser Leu Thr Phe Gln Val
1               5                   10                  15

Leu Asp Lys Val Leu Glu Glu Leu Gly Lys Val Ser Arg Lys Ile Ala
            20                  25                  30

Val Gly Ile Asp Asn Glu Ser Gly Gly Thr Trp Thr Ala Leu Asn Ala
        35                  40                  45

Tyr Phe Arg Ser Gly Thr Thr Asp Val Ile Leu Pro Glu Phe Val Pro
    50                  55                  60

Asn Thr Lys Ala Leu Leu Tyr Ser Gly Arg Lys Asp Thr Gly Pro Val
65                  70                  75                  80

Ala Thr Gly Ala Val Ala Ala Phe Ala Tyr Tyr Met Ser Ser Gly Asn
                85                  90                  95

Thr Leu Gly Val Met Phe Ser Val Pro Phe Asp Tyr Asn Trp Tyr Ser
            100                 105                 110

Asn Trp Trp Asp Val Lys Ile Tyr Ser Gly Lys Arg Arg Ala Asp Gln
        115                 120                 125

Gly Met Tyr Glu Asp Leu Tyr Tyr Gly Asn Pro Tyr Arg Gly Asp Asn
        130                 135                 140
```

Gly Trp His Glu Lys Asn Leu Gly Tyr Gly Leu Arg Met Lys Gly Ile
145                 150                 155                 160

Met Thr Ser Ala Gly Glu Ala Lys Met Gln Ile Lys Ile Ser Arg
            165                 170                 175

<210> SEQ ID NO 101
<211> LENGTH: 184
<212> TYPE: PRT
<213> ORGANISM: Danio rerio

<400> SEQUENCE: 101

Met Thr Glu Ser Ala Glu Ala Val Ala Ala Asn Val Ser Ser Arg Arg
1               5                   10                  15

His Ala Thr Val Glu Ile Thr Asn Leu Thr Asn Asn Tyr Cys Phe Leu
            20                  25                  30

Asn Pro Lys Val Tyr Leu Glu Asn Gly Glu Thr Ser Asn Pro Pro Gln
        35                  40                  45

Pro Thr Val Arg Pro Leu Lys Thr Glu Val Cys Thr Phe Ser Lys Ser
    50                  55                  60

Ala Ala His Ala Thr Gly Ser Val Gly Val Leu Thr Tyr Asp Leu Phe
65                  70                  75                  80

Glu Arg Arg Arg Asn Asp Tyr Thr Glu Thr Leu Ala Ile Met Phe Ser
                85                  90                  95

Val Pro Trp Asp Tyr Asn Leu Tyr Lys Asn Trp Phe Ala Val Gly Ile
            100                 105                 110

Tyr Pro Lys Gly Lys Glu Cys Asp Gln Ala Leu Tyr Lys Glu Met Tyr
        115                 120                 125

Tyr Gln Lys Asn Gln His Gly Phe Val Arg Glu Glu Ala Asn Gly Ser
    130                 135                 140

Gly Ile Asn Phe Glu Gly Lys Asn Leu Asp Ile Arg Ala Thr Met Cys
145                 150                 155                 160

Pro Met Gly Arg Ala Ile Val Lys Val Glu Val Trp Asp Lys Leu Leu
                165                 170                 175

Ser Pro Met Ala Gln Met Asp Cys
            180

<210> SEQ ID NO 102
<211> LENGTH: 181
<212> TYPE: PRT
<213> ORGANISM: Tetradodon nigroviridis

<400> SEQUENCE: 102

Met Glu Ser Ala Glu Ala Val Ala Asp Val Ser Arg Ser Arg Ser
1               5                   10                  15

Val Thr Ile Glu Ile Ser Asn Leu Thr Lys Asn Tyr Cys Leu Ile Asn
            20                  25                  30

Pro Arg Val Tyr Leu Glu Ser Gly Glu Thr Tyr Asn Pro Pro Gln Pro
        35                  40                  45

Thr Val Arg Pro Leu Met Thr Glu Val Cys Thr Phe Ser Lys Ser Ser
    50                  55                  60

Gly Ile Pro Thr Gly Ser Val Gly Val Leu Thr Tyr Glu Leu Leu Glu
65                  70                  75                  80

Arg Arg Ser Thr Met Leu Pro Glu Thr Leu Ala Ile Met Phe Ser Val
                85                  90                  95

Pro Tyr Asp Tyr Ser Phe Tyr Asn Asn Trp Phe Ala Val Gly Ile Tyr
            100                 105                 110

```
Glu Thr Gly Thr Lys Cys Asn Glu Gly Leu Tyr Lys Gln Met Tyr Asn
            115                 120                 125

Glu Lys Lys Gln Ala Glu His Gly Phe Val Arg Glu Lys Ala Asn Gly
        130                 135                 140

Ser Gly Ile Asn Tyr Val Gly Gly Asn Leu Asp Ile Arg Ala Thr Met
145                 150                 155                 160

Asn Pro Leu Gly Lys Ala Ile Met Lys Val Glu Val Trp Asp Ala Phe
                165                 170                 175

Phe Pro Phe Ser Glu
            180

<210> SEQ ID NO 103
<211> LENGTH: 199
<212> TYPE: PRT
<213> ORGANISM: Physcomitrella patens

<400> SEQUENCE: 103

Met Val Val His Leu Ile Ala Met Gly Leu Arg Tyr Ser Glu Thr Ile
1               5                   10                  15

Met Lys Thr Ala Arg Met Ala Glu Ala Ile Pro Ala Ala Glu Leu
            20                  25                  30

Ser Ile Lys Thr Leu Gln Asn Ile Val Glu Gly Ile Thr Gly Val Asp
            35                  40                  45

Arg Lys Ile Ala Ile Gly Phe Lys Asn Leu Thr Asp Tyr Thr Leu Glu
    50                  55                  60

Asn Leu Gly Val Tyr Phe Asn Ser Gly Ser Ser Asp Arg Ser Ile Ala
65                  70                  75                  80

Tyr Lys Ile Asn Ala Gln Glu Ala Leu Leu Phe Ser Ala Arg Lys Ser
                85                  90                  95

Asp His Thr Ala Arg Gly Thr Val Gly Thr Phe Ser Tyr Tyr Ile Gln
            100                 105                 110

Asp Glu Asp Lys Thr Val His Val Met Trp Ser Val Pro Phe Asp Tyr
            115                 120                 125

Asn Leu Tyr Ser Asn Trp Trp Asn Ile Ala Val Val Asp Gly Arg Gln
        130                 135                 140

Pro Pro Asp Ser Asn Val His Asp Asn Leu Tyr Asn Gly Ser Gly Gly
145                 150                 155                 160

Met Pro Tyr Pro Asn Lys Pro Asp Gln Tyr Ile Asn Asn Glu Gln Lys
                165                 170                 175

Gly Phe His Leu Phe Gly Ser Met Thr Asn Asn Gly Gln Ala Thr Ile
            180                 185                 190

Glu Val Glu Leu Lys Lys Ala
        195

<210> SEQ ID NO 104
<211> LENGTH: 204
<212> TYPE: PRT
<213> ORGANISM: Gallus gallus

<400> SEQUENCE: 104

Met Pro Pro Lys Glu Lys Lys Glu Asn Asp Lys Pro Cys Asn Asp Asn
1               5                   10                  15

Cys Gln Pro Lys Pro Gln Gly Lys Gly Val Glu Ser Leu Met Lys Asn
            20                  25                  30

Ile Asp Val Cys Arg Ser Val Gly Leu Glu Ile Ile Asn Arg Thr Arg
            35                  40                  45
```

```
Thr Val Thr Leu Thr Asp Phe Arg Ser Tyr Cys Phe Ser Gly Lys Ile
    50                  55                  60

Val Thr Thr Leu Pro Phe Glu Ile Gly Pro Asp Ser Lys Gly Ile Cys
 65                  70                  75                  80

Ile Phe Ala Lys Thr Pro Tyr Ser Leu Arg Gly Ser Val Gly Thr Val
                 85                  90                  95

Val Cys Lys Ala Asp Thr Phe Phe Leu Ala Ile Thr Phe Ser Asn Pro
                100                 105                 110

Tyr Asp Tyr Ile Leu Tyr Lys Ile Glu Phe Ala Leu Glu Ile Phe Thr
                115                 120                 125

Glu Pro Asn His Leu Gly Asn Leu Gly Asp Val Phe Ser Lys Met Met
130                 135                 140

Lys Ser Lys Pro Tyr Cys Gly Ser Ser Leu Phe Gln Arg Ala Val Leu
145                 150                 155                 160

Glu Ser Glu His Glu Thr Leu Glu Val Ser Lys Gly Ser Ile Arg Val
                165                 170                 175

Gln Ala Lys Met Ser Asn Asn Arg Lys Ala Ile Leu Lys Val Gln Val
                180                 185                 190

Glu Asp Met Asp Pro Pro Pro Tyr Ser Lys Gly Met
                195                 200

<210> SEQ ID NO 105
<211> LENGTH: 384
<212> TYPE: PRT
<213> ORGANISM: Ornithorhynchus anatinus

<400> SEQUENCE: 105

Met Glu Gly Ser Pro Pro Gly Arg Pro Pro Gly Asn Asp Ser Leu Pro
  1               5                  10                  15

Pro Thr Leu Ser Pro Ala Val Pro Pro Tyr Val Lys Leu Gly Leu Thr
                 20                  25                  30

Ser Val Tyr Thr Ala Phe Tyr Ser Leu Leu Phe Val Phe Val Tyr Ala
                 35                  40                  45

Gln Leu Trp Leu Val Leu His His Arg His Arg Arg Leu Ser Tyr Gln
    50                  55                  60

Thr Val Phe Leu Phe Leu Cys Leu Leu Trp Ala Ala Leu Arg Thr Val
 65                  70                  75                  80

Leu Phe Ser Phe Tyr Phe Arg Asp Phe Leu Ala Ala Asn Lys Leu Gly
                 85                  90                  95

Pro Phe Gly Phe Trp Leu Leu Tyr Cys Cys Pro Val Cys Leu Gln Phe
                100                 105                 110

Phe Thr Leu Thr Leu Met Asn Leu Tyr Phe Ser Gln Val Ile Phe Lys
                115                 120                 125

Ala Lys Ser Lys Phe Ser Pro Glu Leu Leu Lys Tyr Arg Leu Ala Leu
130                 135                 140

Tyr Leu Ala Ser Leu Val Val Ser Leu Val Phe Leu Leu Val Asn Leu
145                 150                 155                 160

Thr Cys Ala Val Leu Val Lys Thr Gly Thr Trp Glu Arg Lys Val Val
                165                 170                 175

Val Ser Val Arg Val Ala Ile Asn Asp Thr Leu Phe Val Leu Cys Ala
                180                 185                 190

Val Ser Leu Ser Val Cys Leu Tyr Lys Ile Ser Lys Met Ser Leu Ala
                195                 200                 205

Asn Ile Tyr Leu Glu Ser Lys Gly Ser Ser Val Cys Gln Val Thr Ala
210                 215                 220
```

```
Ile Gly Val Thr Val Ile Leu Leu Tyr Ala Ser Arg Ala Cys Tyr Asn
225                 230                 235                 240

Leu Phe Thr Leu Ser Phe Ser Arg His Gly Ser Ser Phe Asp Tyr Asp
                245                 250                 255

Trp Tyr Asn Val Ser Asp Gln Ala Asp Leu Lys Ser Gln Leu Gly Asp
            260                 265                 270

Ala Gly Tyr Val Val Phe Gly Val Leu Phe Val Trp Glu Leu Leu
        275                 280                 285

Pro Thr Ser Leu Val Val Tyr Phe Phe Arg Val Arg Asn Pro Thr Lys
    290                 295                 300

Asp Pro Thr Asn Pro Arg Gly Val Pro Ser His Ala Phe Ser Pro Arg
305                 310                 315                 320

Ser Tyr Phe Phe Asp Asn Pro Arg Arg Tyr Asp Ser Asp Asp Asp Leu
                325                 330                 335

Ala Trp Asn Val Ala Pro Gln Gly Phe Gln Gly Ser Phe Ala Pro Asp
            340                 345                 350

Tyr Tyr Asp Trp Gly Gln Pro Ser Ser Ser Phe Thr Gly His Ile Gly
        355                 360                 365

Ser Leu Gln Gln Asp Ser Asp Leu Asp Asn Gly Lys Pro Ser His Ala
    370                 375                 380

<210> SEQ ID NO 106
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Cys Ser Val Pro Tyr Asp Tyr Asn Trp Tyr Ser Asn Trp Cys
1               5                   10

<210> SEQ ID NO 107
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term Pal--(miniPEG)3"

<400> SEQUENCE: 107

Cys Ser Val Pro Tyr Asp Tyr Asn Trp Tyr Ser Asn Trp Cys
1               5                   10

<210> SEQ ID NO 108
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term Palmitoyl-(miniPEG)3"
```

<400> SEQUENCE: 108

Cys Ser Phe Ser Gln Asn Lys Ser Val His Ser Phe Asp Tyr Asp Trp
1               5                   10                  15

Tyr Asn Val Ser Asp Gln Ala Asp Leu Lys Asn Cys
            20                  25

<210> SEQ ID NO 109
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Cys Ser Val His Ser Phe Asp Tyr Asp Trp Tyr Asn Val Cys
1               5                   10

<210> SEQ ID NO 110
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term Pal--(miniPEG)3"

<400> SEQUENCE: 110

Cys Ser Val His Ser Phe Asp Tyr Asp Trp Tyr Asn Val Cys
1               5                   10

<210> SEQ ID NO 111
<211> LENGTH: 12
<212> TYPE: PRT
<213> ORGANISM: Physcomitrella patens

<400> SEQUENCE: 111

Ser Val Pro Phe Asp Tyr Asn Leu Tyr Ser Asn Trp
1               5                   10

<210> SEQ ID NO 112
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Cys Ser Val Pro Phe Asp Tyr Asn Leu Tyr Ser Asn Trp Cys
1               5                   10

<210> SEQ ID NO 113
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

```
Cys Ser Ala Pro Tyr Asn Phe Asn Phe Tyr Ser Asn Trp Cys
1               5                   10
```

<210> SEQ ID NO 114
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

```
Cys Ser Arg Tyr Ser Ser Phe Asp Tyr Asp Trp Tyr Asn Val Cys
1               5                   10                  15
```

<210> SEQ ID NO 115
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

```
Cys Ser Glu Leu Ser Ser Phe Asn Phe Asp Trp Tyr Asn Val Cys
1               5                   10                  15
```

<210> SEQ ID NO 116
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

```
Cys Asn Val His Ser Phe Asp Tyr Asp Trp Tyr Asn Val Cys
1               5                   10
```

<210> SEQ ID NO 117
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

```
Cys Arg Val Glu Ser Phe Asn Tyr Asp Trp Tyr Asn Val Cys
1               5                   10
```

<210> SEQ ID NO 118
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

```
Cys Arg Val Glu Ser Phe Asp Phe Asp Trp Tyr Asn Ile Cys
1               5                   10
```

```
<210> SEQ ID NO 119
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Cys Arg Ile Asn Ser Phe Asp Tyr Asp Trp Tyr Asn Val Cys
1               5                   10

<210> SEQ ID NO 120
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Cys Thr Val Asn Ser Phe Asp Tyr Asp Trp Tyr Asn Val Cys
1               5                   10

<210> SEQ ID NO 121
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Cys Lys Val Asn Ser Phe Asp Tyr Asp Trp Tyr Asn Val Cys
1               5                   10

<210> SEQ ID NO 122
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Cys Thr Val His Ser Phe Asp Tyr Asp Trp Tyr Asn Val Cys
1               5                   10

<210> SEQ ID NO 123
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Cys Asn Ile Pro Phe Asn Phe Ser Leu Asn Lys Glu Arg Cys
1               5                   10

<210> SEQ ID NO 124
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Cys Ser Val Pro Tyr Gln Tyr Asn Trp Tyr Ser Asn Trp Cys
1               5                   10

<210> SEQ ID NO 125
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Cys Ser Val Pro Trp Glu Tyr Asn Phe Tyr Ser Asn Trp Cys
1               5                   10

<210> SEQ ID NO 126
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Cys Arg Ile Pro Tyr Asp Arg Gly Met Ile Val Asn Val Cys
1               5                   10

<210> SEQ ID NO 127
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Cys Lys Val Pro Tyr Asp Trp Asp Ser Val Ile Asn Leu Cys
1               5                   10

<210> SEQ ID NO 128
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Cys Gln Leu Pro Tyr Asp Val His Thr Tyr Asn Asp Trp Cys
1               5                   10

<210> SEQ ID NO 129
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                        Synthetic peptide"

<400> SEQUENCE: 129

Cys Leu Ala Pro Tyr Asp His Asn Arg Tyr Thr Gln Trp Cys
1               5                   10

<210> SEQ ID NO 130
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 130

Cys Ser Asn Pro Tyr Asp Leu Glu Ala Tyr Glu Asn Trp Cys
1               5                   10

<210> SEQ ID NO 131
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 131

Cys Ser Val Pro Tyr Asp Tyr Gln Gly Tyr Arg Asn Ile Cys
1               5                   10

<210> SEQ ID NO 132
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 132

Cys Ser Val Pro Tyr Asp Tyr Asn Val Tyr Leu Asn Lys Cys
1               5                   10

<210> SEQ ID NO 133
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 133

Cys Ile Gln Pro Tyr Asp Lys Asn Tyr Phe Gln Asn Phe Cys
1               5                   10

<210> SEQ ID NO 134
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 134
```

```
Cys Val Val Pro Tyr Asp Ile Asn Ile Lys Asp Asn Trp Cys
1               5                   10
```

<210> SEQ ID NO 135
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

```
Cys Ser Val Pro Tyr Asp Tyr Asn Pro Tyr Ser Asn Trp Cys
1               5                   10
```

<210> SEQ ID NO 136
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

```
Cys Ser Val Pro Tyr Asp Tyr Asn Lys Leu Lys Asn Trp Cys
1               5                   10
```

<210> SEQ ID NO 137
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

```
Cys Ser Val Pro Tyr Asp Tyr Asn Trp Arg Ser Ser Trp Cys
1               5                   10
```

<210> SEQ ID NO 138
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

```
Cys Ser Val Pro Tyr Asp Tyr Asn Trp Trp Ser Ala Trp Cys
1               5                   10
```

<210> SEQ ID NO 139
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

```
Cys Ser Val Pro Tyr Asp Tyr Asn Trp Gln Ser Asn Trp Cys
1               5                   10
```

```
<210> SEQ ID NO 140
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Cys Ser Val Gly Tyr Asp Tyr Asn Trp Tyr Ser Asn Trp Cys
1               5                   10

<210> SEQ ID NO 141
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Cys Ser Val Pro Tyr Asp Tyr Asn Trp Tyr Ser Asn Trp Cys
1               5                   10

<210> SEQ ID NO 142
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Cys Ser Val His Ser Trp Asp Tyr Asp Trp Tyr Asn Val Cys
1               5                   10

<210> SEQ ID NO 143
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Cys Ser Val His Ser Tyr Asp Phe Asp Trp Tyr Asn Val Cys
1               5                   10

<210> SEQ ID NO 144
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Cys Thr Leu Gln Ala Phe Asn Tyr Glu Trp Tyr Gln Leu Cys
1               5                   10

<210> SEQ ID NO 145
<211> LENGTH: 14
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 145

Cys Lys Tyr Glu Thr Phe Glu Tyr Gly Trp Tyr Asn Ile Cys
1               5                   10

<210> SEQ ID NO 146
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Cys His Gly Asp Ser Phe Gln Tyr Glu Trp Tyr Asn Leu Cys
1               5                   10

<210> SEQ ID NO 147
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Cys Ser Val His Ser Phe Asp Trp Asp Trp Tyr Asn Val Cys
1               5                   10

<210> SEQ ID NO 148
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Cys Ser Val His Ser Phe Asp Tyr Asp Tyr Tyr Asn Val Cys
1               5                   10

<210> SEQ ID NO 149
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Cys Ser Val His Ser Phe Asp Tyr Asp Phe Tyr Asn Val Cys
1               5                   10

<210> SEQ ID NO 150
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 150

Cys Ser Val His Ser Phe Asp Tyr Asp Trp Phe Asn Val Cys
1               5                   10

<210> SEQ ID NO 151
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Cys Ser Val His Ser Phe Asp Tyr Asp Trp Trp Asn Val Cys
1               5                   10

<210> SEQ ID NO 152
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Cys Ile Phe Asn Pro Phe Asp Tyr Asp Trp Tyr Asn Val Cys
1               5                   10

<210> SEQ ID NO 153
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Cys Gln Trp His Ser Phe Asp Tyr Asp Trp Tyr Asn Val Cys
1               5                   10

<210> SEQ ID NO 154
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Cys Asp Val His Pro Phe Asp Tyr Asp Trp Tyr Asn Val Cys
1               5                   10

<210> SEQ ID NO 155
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Cys Ser Val His Ser Gly Asp Tyr Asp Gly Gly Asn Val Cys
```

```
<210> SEQ ID NO 156
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Cys Ser Val His Ser Phe Asp Tyr Asp Trp Tyr Asn Val Cys
1               5                   10

<210> SEQ ID NO 157
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: HomoCys

<400> SEQUENCE: 157

Cys Ser Val Pro Tyr Asp Tyr Asn Trp Tyr Ser Asn Trp Cys
1               5                   10

<210> SEQ ID NO 158
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: HomoCys

<400> SEQUENCE: 158

Cys Ser Val Pro Tyr Asp Tyr Asn Trp Tyr Ser Asn Trp Cys
1               5                   10
```

DISPERSION AND DETACHMENT OF CELL AGGREGATES

CROSS-REFERENCE TO RELATED PATENT APPLICATIONS

This application is a Continuation of U.S. application Ser. No. 14/950,951 filed Nov. 24, 2015 now U.S. Pat. No. 9,700,058 B2, which is a Divisional of U.S. application Ser. No. 14/123,455 (National Stage of PCT/IB2012/001061) filed Apr. 4, 2014, now U.S. Pat. No. 9,284,351 B2, which claims priority from US Provisional Application 61/491,756, filed May 31, 2011. The aforesaid applications are incorporated herein by reference in their entirety.

This application contains a Sequence Listing which has been submitted in ASCII format via EFS-WEB and is hereby incorporated by reference in its entirety. Said ASCII copy created on Nov. 27, 2013, is named sequence.txt and is 60 KB.

FIELD OF THE INVENTION

The present invention relates to compositions and methods for dispersing or detaching a single cell organism from a surface or from other cells or single cell organisms, especially where the organism is in a biofilm or in vivo.

BACKGROUND OF THE INVENTION

Microorganisms can live and proliferate as individual cells swimming freely in the environment (e.g., plankton), or they can grow as highly organized, multicellular communities encased in a self-produced polymeric matrix in close association with surfaces and interfaces. The latter microbial lifestyle is referred to as biofilms. Biofilm formation represents an ancient, protected mode of growth that allows microbial survival in hostile environments and allows microorganisms to disperse and colonize new niches [Hall-Stoodley et al., Nat Rev Microbiol. (2004) 2(2):95-108]. The composition of biofilms is complex and variable among different microbial species and even within the same species under different environmental conditions. Nonetheless, biofilm formation represents the normal lifestyle of microorganism in the environment and all microbes can make biofilms. Previous studies revealed that bacterial biofilm formation progresses through multiple developmental stages differing in protein profiles [Sauer et al J Bacteriol. (2002) 184(4): 1140-54], beginning with attachment to surface, followed by the immigration and division to form microcolonies and finally maturation involving expression of matrix polymers. Bacteria within each biofilm stage display phenotypes and possess properties that are markedly different from those of the same group growing planktonically [Sauer et al., J Bacteriol. (2004) 186(21):7312-26]. Biofilms are a major cause of systemic infections (e.g., nosocomial infections) in humans.

The composition of biofilms is complex and variable among different microbial species and even within the same species under different environmental conditions. Nonetheless, biofilm formation represents the normal lifestyle of microorganism in the environment and all microbes can make biofilms. Previous studies revealed that bacterial biofilm formation progresses through multiple developmental stages differing in protein profiles [Sauer et al., J Bacteriol. (2002) 184(4): 1140-54], beginning with attachment to surface, followed by the immigration and division to form microcolonies and finally maturation involving expression of matrix polymers. Bacteria within each biofilm stage display phenotypes and possess properties that are markedly different from those of the same group growing planktonically [Sauer et al., J Bacteriol. (2004) 186(21):7312-26].

In the body, biofilms can be associated with tissues (e.g., inner ears, teeth, gums, lungs, heart valves and the urogenital tract) and can be a major source of systemic infections. An estimated 65% of bacterial infections in humans are biofilm in nature. Additionally, after forming biofilms, microorganisms tend to change their characteristics, sometimes drastically, such that doses of antibiotics which normally kill the organisms in suspended cultures are completely ineffective against the same microorganisms when the organisms are in attached or conglomerate biofilm form. See U.S. Pat. No. 7,189,351, incorporated by reference in its entirety.

One of the principal concerns with respect to products that are introduced into the body (e.g., contact lenses, central venous catheters, mechanical heart valves and pacemakers) or provide a pathway into the body is microbial infection and invariably biofilm formation. As these infections are difficult to treat with antibiotics, removal of the device is often necessitated, which is traumatic to the patient and increases the medical cost. PCT Application No. WO 06/006172 discloses the use of anti-amyloid agents, such as aromatic compounds, for inhibiting formation or disintegrating a pre existing biofilm. The application discloses that compounds preventing amyloid fibril formation in Alzheimers can act against fibril formation in biofilms, and concludes that amino acids having an aromatic arm are effective against biofilms. However, the analysis was limited to full length sequences.

Biofilms can cause, amongst a wide range of negative effects, accelerated corrosion in industrial systems, oil souring and biofouling. Bacterial aggregation can occur in agriculture [Monier et al., Applied and Environmental Microbiology, 70(1): 346-355 (2004); Biofilms in the food and beverage industries, Edited by P M Fratamico, B A Annous and N W Guenther, USDA ARS, USA, Woodhead Publishing Series in Food Science, Technology and Nutrition No. 181, Chapter 20, pages 517-535] and in water systems [Carlson et al., Zentralbl Bakteriol Orig B, 161(3): 233-247 (1975)]. Biofouling may be caused by the adhesion of organisms to any surface in a marine or freshwater environment, including cooling towers, water pipes and filters in cooling or desalinization installations, irrigation and power stations, and membranes, such as those used in wastewater and desalinization systems. Biofouling also occurs in aquaculture systems in fish farms. Furthermore the commercial shipping fleets of the world consume approximately 300 million tons of fuel annually. Without antifouling measures, that fuel consumption would increase by as much as 40%, equivalent to an extra 120 million tonnes of fuel annually. The economic cost of this was estimated as about $7.5 billion in 2000; a more recent estimate is $30 billion. Generally, biofilms are very difficult to eliminate since microbes growing within are highly organized and can withstand hostile environments, such as high temperatures and anti-microbial agents (e.g., antibiotics).

Since marine-aquatic plants and animals are continuously exposed to a large diversity and abundance of potentially harmful microorganisms in the form of biofilm, and it is known that marine life produce anti-microbial peptides, it is possible that broad spectrum natural factors that interfere with biofilm formation may also be present in marine life.

U.S. Publication No. 20070098745 discloses means of preventing biofilm formation by the use of reef fish microflora. This invention describes anti-biofilm substances derived from bacteria isolated from the epithelial mucosal surfaces of healthy coral reef fish (e.g., *Sparisoma ninidae* and *Lutjanus purpureus*). The bacterial isolates produce signals or toxins that prevent biofilm formation.

Cell clustering is not limited to microbial biofilms, but can exist in vivo. Alzheimer's Disease, for example, involves neuron clusters (i.e., neuritic plaques) in the brain [Tiraboschi et al., J. Neurology, 62(11): 1984-1989 (2004)]. In the body, bacterial aggregation can occur orally [Duffau et al., 16 Sep. 2005 RAI Congress, #0299; Liljemark et al., Infect. Immun., 31(3): 935-941 (1981)]; in sepsis [Reid et al., Current Microbiology, 20(3): 185-190 (1990)]; diarrhea [Bieber et al., Science, 280(5372): 2114-2118 (1998)]; in nosocomial infections [Bortz et al., Bulletin of Mathematical Biology, Volume 70, Number 3, 745-768]; in relation to drug efficacy [Kraal et al., J Dent Res 58(11): 2125-2131 (1979)]; in relation to peritoneal dialysis [Reid et al., Peritoneal Dialysis International, 10: 21-24 (1990)]; lung diseases [Sanchez et al., PLoS Pathog 6(8)]; and Crohn's disease [Isenmann et al., Digestive Diseases and Sciences, 47(2): 462-468 (2002)].

Cell clustering can also occur among white blood cells in vivo. For example, white blood cells can aggregate in whole blood as the result of cigarette smoking and lead to microvascular occlusion and damage [Hill et al., J. R. Soc. Med., 86(3):139-140 (1993)]. White blood cell aggregation can also occur in vascular disease [Belch et al., Thrombosis Research, 48(6):631-639 (1987)]. Macrophage-lymphocyte clustering is correlated to rheumatoid arthritis [Webb et al., Macrophage-lymphocyte clustering in rheumatoid arthritis, Ann. rheum. Dis. (1975), 34, 38] Additionally, Sun et al. state, "Both platelet aggregation and white blood cell aggregation are involved in pathological processes such as thrombosis, atherosclerosis and chronic inflammation. People in older age groups are likely to suffer from cardiovascular diseases and may have increased white cell and platelet aggregation which could contribute to this increased risk." [Sun et al., A study of whole blood platelet and white cell aggregation using a laser flow aggregometer, Platelets (2003) March 14(2):103-8.] Furthermore, adhesion and aggregation of white blood cells are involved in vascular diseases and thrombosis [Belch et al., Whole blood white cell aggregation: a novel technique, Thrombosis Research, 48; 631-639 (1987)].

Cell clustering also occurs in restenosis, which can develop as the result of implanted medical stents [Dangas et al., Circulation, 105:2586 (2005)]. Such clustering can lead to the occlusion of a blood vessel and dramatically reduced blood flow. One of the symptoms of the second stage of restenosis, which tends to occur 3-6 months after surgery, is platelet aggregation at the site of the injury [Michael Kirchengast*, Klaus Munter. Endothelin and restenosis. Cardiovascular Research 39 (1998) 550-555] and residual plaque burden outside the stent [Prati et al., In-Stent Neointimal Proliferation Correlates With the Amount of Residual Plaque Burden Outside the Stent. An Intravascular Ultrasound Study, Circulation, (1999) 99:1011-1014.], both phenomena being the main causes of in-stent neointimal proliferation. Patri et al concludes with the following: "Late in-stent neointimal proliferation has a direct correlation with the amount of residual plaque burden after coronary stent implantation, supporting the hypothesis that plaque removal before stent implantation may reduce restenosis."

SUMMARY OF THE INVENTION

The present invention provides a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). The present invention also provides a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In some embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

In some embodiments, the peptide is cyclic peptide. In other embodiments, the peptide is soluble. In some embodiments, the peptide is attached to a linker. In some embodiments, the linker is polyethylene glycol or palmitic acid. In other embodiments, the peptide is synthetic.

The present invention also provides a composition comprising a protein or peptide, wherein said composition is capable of detaching a single cell organism from a surface or from other single cell organisms. In some embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

In some embodiments, peptide is a cyclic peptide. In some embodiments, the peptide is soluble. In other embodiments, the peptide is attached to a linker. In some embodiments, the linker is polyethylene glycol or palmitic acid. In some embodiments, the peptide is synthetic. In some embodiments, the organism is in a biofilm. In some embodiments, the organism is an aquatic microorganism. In some embodiments, the organisms are attached in a cluster or aggregate. In some embodiments, the composition is capable of breaking or dispersing said cluster or aggregate. In some embodiments, the detaching affects the ability of said organism to produce polysaccharide matrix. In some embodiments, the surface is a selected from the group comprising a fabric, a fiber, a foam, a film, a concrete, a masonry, a glass, a metal and a plastic.

The present invention also provides a method of detaching a single cell organism from a surface or from other single cell organisms, comprising contacting said organism with a composition comprising a protein or peptide. In some embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

In some embodiments, the peptide is a cyclic peptide. In some embodiments, the peptide is soluble. In other embodiments, the peptide is attached to a linker. In some embodiments, the linker is polyethylene glycol or palmitic acid. In some embodiments, the peptide is synthetic. In some embodiments, the surface is selected from the group comprising a fabric, a fiber, a foam, a film, a concrete, a masonry, a glass, a metal and a plastic. In some embodiments, the organism is a in a biofilm. In some embodiments, the organism is an aquatic microorganism. In some embodiments, the organisms are attached in a cluster or aggregate. In some embodiments, composition breaks or disperses said cluster or aggregate. In some embodiments, the composition prevents said organism from producing polysaccharide matrix. In some embodiments, the surface is a selected from the group comprising a fabric, a fiber, a foam, a film, a concrete, a masonry, a glass, a metal and a plastic.

The present invention also provides a pharmaceutical composition comprising a protein or peptide, wherein the composition is capable of detaching a single cell organism from a surface or from other single cell organisms, and a pharmaceutically acceptable carrier or diluent. In some embodiments, the pharmaceutical composition comprises a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

The present invention also provides a method of preventing or treating a pathogen infection in a subject in need thereof, the method comprising administering to the subject a therapeutically effective amount of a pharmaceutical composition comprising a protein or peptide, wherein said composition is capable of detaching a single cell organism from a surface or from other single cell organisms. In some embodiments, the pharmaceutical composition comprises a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

The present invention also provides a method of increasing the effectiveness of a pharmaceutical composition, the method comprising administering a composition comprising a protein or peptide, wherein the composition is capable of detaching a microorganism from a surface or from other microorganisms to a subject in need of the pharmaceutical composition. In some embodiments, the pharmaceutical composition comprises a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), where in $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVP- WEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

In some embodiments, the pharmaceutical composition is an antibiotic.

The present invention also provides a method of identifying an anti-biofilm composition, the method comprising: (a) contacting said biofilm with a plurality of compositions, each composition comprising a protein or peptide; (b) assaying the ability of said biofilm to resist anti-biofilm activity, wherein said anti-biofilm activity comprises detaching said biofilm from a surface or breaking up said biofilm; and (c) identifying from said plurality of compositions at least one composition having said anti-biofilm activity above a predetermined threshold, thereby identifying the anti-biofilm composition. In some embodiments, the composition comprises a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; is $X^{11}$ or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

The present invention also provides a medical device comprising a composition comprising a protein or peptide, wherein the composition is capable of detaching a single cell organism from a surface or from other single cell organisms. In some embodiments, the medical device comprises a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30);

KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

The present invention also provides a method of dispersing a biofilm or detaching biofilm formation from a surface, the method comprising treating water with or coating said surface with a composition comprising a protein or peptide, wherein the composition is capable of detaching a single cell organism from a surface or from other single cell organisms. In some embodiments, the method comprises a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

The present invention also provides a method of treating a disease, comprising administering a peptide consisting of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 1), wherein $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F, R, W, V, H, L, K or I; $X^7$ is N, S, G, D, H, E, Q or I; $X^8$ is W, L, F, M S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E, wherein the peptide is not SVPYDYNWYSNW (SEQ ID NO: 2). In other embodiments, the peptide consists of amino acids $X^1$-$X^2$-$X^3$-$X^4$-$X^5$-$X^6$-$X^7$-$X^8$-$X^9$-$X^{10}$-$X^{11}$-$X^{12}$ (SEQ ID NO: 3), wherein $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L, wherein the peptide is not SVHSFDYDWYNV (SEQ ID NO: 4).

In specific embodiments, the peptide is SVPFDYNLYSNW (SEQ ID NO: 5); SAPYNFNFYSNW (SEQ ID NO: 6); NIPFNFSLNKER (SEQ ID NO: 7); SVPYQYNWYSNW (SEQ ID NO: 8); SVPWEYNFYSNW (SEQ ID NO: 9); RIPYDRGMIVNV (SEQ ID NO: 10); KVPYDWDSVINL (SEQ ID NO: 11); QLPYDVHTYNDW (SEQ ID NO: 12); LAPYDHNRYTQW (SEQ ID NO: 13); SNPYDLEAYENW (SEQ ID NO: 14); SVPYDYQGYRNI (SEQ ID NO: 15); SVPYDYNVYLNK (SEQ ID NO: 16); IQPYDKNYFQNF (SEQ ID NO: 17); VVPYDINIKDNW (SEQ ID NO: 18); SVPYDYNPYSNW (SEQ ID NO: 19); SVPYDYNKLKNW (SEQ ID NO: 20); SVPYDYNWRSSW (SEQ ID NO: 21); SVPYDYNWWSAW (SEQ ID NO: 22); SVPYDYNWQSNW (SEQ ID NO: 23); ELSSFNFDWYNV (SEQ ID NO: 24); RYSSFDYDWYNV (SEQ ID NO: 25); NVHSFDYDWYNV (SEQ ID NO: 26); RVESFNYDWYNV (SEQ ID NO: 27); RVESFDFDWYNI (SEQ ID NO: 28); RINSFDYDWYNV (SEQ ID NO: 29); TVNSFDYDWYNV (SEQ ID NO: 30); KVNSFDYDWYNV (SEQ ID NO: 31); TVHSFDYDWYNV (SEQ ID NO: 32); SVHSWDYDWYNV (SEQ ID NO: 33); SVHSYDFDWYNV (SEQ ID NO: 34); TLQAFNYEWYQL (SEQ ID NO: 35); KYETFEYGWYNI (SEQ ID NO: 36); HGDSFQYEWYNL (SEQ ID NO: 37); SVHSFDWDWYNV (SEQ ID NO: 38); SVHSFDYDYYNV (SEQ ID NO: 39); SVHSFDYDFYNV (SEQ ID NO: 40); SVHSFDYDWFNV (SEQ ID NO: 41); SVHSFDYDWWNV (SEQ ID NO: 42); IFNPFDYDWYNV (SEQ ID NO: 43); QWHSFDYDWYNV (SEQ ID NO: 44) or DVHPFDYDWYNV (SEQ ID NO: 45).

In some embodiments, the disease is autoimmune, inflammatory or degenerative disease. In some embodiments, the disease is Alzheimer's Disease.

DETAIL DESCRIPTION OF THE PREFERRED EMBODIMENTS

Figure 1:
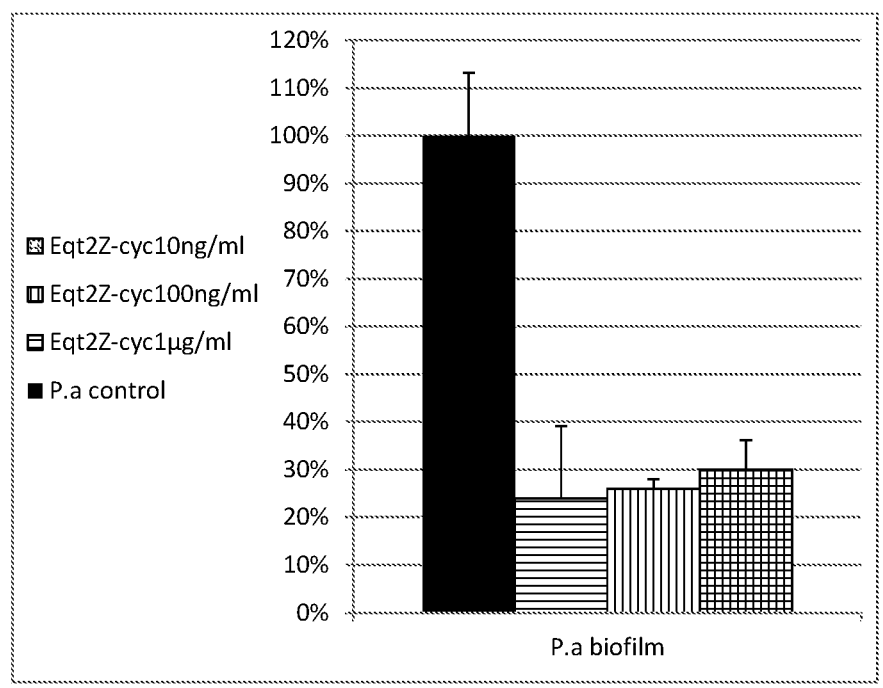
FIG. 1 shows the detachment of *Pseudomonas aeruginoas* biofilm from a well in a 96-well culture plate after incubating the microorganism overnight to create the biofilm and subsequently incubating the biofilm with Eqt2Z-cyc peptide overnight.

The present invention relates to compositions and methods comprising a protein or a peptide which has one or more effects relating to detaching a single cell organism from a surface or other single cell organisms, especially where the organism is in a biofilm.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are provided for the convenience of the reader. All the information contained therein is incorporated herein by reference.

Definitions

As used herein, the term "isolated" refers to a composition that has been removed from its in vivo location. Preferably the isolated compositions of the present invention are substantially free from other substances (e.g., other proteins that do not comprise anti-adhesive effects) that are present in their in vivo location (i.e., purified or semi-purified). Isolated proteins and peptides may optionally be synthetic or obtained from natural sources, including optionally by being expressed in vivo using genetic engineering techniques.

As used herein the phrase "single cell organism" refers to a unicellular organism also termed a microorganism or a microbe. The single cell organism of the present invention can be a eukaryotic single cell organism (e.g., protozoa or fungi for example yeast) or a prokaryotic single cell organism (e.g., bacteria or archaea). The single cell organisms of the present invention may be in any cellular environment, such as for example, in a biofilm, as isolated cells or as a cell suspension.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: Actinomyces spp., Bacillus anthracis, Bifidobacterium spp., Clostridium botulinum, Clostridium perfringens, Clostridium spp., Clostridium tetani, Corynebacterium diphtheriae, Corynebacterium jeikeium, Enterococcus faecalis, Enterococcus faecium, Erysipelothrix rhusiopathiae, Eubacterium spp., Gardnerella vaginalis, Gemella morbillorum, Leuconostoc spp., Mycobacterium abscessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia spp., Peptococcus niger, Peptostreptococcus spp., Proprionibacterium spp., Sarcina lutea, Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae (group B Streptococcus), Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes (group A Streptococcus), Streptococcus salivarius, Streptococcus sanguis.

The term "Gram-negative bacteria" as used herein refer to bacteria characterized by the presence of a double membrane surrounding each bacterial cell. Representative Gram-negative bacteria include Acinetobacter calcoaceticus, Acinetobacter baumannii, Actinobacillus actinomycetemcomitans, Aeromonas hydrophila, Alcaligenes xylosoxidans, Bacteroides, Bacteroides fragilis, Bartonella bacilliformis, Bordetella spp., Borrelia burgdorferi, Branhamella catarrhalis, Brucella spp., Campylobacter spp., Chalmydia pneumoniae, Chlamydia psittaci, Chlamydia trachomatis, Chromobacterium violaceum, Citrobacter spp., Eikenella corrodens, Enterobacter aerogenes, Escherichia coli, Flavobacterium meningosepticum, Fusobacterium spp., Haemophilus influenzae, Haemophilus spp., Helicobacter pylori, Klebsiella pneumoniae, Klebsiella spp., Legionella spp., Leptospira spp., Moraxella catarrhalis, Morganella morganii, Mycoplasma pneumoniae, Neisseria gonorrhoeae, Neisseria meningitidis, Pasteurella multocida, Plesiomonas shigelloides, Prevotella spp., Proteus spp., Providencia rettgeri, Pseudomonas aeruginosa, Pseudomonas spp., Rickettsia prowazekii, Rickettsia rickettsii, Rochalimaea spp., Salmonella spp., Salmonella typhi, Serratia marcescens, Shigella spp., Shigella sonnei, Treponema carateum, Treponema pallidum, Treponema pallidum endemicum, Treponema pertenue, Veillonella spp., Vibrio cholerae, Vibrio vulnificus, Yersinia enterocolitica, Yersinia pestis.

The term "fungi" as used herein refers to the heterotrophic organisms characterized by the presence of a chitinous cell wall, and in the majority of species, filamentous growth as multicellular hyphae. Representative fungi whose adhesion may be prevented according to the method of the present invention include Candida albicans, Saccharomyces cerevisiae, Candida glabrata, Candida parapsilosis and Candida dubliniensis.

As used herein the term "biofilm" refers to an extracellular matrix in which single cell organisms can be dispersed and/or form colonies. The biofilm typically is made of polysaccharides and other macromolecules.

As used herein, the term "detach" refers to removing a single cell organism, in vitro or in vivo, from a surface to which the cell is adhered (e.g., by reducing the rate of growth on a surface) or removing the cell from other single cell organisms to which they are adhered. Preferably, the compositions of the present invention detach cells from adherence by as much as 10%, more preferably by 20%, more preferably by 30%, more preferably by 40%, more preferably by 50%, more preferably by 60%, more preferably by 70%, more preferably by 80%, more preferably by 90% and most preferably by 100% as measured by an adhesion assay. Exemplary detachment assays are described herein below and in the Examples section that follows.

"Detachment" of a biofilm occurs when a single or cluster of cell organisms in the biofilm detaches from a surface and "dispersion" of a biofilm occurs when single cell organisms in a biofilm detach from each other.

As used herein the term "contacting" refers to the positioning of the compositions of the present invention such that they are in direct or indirect contact with the adhesive single cell organisms in such a way that the active agent comprised within is able to detach of cells therefrom. Thus, the present invention contemplates both applying the compositions of the present invention to a desirable surface and/or directly to the adhesive cells. Contacting the compositions with a surface can be effected using any method known in the art including spraying, spreading, wetting, immersing, dipping, painting, ultrasonic welding, welding, bonding or adhering. The compositions of the present invention may be attached as monolayers or multiple layers.

A "peptidomimetic organic moiety" can optionally be substituted for amino acid residues in a peptide according to the present invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the composition at least substantially retains its physiological activity as compared to the native peptide according to the present invention.

As used herein the term "chemical modification", when referring to a peptide according to the present invention, refers to a peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

As used herein the term "medical device" refers to any implant, instrument, apparatus, implement, machine, device or any other similar or related object (including any component or accessory), which is intended for use in the diagnosis, treatment, cure or prevention of disease or other conditions. Such medical device is intended for use in man or other animals and is anticipated to affect the structure or any function of the body. Such medical device does not achieve its primary intended purposes through chemical action and is not dependent upon being metabolized for the achievement of its primary intended purposes.

As used herein the term "implant" refers to any object intended for placement in a human body that is not a living tissue. The implant may be temporary or permanent. An implant can be an article comprising artificial components, such as catheters or pacemakers. Implants can also include naturally derived objects that have been processed so that their living tissues have been devitalized. As an example, bone grafts that have been processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies. The present invention therefore envisions coating medical devices with the compositions of the present invention to prevent microorganism adherence thereto so as to reduce/eliminate any possible cell aggregation and biofilm formation known to occur following implantation. Device-related infections usually result from the introduction of microorganisms, primarily bacteria, during the device insertion or implantation procedure, or from attachment of blood-borne organisms to the newly inserted device and their subsequent propagation on its surface. Coating the medical device with the compositions of the present invention will therefore inhibit biofilm formation of one or more microbial species, will prevent medical device related infections, and consequently will reduce the need of antibiotic treatment or removal of the medical device from the subject.

As used herein the term "anti-biofouling agents" refers to the compounds used to protect underwater surfaces from attaching single cell organisms. These single cell organisms include microorganism such as bacteria and fungi.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

As used herein the term "excipient" refers to an inert substance added to a pharmaceutical composition to further facilitate administration of an active ingredient.

As used herein, the phrase "sessile aquatic organism" refers to an aquatic organism which is not freely moving for at least some a part of its life cycle. Aquatic sessile organisms are usually permanently attached to a solid substrate of some kind, such as to a rock or the hull of a ship due to physical anchorage to the substrate, or for any other reason (e.g., stone fish). Exemplary sessile organisms include, but are not limited to, sessile cnidarians such as corals, sea anemones (e.g., *Actinia equine* and *Aiptasia pulchella*), sea pens, aquatic sessile larva (e.g., jellyfish larva), tube dwelling anemones and hydroids (e.g., *Chlorohydra viridissima* and *Hydra vulgaris*). Exemplary fish that may be used according to this aspect of the present invention are preferably those dwelling in shallow waters or those that hide at the bottom layer of the ocean, sometimes in holes or caves. Such fish include eel and catfish.

As used herein the term "subject in need thereof" refers to a mammal, preferably a human subject.

As used herein the term "treating" refers to curing, reversing, attenuating, alleviating, minimizing, suppressing or halting the deleterious effects of a pathogen infection.

As used herein the phrase "pathogen infection" refers to any medical condition which is caused by a pathogenic organism. Examples of pathogen infections include, but are not limited to, chronic infectious diseases, subacute infectious diseases, acute infectious diseases, viral diseases, bacterial diseases, protozoan diseases, parasitic diseases, fungal diseases, *Mycoplasma* diseases, archaea diseases and prion diseases. Pathogen infection can be caused by an organism capable of growing in or on a biofilm. Examples of pathogen infections caused by microbial biofilms include native valve endocarditis (NVE), otitis media (OM), chronic bacterial prostatitis, cystic fibrosis (CF) and periodontitis. Additional pathogen infections that are not specifically attributed to biofilms include, but are not limited to urinary infections, female genital tract infections and pneumonia. Infections due to implantation of medical devices include vascular catheter infections, arterial prosthetic infections, infections of prosthetic heart valves, prosthetic joint infections, infections of central nervous system shunts, orthopedic implant infections, pacemaker and defibrillator infections, hemodialysis and peritoneal dialysis infections, ocular infections, urinary tract infections, infections of the female genital tract, infections associated with endotracheal intubation and tracheostomy and dental infections.

As used herein the phrase "pathogenic organism" refers to any single cell organism which is capable of causing disease, especially a living microorganism such as a bacteria or fungi. Preferably the pathogenic organism is capable of growing in or on a biofilm. Many common pathogenic organisms exist in mammals (e.g. humans) as biofilms and cause disease. These include, but are not limited to, *Mannheimia haemolytica* and *Pasteurella multocida* (causing pneumonia), *Fusobacterium necrophorum* (causing liver abscess), *Staphylococcus aureus* and *Pseudomonas aeruginoas* (causing wound infections), *Escherichia coli* and *Salmonella* spp (causing enteritis), *Staphylococcus aureus* and *Staphylococcus epidermidis* (causing OM), and *Streptococci* sp., *Staphylococci* sp., *Candida*, and *Aspergillus* sp. (causing NVE).

Applications

The present invention has many applications. One application is to use a composition comprising the protein or peptide to disperse a biofilm or detach a biofilm from a surface. Another application is to use the composition to combat systemic infections (e.g., nosocomial infections) in patient caused by microbial biofilms in vivo. Another application is to use the composition to disperse or detach a biofilm present in other fields, including the food, agriculture, pharmaceutical, paint, water, shipping and engineering industries. Another application is to use the composition to disperse or detach a biofilm where coaggregation—i.e., aggregation of more than one species that create a single cluster occurs. The foregoing applications are not limiting and other applications are appropriate in which a composition can be used to detach a microorganism from a surface or from other microorganisms. Another application is to use the composition to treat disease, including autoimmune, inflammatory diseases and degenerative diseases such as Alzheimer's Disease. These diseases are caused by cell aggregation or clustering and the use of the inventive peptides to prevent or dissociate cell aggregates can lead to alleviation of the disease. Another application is to use the composition to treat restenosis, including restenosis caused by implanted medical stents. Another application is to use the composition to treat blood cell clustering, including white blood cells.

Exemplary bacterial cells that can be detached from surfaces and from each other according to the method of the present invention include gram positive bacteria and gram negative bacteria.

Exemplary surfaces upon which single cell organisms can attach and which are contemplated by the present invention include fabrics, fibers, foams, films, concretes, masonries, glass, metals, plastics, polymers, and like.

Exemplary devices whose surfaces are susceptible to biofilm formation and which are contemplated by the present invention include, but are not limited to, vessel hulls, automobile surfaces, air plane surfaces, membranes, filters, and industrial equipment. The surface may also be comprised in medical devices, instruments, and implants.

Examples of such medical devices, instruments, and implants include any object that is capable of being implanted temporarily or permanently into a mammalian organism, such as a human. Representative medical devices, instruments, and implants that may be used according to the present invention include, for example, central venous catheters, urinary catheters, endotracheal tubes, mechanical heart valves, pacemakers, vascular grafts, stents and prosthetic joints.

Medical devices that may be coated according to the teachings of the present invention include, but are not limited to, artificial blood vessels, catheters and other devices for the removal or delivery of fluids to patients, artificial hearts, artificial kidneys, orthopedic pins, prosthetic joints, plates and implants; catheters and other tubes (including urological and biliary tubes, endotracheal tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, mechanical heart valves, artificial joints, artificial larynxes, otological implants), anastomotic devices, vascular catheter ports, vascular stents, clamps, embolic devices, wound drain tubes, ocular lenses, dental implants, hydrocephalus shunts, pacemakers and implantable defibrillators, needleless connectors, voice prostheses and the like. Another possible application of the compositions of the present invention is the coating of surfaces found in the medical and dental environment. Such surfaces include the inner and outer aspects of various instruments and devices, whether disposable or intended for repeated uses. Such surfaces include the entire spectrum of articles adapted for medical use, including without limitation, scalpels, needles, scissors and other devices used in invasive surgical, therapeutic or diagnostic procedures; blood filters. Other examples will be readily apparent to practitioners in these arts.

Surfaces found in the medical environment also include the inner and outer aspects of pieces of medical equipment, medical gear worn or carried by personnel in the health care setting. Such surfaces can include surfaces intended as biological barriers to infectious organisms in medical settings, such as gloves, aprons and face shields. Commonly used materials for biological barriers are thermoplastic or polymeric materials such as polyethylene, dacron, nylon, polyesters, polytetrafluoroethylene, polyurethane, latex, silicone and vinyl. Other surfaces can include counter tops and fixtures in areas used for medical procedures or for preparing medical apparatus, tubes and canisters used in respiratory treatments, including the administration of oxygen, of solubilized drugs in nebulizers and of anesthetic agents. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered. The compositions of the present invention can be used on the surface of or within these medical devices to provide long term protection against colonization by single cell organisms and reduce the incidence of device-related infections. These compositions can also be incorporated in combination with an anti-microbial agent (e.g., antibiotic agent) into coatings for medical devices. Such a combination will sufficiently kill or inhibit the initial colonizing bacteria and prevent device-related infections as long as the substance is presented in an inhibitory concentration at the device-microbe interface.

The compositions of the present invention can be directly incorporated into the polymeric matrix of the medical device at the polymer synthesis stage or at the device manufacture stage. The compositions can also be covalently attached to the medical device polymer. These and many other methods of coating medical devices are evident to one of ordinary skill in the art.

Additional surfaces that can be treated according to the teachings of the present invention include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Thus, the compositions of the present invention can be used for removal of disease-causing microorganisms from external surfaces. These can include, for example food processing equipment for home use, materials for infant care, tampons, soap, detergents, health and skincare products, household cleaners and toilet bowls.

The surface may be also be laboratory articles including, but not limited to, microscopic slide, a culturing hood, a Petri dish or any other suitable type of tissue culture vessel or container known in the art.

The inventors of this application also envision the use of the compositions of the present invention as anti-Biofouling agents.

Underwater surfaces include any water immersed surface, including ships'/boats's hulls (i.e., the body or frame of a ship or boat), submergence vehicles, navigational aids, screens, nets, constructions, floating or emplaced offshore platforms (e.g., docks), buoys, signaling equipment and articles which come into contact with sea water or salty water. Other underwater surfaces include structures exposed to sea water including pilings, marine markers, undersea conveyances like cabling and pipes, fishing nets, bulkheads, cooling towers, and any device or structure that operates submerged.

The compositions of the present invention can be incorporated into marine coatings to limit undesirable marine biofouling. Thus, the anti-biofouling agents of the present invention can be formulated so as not to contain toxic materials (such as heavy metals), and still retain their efficacy. The anti-biofouling paint of the present invention may further contain binders(s), pigment(s), solvent(s) and additive(s).

Examples of solvents that may be used include aromatic hydrocarbons such as xylene and toluene; aliphatic hydrocarbons such as hexane and heptane, esters such as ethyl acetate and butyl acetate; amides such as N-methylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvents may be used alone or in combination thereof.

Examples of binders that may be used include alkyd resin, acrylic or vinyl emulsions, polyurethane resins, epoxy resins, silicone based resins, acrylic resins, inorganic silicate based resins, vinyl resins, particularly a vinyl chloride/vinyl acetate copolymer, and rosin. Examples of pigments that may be used include titanium dioxide, cuprous oxide, iron oxide, talc, aluminum flakes, mica flakes, ferric oxide, cuprous thiocyanate, zinc oxide, cupric acetate meta-arsenate, zinc chromate, zinc dimethyl dithiocarbamate, zinc ethylene bis(dithiocarbamate) and zinc diethyl dithiocarbamate.

Examples of additives that may be incorporated into the coating composition include dehumidifiers, wetting/dispersing agents, anti-settling agents, anti-skinning agents, drying/curing agents, anti-marring agents and additives ordinarily employed in coating compositions as stabilizers and antifoaming agents. Additionally, any antibiotic which is relatively insoluble in seawater can be used with an anti-biofouling marine paint.

Methods of preparing marine anti-biofouling paints are explained in detail in U.S. Pat. Nos. 4,678,512; 4,286,988; 4,675,051; 4,865,909; and 5,143,545.

The compositions of the present invention may also be used for providing antibacterial properties in cosmetics, to prevent spoiling of the product.

The compositions may further be used to provide an antibacterial effect to the mouth, teeth and gums, such as by incorporation in a toothpaste, mouthwash, or chewing gum. Taken together the present teachings portray a wide range of novel anti-adhesive agents isolated from organisms such as aquatic organisms and moss. The broad spectrum of the detachment effects of these anti-adhesive agents (e.g., removing adhesion of gram positive and gram negative bacteria) together with their ability to effect the initial, vulnerable stages of microbial biofilm formation, makes these agents prime candidates as anti-biofilm agents. Moreover, the anti-adhesive agents described herein are clonable enabling modifications and mass production thereof. In addition their stability (i.e., resistance to environmental conditions) makes these agents suitable for a diverse array of applications.

It will be appreciated that treatment of infectious diseases according to the present invention may be combined with other treatment methods known in the art (i.e., combination therapy). These include, but are not limited to, antimicrobial agents such as penicillins, cephalosporins, carbapenems, aminoglycosides, macrolides, lincomycins, tetracyclines, chloramphenicol, and griseofulvin. Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For topical administration, the compositions of the present invention may be formulated as a gel, a cream, a wash, a rinse or a spray.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses. Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran.

Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides. Pharmaceutical compositions suitable for use in the context of the present invention include compositions wherein the active ingredients are contained in an amount effective to achieve the intended purpose. More specifically, a "therapeutically effective amount" means an amount of active ingredients (e.g., an aquatic organism composition) effective to prevent, alleviate, or ameliorate symptoms of a pathogenic infection (e.g., fever) or prolong the survival of the subject being treated. Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans. Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.) Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved. The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a 'pharmaceutically acceptable carrier may also be prepared, placed in an appropriate container, and labeled for treatment of an indicated condition, as further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Proteins and Peptides

The protein or peptide in the compositions can be obtained from different sources. Natural proteins and peptides can be found in animals, including humans. Also, marine and fresh water plants and organisms, including soft bodied water invertebrates, fish and moss produce several factors that can prevent microbial colonization on their body surface since they lack specific immunity and are surrounded by broad spectrum species of microbial organisms. The most "sensitive" organisms are invertebrates belong to the phylum cnidaria that include the sea anemones, corals, jellyfish, hydroids, medusae, and sea fans. Such soft bodied organism, which lack physical protection such as scales or shells, use proteins and secondary metabolites to protect themselves from the microbial environment surrounding them.

Additionally, it has been previously reported that marine organisms (e.g., sponges) produce secondary metabolites that exhibit antibacterial and antifungal activities [Amade et al., supra]. Moreover, sea anemones (e.g., *Actinia equina*) have been shown to produce toxic, pore forming peptides (i.e., equinatoxins), which lyse and kill eukaryotic cells similarly to other small antimicrobial peptides [Anderluh et al., supra].

Although it is known in the art that the full length sequences of various proteins are related to their cytolysic function, the specific peptides responsible for the cytolysic effect have not been previously identified.

Whilst reducing the present invention to practice, the present inventors discovered that human proteins and aquatic sessile organisms comprise anti-biofilm properties. As is shown in the Examples section which follows, the present inventors have shown that proteins and peptides found in humans and sessile cnidarians (e.g., sea anemones) can cause microorganisms to detach from surfaces and from each other (FIGS. 1-6). These proteins and peptides were not bactericidal and did not affect bacterial growth.

Taken together the present teachings portray a wide range of novel anti-adhesive agents derived from human and aquatic sessile organisms, in particular from sessile cnidarians. The broad spectrum of the anti-biofilm effects of these agents makes these agents prime candidates as anti-biofilm agents. Moreover, the anti-adhesive agents described herein are clonable enabling modifications and mass production thereof. In addition their stability (i.e., resistance to environmental conditions) makes these agents suitable for a diverse array of applications.

The present inventors have demonstrated that several active fractions obtained from sea anemones using liquid chromatography separations show a high level of prevention of microbial adherence to abiotic surfaces. The sea anemone includes 46 families that can be found in water sources around the world. Most sea anemones are sessile, with a specialized foot used to anchor them in soft substrates, or attach themselves to rocks and corals. The anti-adhesive activity was demonstrated with several species of sea anemone belonging to different genera: *Actinia equine*, *Aiptasia* and *Ammonia*. The N terminus region of anemone cytotoxin has been shown to be involved in the cytotoxic effect [Ref: Kristan K, Podlesek Z, Hojnik V, Gutierrez-Aguirre I, Guncar G, Turk D, Gonzalez-Manas J M, Lakey J H, Macek P, Anderluh G (2004): Pore formation by equinatoxin, an eukaryotic pore-forming toxin, requires a flexible N-terminal region and a stable beta sandwich. J Biol Chem. 279(45):46509-46517]. A protein having some resemblance to the C terminus region of anemone cytotoxin superfamily (pfam06369) (a superfamily cluster is a set of conserved domain models, from one or more source databases, that generate overlapping annotation on the same protein sequences. These models are assumed to represent evolutionarily related domains and may be redundant with each other), which region is not involved in cytotoxicity, has also been identified in fish by the present inventors. This protein has a highly conserved region, with unknown function, which is also a Trp-rich domain, and may be important for binding of the protein to lipid membrane. The present inventors have also found this region in the moss *Physcomitrella patens*. The present inventors therefore hypothesized that this region provides a peptide which is highly effective in dispersing biofilms or detaching biofilms from surfaces, while being devoid of cytotoxic activity.

Based on bioinformatics analysis, it is believed that the protein has changed in upper organisms (including in humans), at the highly conserved region, to FDYDWY (SEQ ID NO: 46), that can be found in proteins, represented in the GenBank as GPCR 137b like, with size range from 128aa-400aa. In humans, this peptide is part of the G protein-coupled receptor 137B (GENE ID: 7107 GPR137B) located at 269-274. Based on UniProtKB/Swiss-Prot entry 060478, the region, which starts at 259 and ends at 292, is an extracellular region, which supports the theory that this peptide is the active part of the protein. Bioinformatics analysis of the ancient sea organism Ciona intestinalis identified a 368 amino acid protein, similar to the G protein-coupled receptor 137ba [ GeneBank Accession number XP_002125109]. The region similar to the anti adhesive peptide is SPLRCSELSSFNFDWYNVSDQADLVN (SEQ ID NO: 47). Based on this information, and the fact that Ciona intestinalis is also exposed to a large diversity of microorganisms, the peptide FNFDWY (SEQ ID NO: 48) is also highly effective in dispersing biofilms or detaching biofilms from surfaces, while being devoid of cytotoxic activity.

The protein or peptide may be natural and isolated from any animal. Preferably, the animal is a vertebrate, such as, for example, a fish, an amphibian (including a frog, a toad, a newt or a salamander), a bird, a reptile (such as a crocodile, a lizard, a snake, a turtle, a tortoise or a terrapin) or a mammal (including a human).

According to some embodiments, the peptide comprises part of a sequence comprising up to about 30, up to about 40, or up to about 50 amino acids.

The peptides of the present invention may optionally comprise at least two sequences, connected by a linker of some type, such that the N-terminal of a first peptide sequence is connected to the C-terminal of the linker, and the C-terminal of a second peptide sequence is connected to the N-terminal of the linker.

The peptides of the present invention can be cyclized (i.e., in cyclic form) and are indicated in this application as such with the term "cyc."

In one embodiment, each peptide is modified with a cysteine at the C-terminal and a cysteine at the N-terminal, wherein the C- and N-terminals are S—S bridged. In specific embodiments, one or more of the peptides are modified with a cysteine at the C-terminal and a cysteine at the N-terminal, wherein the C- and N-terminals are S—S bridged.

Exemplary peptides contain a domain which comprises at least one peptide and which is effective against adhesion of a single cell organism to a surface or to other single cell organisms. More preferably, the domain is included as part of a protein. Optionally and most preferably, the domain exhibits anti-adhesive behavior, for example for the detachment and/or treatment of a biofilm, but does not exhibit cytotoxic behavior.

The peptides may optionally be altered so as to form non-peptide analogs, including but not limited to replacing one or more bonds with less labile bonds, cyclization and the like. Additionally or alternatively, a peptide may optionally be converted to a small molecule through computer modeling, as described for example in PCT Application No. WO/2007/147098, hereby incorporated by reference as if fully set forth herein.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875 5880 (1988)); isosteres of amide bonds (Jones et al, Tetrahedron Lett. 29: 3853 3856 (1988)); LL 3 amino 2 propenidone 6 carboxylic acid (LL Acp) (Kemp et al., J. Org. Chem. 50:5834 5838 (1985)). Similar analogs are shown in Kemp et al., Tetrahedron Lett. 29:5081 5082 (1988) as well as Kemp et al., Tetrahedron Lett. 29:5057 5060 (1988), Kemp et al., Tetrahedron Lett. 29:4935 4938 (1988) and Kemp et al., J. Org. Chem. 54:109 115 (1987). Other suitable but exemplary peptidomimetics are shown in Nagai and Sato, Tetrahedron Lett. 26:647 650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323 333 (1990); Garvey et al., J. Org. Chem. 56:436 (1990). Further suitable exemplary peptidomimetics include hydroxy 1,2,3,4 tetra-hydroisoquinoline 3 carboxylate (Miyake et al., J. Takeda Res. Labs 43:53 76 (1989)); 1,2,3,4 tetrahydro-isoquinoline 3 carboxylate (Kazmierski et al., J. Am. Chem. Soc. 133: 2275 2283 (1991)); histidine isoquinolone carboxylic acid (HIC) (Zechel et al., Int. J. Pep. Protein Res. 43 (1991)); (2S, 3S) methyl phenylalanine, (2S, 3R) methyl phenylalanine, (2R, 3S) methyl phenylalanine and (2R, 3R) methyl phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example. In the present invention any part of a peptide may optionally be chemically modified, i.e., changed by addition of functional groups. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

The compositions of the present invention may also be expressed in-vivo using genetic engineering techniques (e.g., using transgenic aquatic sessile organisms).

The compositions of the present invention may be devoid of cytotoxic or cytostatic activity—e.g., they are not bactericidal or bacteristatic.

The present inventors have characterized and isolated a natural peptide comprising a sequence selected from the group consisting of YDYNWY (SEQ ID NO: 49), YDYNLY (SEQ ID NO: 50), FDYNFY (SEQ ID NO: 51), FDYNLY (SEQ ID NO: 52), WDYNLY (SEQ ID NO: 53), FDYNWY (SEQ ID NO: 54), YDWNLY (SEQ ID NO: 55), YDWHLY (SEQ ID NO: 56) and YDYSFY (SEQ ID NO: 57) having effective anti-cell aggregate (e.g., anti-biofilm) properties. For example, the peptide may comprise at least one of the following sequences: LFSVPYDYNWYSNWW (SEQ ID NO: 58), LFSVPYDYNWYSNWW (SEQ ID NO: 59), FSVPYDYNLYSNWW (SEQ ID NO: 60), MFSVPYDYNLYSNWV (SEQ ID NO: 61), MFSVPFDYNFYSNWW (SEQ ID NO: 62), LFSVPFDYNFYSNWW (SEQ ID NO: 63), MFSVPFDYNLYSNWW (SEQ ID NO: 64), MFSVPFDYNLYTNWW (SEQ ID NO: 65), MWSVPFDYNLYSNWW (SEQ ID NO: 66), MFSVPFDYNLYKNWL (SEQ ID NO: 67), LFSVPFDYNLYSNWW (SEQ ID NO: 68), LFSIPFDYNLYSNWW (SEQ ID NO: 69), MFSVPWDYNLYKNWL (SEQ ID NO: 70), MFSVPWDYNLYKNWF (SEQ ID NO: 71), MFSVPFFDYNWYSNWW (SEQ ID NO: 72), MASIPYDWNLYQSWA (SEQ ID NO: 73), MASIPYDWNLYSAWA (SEQ ID NO: 74) or MASIPYDWHLYNAWA (SEQ ID NO: 75), or combinations thereof.

The present inventors have characterized and isolated a natural peptide comprising the sequence selected from the group consisting of: FDYDWY (SEQ ID NO: 46), FNFDWY (SEQ ID NO: 48) and FDFDWY (SEQ ID NO: 76), having effective anti-cell aggregate (e.g., anti-biofilm) properties. For example, the peptide may comprise at least one of the following sequences: SFDYDWY (SEQ ID NO: 77), SFDYDWYN (SEQ ID NO: 78), HSFDYDWYN (SEQ ID NO: 79), HSFDYDWYNV (SEQ ID NO: 80), VHSFDYDWYNV (SEQ ID NO: 81), VHSFDYDWYNVS (SEQ ID NO: 82), SVHSFDYDWYNVS (SEQ ID NO: 83), SVHSFDYDWYNVSD (SEQ ID NO: 84), KSVHSFDYDWYNVSD (SEQ ID NO: 85), KSVHSFDYDWYNVSDQ (SEQ ID NO: 86), NKSVHSFDYDWYNVSDQ (SEQ ID NO: 87), NKSVHSFDYDWYNVSDQA (SEQ ID NO: 88), QNKSVHSFDYDWYNVSDQA (SEQ ID NO: 89), QNKSVHSFDYDWYNVSDQAD (SEQ ID NO: 90), SQNKSVHSFDYDWYNVSDQAD (SEQ ID NO: 91), SQNKSVHSFDYDWYNVSDQADL (SEQ ID NO: 92), FSQNKSVHSFDYDWYNVSDQADL (SEQ ID NO: 93), FSQNKSVHSFDYDWYNVSDQADLK (SEQ ID NO: 94), SFSQNKSVHSFDYDWYNVSDQADLK (SEQ ID NO: 95), SFSQNKSVHSFDYDWYNVSDQADLKN (SEQ ID NO: 96), CSFSQNKSVHSFDYDWYNVSDQADLKN (SEQ ID NO: 97) or CSFSQNKSVHSFDYDWYNVSDQADLKNC (SEQ ID NO: 98), or combinations thereof.

The present inventors have characterized and isolated a natural peptide comprising a sequence selected from the group consisting of SVPYDYNWYSNW (SEQ ID NO: 2), SFSQNKSVHSFDYDWYNVSDQADLKN (SEQ ID NO: 96) and SVHSFDYDWYNV (SEQ ID NO: 4).

An exemplary protein or peptide agent derived from an aquatic organism may be used to detach a single cell organism from a surface or from other single cell organisms is equinatoxin. Equinatoxins (i.e., equinatoxins 1, 2 and 3) have pore forming toxins found in sea anemones (e.g., *Actinia equina*). Equinatoxins may be comprised in sea anemone cells or may be isolated therefrom. Any equinatoxin may be used according to the teachings of the present invention for detaching microorganisms from a surface or from each other. One example is the Equinatoxin-2 precursor (GenBank accession identifier >gi|148428895|sp|P61914.11|ACTP2_ACTEQ (Equinatoxin II) (EqT II) (EqTII)):

(SEQ ID NO: 99)
MSRLIIVFIVVTMICSATALPSKKIIDEDEEDEKRSADVAGAVIDGASLS

FDILKTVLEALGNVKRKIAVGVDNESGKTWTALNTYFRSGTSDIVLPHKV

PHGKALLYNGQKDRGPVATGAVGVLAYLMSDGNTLAVLFSVPYDYNWYSN

WWNVRIYKGKRRADQRMYEELYYNLSPFRGDNGWHTRNLGYGLKSRGFMN

SSGHAILEIHVSKA

Another exemplary protein derived from a sea anemone is *Stichodactyla helianthus* ((GenBank accession identifier >gi|2815496|sp|P07845.2|ACTP2_STOHE (Sticholysin II) (StnII) (Cytolysin St II) (Cytolysin III) (Cytotoxin)):

(SEQ ID NO: 100)
ALAGTIIAGASLTFQVLDKVLEELGKVSRKIAVGIDNESGGTWTALNAYF

RSGTTDVILPEFVPNTKALLYSGRKDTGPVATGAVAAFAYYMSSGNTLGV

MFSVPFDYNWYSNWWDVKIYSGKRRADQGMYEDLYYGNPYRGDNGWHEKN

LGYGLRMKGIIVITSAGEAKMQIKISR

An exemplary protein derived from bony fish is *Danio rerio* ((GenBank accession identifier >gi|125821212|ref|XP_001342650.1|PREDICTED (*Danio rerio*)):

(SEQ ID NO: 101)
MTESAEAVAANVSSRRHATVEITNLTNNYCFLNPKVYLENGETSNPPQPT

VRPLKTEVCTFSKSAAHATGSVGVLTYDLFERRRNDYTETLAIMFSVPWD

YNLYKNWFAVGIYPKGKECDQALYKEMYYQKNQHGFVREEANGSGINFEG

KNLDIRATMCPMGRAIVKVEVWDKLLSPMAQMDC

Another exemplary protein derived from bony fish is *Tetradodon nigroviridis* ((GenBank accession identifier >gi|47218822|emb|CAG02807.1|unnamed protein product (*Teraodon nigroviridis*)):

(SEQ ID NO: 102)
MESAEAVAADVSRSRSVTIEISNLTKNYCLINPRVYLESGETYNPPQPTV

RPLMTEVCTFSKSSGIPTGSVGVLTYELLERRSTMLPETLAIMFSVPYDY

SFYNNWFAVGIYETGTKCNEGLYKQMYNEKKQAEHGFVREKANGSGINYV

GGNLDIRATMNPLGKAIMKVEVWDAFFPFSE

An exemplary protein derived from moss is *Physcomitrella patens* ((GenBank accession identifier >gi|16806023|ref|XP_001782104.1|predicted protein (*Physcomitrella patens* subsp. *patens*)):

(SEQ ID NO: 103)
MVVHLIAMGLRYSETIMKTARMAEAIIPAAELSIKTLQNIVEGITGVDRK

IAIGFKNLTDYTLENLGVYFNSGSSDRSIAYKINAQEALLFSARKSDHTA

RGTVGTFSYYIQDEDKTVHVMWSVPFDYNLYSNWWNIAVVDGRQPPDSNV

HDNLYNGSGGMPYPNKPDQYINNEQKGFHLFGSMTNNGQATIEVELKKA

An exemplary protein derived from birds is *Gallus gallus* (GenBank accession identifier >gi|118129726|ref|XP_001231839.1|PREDICTED: hypothetical protein isoform (*Gallus gallus*)):

(SEQ ID NO: 104)
MPPKEKKENDKPCNDNCQPKPQGKGVESLMKNIDVCRSVGLEIINRTRTV

TLTDFRSYCFSGKIVTTLPFEIGPDSKGICIFAKTPYSLRGSVGTVVCKA

DTFFLAITFSNPYDYILYKIEFALEIFTEPNHLGNLGDVFSKMMKSKPYC

GSSLFQRAVLESEHETLEVSKGSIRVQAKMSNNRKAILKVQVEDMDPPPY

SKGM

An exemplary protein derived from a platypus is *Ornithorhynchus anatinus* (GenBank accession identifier >gi|149638239|ref|XP_001512702.1|PREDICTED: integral membrane protein GPR137B-like (*Ornithorhynchus anatinus*)):

(SEQ ID NO: 105)
MEGSPPGRPPGNDSLPPTLSPAVPPYVKLGLTSVYTAFYSLLFVFVYAQL

WLVLHHRHRRLSYQTVFLFLCLLWAALRTVLFSFYFRDFLAANKLGPFGF

WLLYCCPVCLQFFTLTLMNLYFSQVIFKAKSKFSPELLKYRLALYLASLV

VSLVFLLVNLTCAVLVKTGTWERKVVVSVRVAINDTLFVLCAVSLSVCLY

KISKMSLANIYLESKGSSVCQVTAIGVTVILLYASRACYNLFTLSFSRHG

SSFDYDWYNVSDQADLKSQLGDAGYVVFGVVLFVWELLPTSLVVYFFRVR

NPTKDPTNPRGVPSHAFSPRSYFFDNPRRYDSDDDLAWNVAPQGFQGSFA

PDYYDWGQPSSSFTGHIGSLQQDSDLDNGKPSHA

An example of an applicable peptide derived from equinatoxin is SVPYDYNWYSNW (SEQ ID NO: 2), in either soluble form or conjugated to polyethylene glycol (PEG) and palmitic acid and capable of adhering to a surface. The soluble and conjugated form of the peptide in cyclic form and having a cysteine at each of the N- and C-terminal ends are as follows:

Eqt2ZCyc (soluble aquatic peptide):
(SEQ ID NO: 106)
CSVPYDYNWYSNWC

Eqt2ZCyc-3PEG-Pal (adhesive aquatic peptide):
Pal--(miniPEG)3-
(SEQ ID NO: 107)
CSVPYDYNWYSNWC Peptides based on a subset of equinatoxin sequences and variants thereof are also applicable. The chart below demonstrates specific 12-mer peptide embodiments, with applicable amino acids for each of the 12 positions. Bolded amino acids correspond to amino acids not naturally occurring at the corresponding positions, but which provide for peptides falling within the scope of the present invention. In some embodiments, the peptide is not SVPYDYNWYSNW (SEQ ID NO: 2).

| | 1 | 2 | 3 | 4 | 5 | 6 | 7 | 8 | 9 | 10 | 11 | 12 |
|---|---|---|---|---|---|---|---|---|---|---|---|---|
| Equinatoxin (SEQ ID NO: 1) | S | V | P | Y | D | Y | N | W | Y | S | N | W |
| | N | I | | F | N | F | S | L | N | K | E | R |
| | I | A | | W | Q | R | G | F | F | N | D | V |
| | V | N | | | E | W | D | M | K | T | Q | L |
| | R | L | | | | | H | S | L | E | S | I |
| | K | Q | | | | | E | T | R | R | A | K |
| | Q | | | | | | L | Q | I | L | I | F |
| | L | | | | | | K | A | V | Q | | E |
| | | | | | | | I | G | W | I | | |
| | | | | | | | | V | Q | V | | |
| | | | | | | | | P | | D | | |
| | | | | | | | | Y | | K | | |
| | | | | | | | | I | | | | |
| | | | | | | | | K | | | | |

An exemplary peptide agent may be derived from a human. For example, a peptide derived from GPCR137b (GPR137B (TM7SF1)) may be used to detach a single cell organism from a surface or from other single cell organisms. GPCR137b can be found in human kidney, heart, brain, and placenta tissue. [Spangenberg et al., Genomics. 1998 Mar. 1; 48(2):178-85; Bjarnadottir et al., Genomics, 88(3): 263-273 (2006)]. Peptides SFSQNKSVHSFDYDWYN-VSDQADLKN (SEQ ID NO: 96) and SVHSFDYDWYNV (SEQ ID NO: 4), as cyclic peptides with cysteine attached to both the C- and N-terminals of the peptides in either soluble form or conjugated to polyethylene glycol and palmitic acid and capable of adhering to a surface, are two examples of applicable peptides derived from human GPCR137b:

cable amino acids for each of the 12 positions. Bolded amino acids correspond to amino acids not naturally occurring at the corresponding positions, but which provide for peptides falling within the scope of the present invention. In some embodiments, the peptide is not SVHSFDYDWYNV (SEQ ID NO: 4).

| | 1 | 2 | 3 | 4 | 5 | 6 | 7 | 8 | 9 | 10 | 11 | 12 |
|---|---|---|---|---|---|---|---|---|---|---|---|---|
| GPCR137B (SEQ ID NO: 3) | S | V | H | S | F | D | Y | D | W | Y | N | V |
| | N | I | N | P | W | N | F | G | F | F | Q | I |
| | T | L | Q | A | Y | E | W | E | Y | W | | L |
| | K | Y | E | T | | Q | | | | | | |
| | R | G | D | | | | | | | | | |
| | H | F | S | | | | | | | | | |
| | E | W | | | | | | | | | | |
| | I | | | | | | | | | | | |
| | Q | | | | | | | | | | | |
| | D | | | | | | | | | | | |

```
grZ28Cyc (soluble long human peptide):
                              (SEQ ID NO: 98)
CSFSQNKSVHSFDYDWYNVSDQADLKNC grZ28Cyc-3PEG-Pal (adhesive long human peptide):
Palmitoyl-(miniPEG)3-
                              (SEQ ID NO: 108)
CSFSQNKSVHSFDYDWYNVSDQADLKNC grZ14s-nvCyc (soluble short human peptide):
                              (SEQ ID NO: 109)
CSVHSFDYDWYNVC grZ14s-nvCyc-3PEG-Pal (adhesive short human
peptide): Pal--(miniPEG)3-
                              (SEQ ID NO: 110)
CSVHSFDYDWYNVC
```

Peptides based on a subset of GPCR137b sequences and variants thereof are also applicable. The chart below demonstrates specific 12-mer peptide embodiments, with appli- An exemplary peptide derived from *Physcomitrella patens* (moss) is SVPFDYNLYSNW (SEQ ID NO: 111). This same sequence can also be found in *Selaginella moellendorffii* (Genbank Accession No: XP_002963283), a type of plant, and in the following sea anemones: *Phyllodiscus semoni* (Genbank Accession No: BAI70365); *Heteractis crispa* (Genbank Accession No: AAW47930); and *Actineria villosa* (Genbank Accession No: BAD74019). The cyclicized form of the peptide is as follows:

```
Physco-Cyc:
                              (SEQ ID NO: 112)
CSVPFDYNLYSNWC
```

EXAMPLES

Example 1

Detaching Overnight Biofilm with Overnight Eqt2Z-cyc Incubation

A biofilm was created by incubating *Pseudomonas aeruginoas* (ATCC 27853) overnight in wells at 37° C., allowing the microorganism to attach to the well surface. Eqt2Z-cyc peptide [Custom Peptide Synthesis; Peptron, Korea] at different concentrations was subsequently added to the wells and allowed to incubate overnight. The P.a. control was *Pseudomonas aeruginoas* alone. FIG. 1 demonstrates that Eqt2Z-cyc peptides caused far greater microorganism detachment than in the P.a. control.

Example 2

Detaching 2-Hour Biofilm with Overnight Eqt2Z-cyc Incubation

Figure 2A:
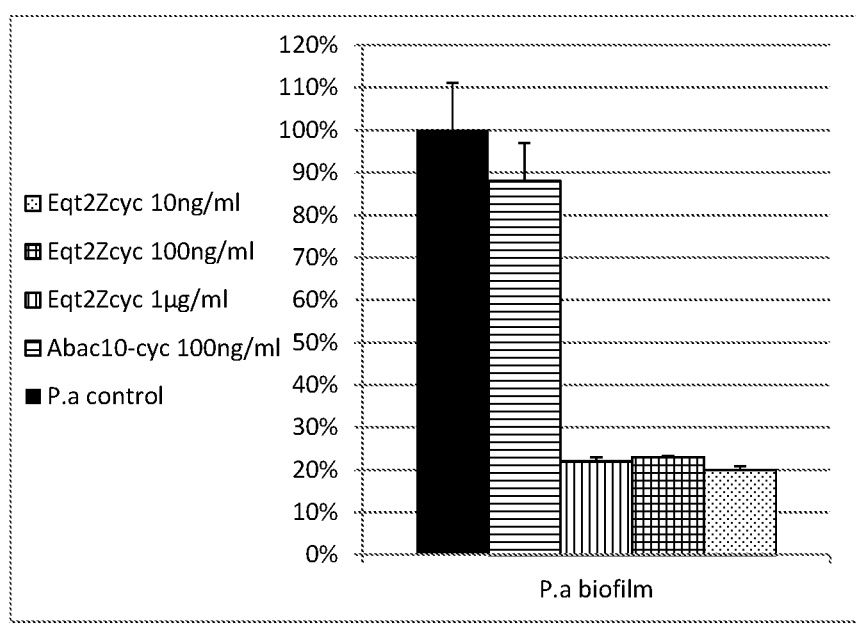
FIG. 2A shows the detachment of *Pseudomonas aeruginoas* biofilm from a well after incubating the microorganism for 2 hours to create the biofilm and subsequently incubating the biofilm with different concentrations of Eqt2Z-cyc peptide and Abac10 negative control overnight.

A biofilm was created by culturing *Pseudomonas aeruginoas* (ATCC 27853) for 2 hours in a well at 37° C. Eqt2Z-cyc peptide at different concentrations was subsequently added to the well and allowed to incubate overnight. The Abac10-cyc peptide served as a negative control. The P.a. control was *Pseudomonas aeruginoas* alone. FIG. 2A demonstrates that Eqt2Z-cyc peptides caused far greater microorganism detachment than in the P.a. control or negative control.

Example 3

Detaching 2-Hour Biofilm with 24-hour Eqt2Z-cyc Incubation

Figure 2B:
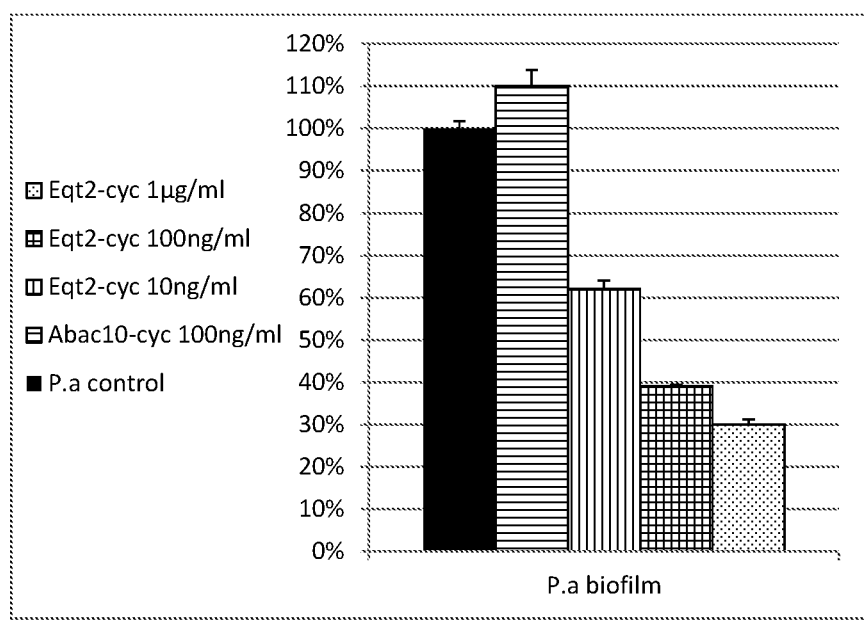
FIG. 2B shows the detachment of *Pseudomonas aeruginoas* biofilm from a well after incubating the microorganism for 2 hours to create the biofilm and subsequently incubating the biofilm with different concentrations of Eqt2Z-cyc peptide and Abac10 negative control for 24 hours.

A biofilm was created by culturing *Pseudomonas aeruginoas* (ATCC 27853) for 2 hours in a well at 37° C. Eqt2Z-cyc peptide at different concentrations was subsequently added to the well and allowed to incubate for 24 hours. The Abac10-cyc peptide served as a negative control. The P.a. control was *Pseudomonas aeruginoas* alone. FIG. 2B demonstrates that Eqt2Z-cyc peptides caused far greater microorganism detachment than in the P.a. control or negative control. Staining was performed with crystal violet at OD 595 nm.

Example 4

Detaching 2-Hour Biofilm with 24-hour grZ14s-nyCyc Incubation

Figure 3:
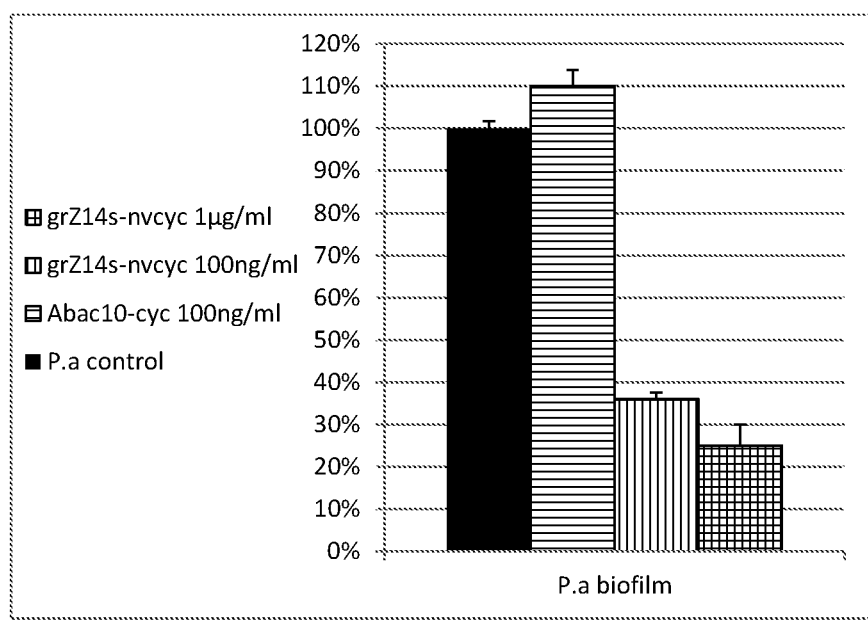
FIG. 3 shows the detachment of *Pseudomonas aeruginoas* biofilm from a well after incubating the microorganism for 2 hours to create the biofilm and subsequently incubating the biofilm with grZ14s-nvcyc peptide overnight.

A biofilm was created by culturing *Pseudomonas aeruginoas* (ATCC 27853) for 2 hours in a well at 37° C. grZ14s-nvCyc peptide [Custom Peptide Synthesis; Peptron, Korea] at different concentrations was subsequently added to the well and allowed to incubate for 24 hours. The Abac10-cyc peptide served as a negative control. The P.a. control was *Pseudomonas aeruginosa* alone. FIG. 3 demonstrates that grZ14s-nyCyc peptides caused far greater microorganism detachment than in the P.a. control or negative control. Staining was performed with crystal violet at OD 595 nm.

Example 5

Detaching 24-Hour Biofilm with 24-hour Eqt2Z-cyc Incubation

Figure 4:
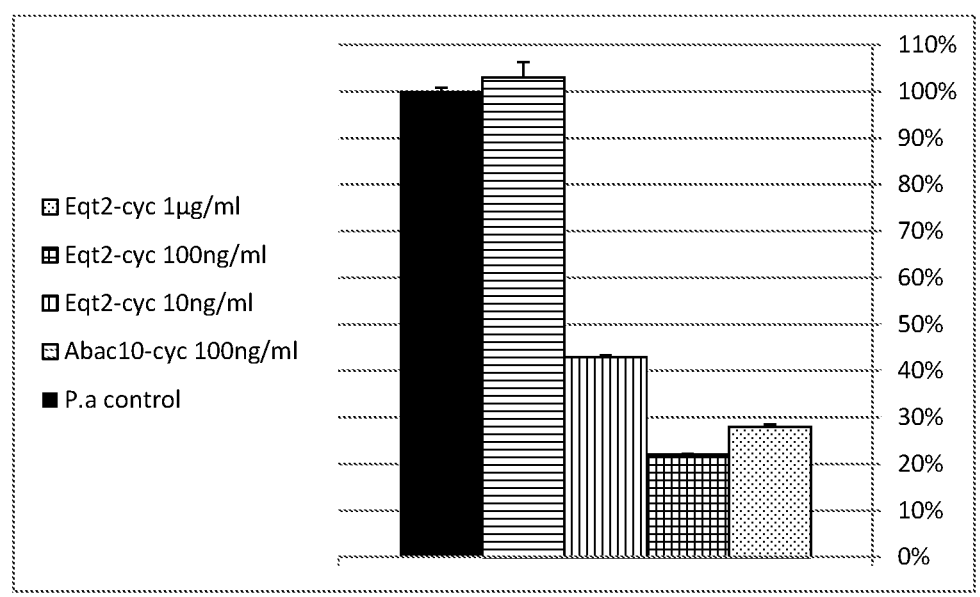
FIG. 4 shows the detachment of *Pseudomonas aeruginoas* biofilm from a well after incubating the microorganism for 24 hours to create the biofilm and subsequently incubating the biofilm with Eqt2-cyc peptide for 24 hours.

A biofilm was created by culturing *Pseudomonas aeruginoas* (ATCC 27853) for 24 hours in a well at 37° C. Eqt2Z-cyc peptide at different concentrations was subsequently added to the well and allowed to incubate for 24 hours. The Abac10-cyc peptide served as a negative control. The P.a. control was *Pseudomonas aeruginoas* alone. FIG. 4 demonstrates that Eqt2Z-cyc peptides caused far greater microorganism detachment than in the P.a. control or negative control. Staining was performed with crystal violet at OD 595 nm.

Example 6

Detaching 24-Hour Biofilm with 24-hour grZ14s-nyCyc

Figure 5:
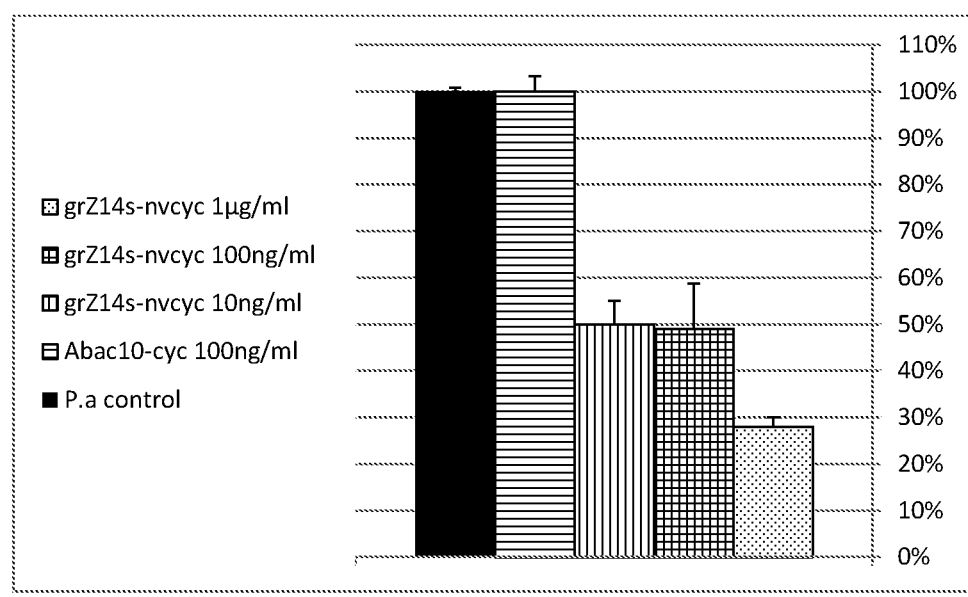
FIG. 5 shows the detachment of *Pseudomonas aeruginoas* biofilm from a well after incubating the microorganism for 24 hours to create the biofilm and subsequently incubating the biofilm with grZ14s-nvcyc peptide for 24 hours.

A biofilm was created by culturing *Pseudomonas aeruginoas* (ATCC 27853) for 24 hours in a well at 37° C. grZ14s-nyCyc peptide at different concentrations was subsequently added to the well and allowed to incubate for 24 hours. The Abac10-cyc peptide served as a negative control. The P.a. control was *Pseudomonas aeruginoas* alone. FIG. 5 demonstrates that grZ14s-nvCyc peptides caused far greater microorganism detachment than in the P.a. control or negative control. Staining was performed with crystal violet at OD 595 nm.

Example 7

Detaching 24-Hour Biofilm with Overnight PhyscoZ-Cyc

Figure 6:
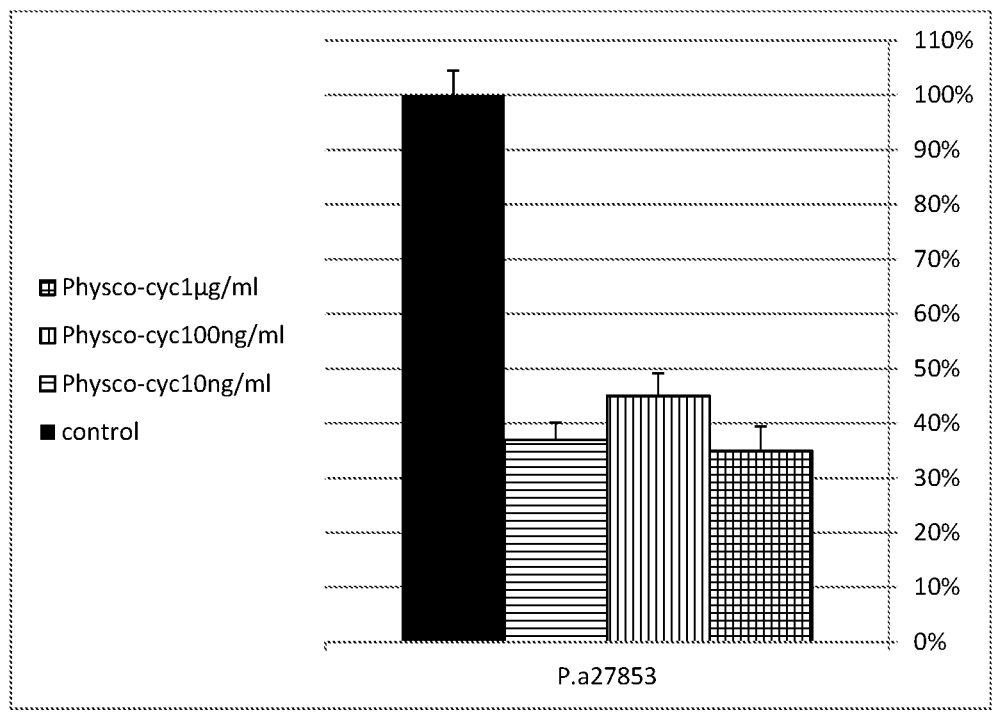
FIG. 6 shows the detachment of *Pseudomonas aeruginoas* biofilm from a well after incubating the microorganism for 24 hours to create the biofilm and subsequently incubating the biofilm with Physco-cyc peptide overnight.

A biofilm was created by culturing *Pseudomonas aeruginoas* (ATCC 27853) for 24 hours in a well at 37° C. PhyscoZ-Cyc peptide [Custom Peptide Synthesis; Peptron, Korea] at different concentrations was subsequently added to the well and allowed to incubate for 24 hours. The P.a. control was *Pseudomonas aeruginoas* alone. FIG. 6 demonstrates that PhyscoZ-Cyc peptides caused far greater microorganism detachment than in the P.a. control. Staining was performed with crystal violet at OD 595 nm.

Example 8 grZ14s-nyCyc Enhances Antibiotic Activity of Imipenem and Ampicillin

The ability of grZ14s-nyCyc to enhance the activity of Imipenem or Ampicillin was performed by first incubating the wells in a 96-well plate with *Pseudomonas aeruginoas* for 24 hours at 37° C. and 50 rpm shaking. The plate was washed 2 times with phosphate buffer solution. The wells were then filled with either the antibiotic alone or the antibiotic with grZ14s-nvCyc (100 ng/ml). The wells were then incubated for 48 hours (24 hours for Ampicillin) at 37° C. and 50 rpm shaking. 0.3% triton X-100 and 0.45% EDTA were then added to the wells, bringing the wells to a final concentration of 0.075% triton X-100 and 0.1125% EDTA. The plates were then sonicated in a bath-sonicator for 12 minutes. The wells were then serially diluted in PBS. The solutions were then seeded on a blood plate agar and incubated at 37° C. for 24 hours.

Figure 7:
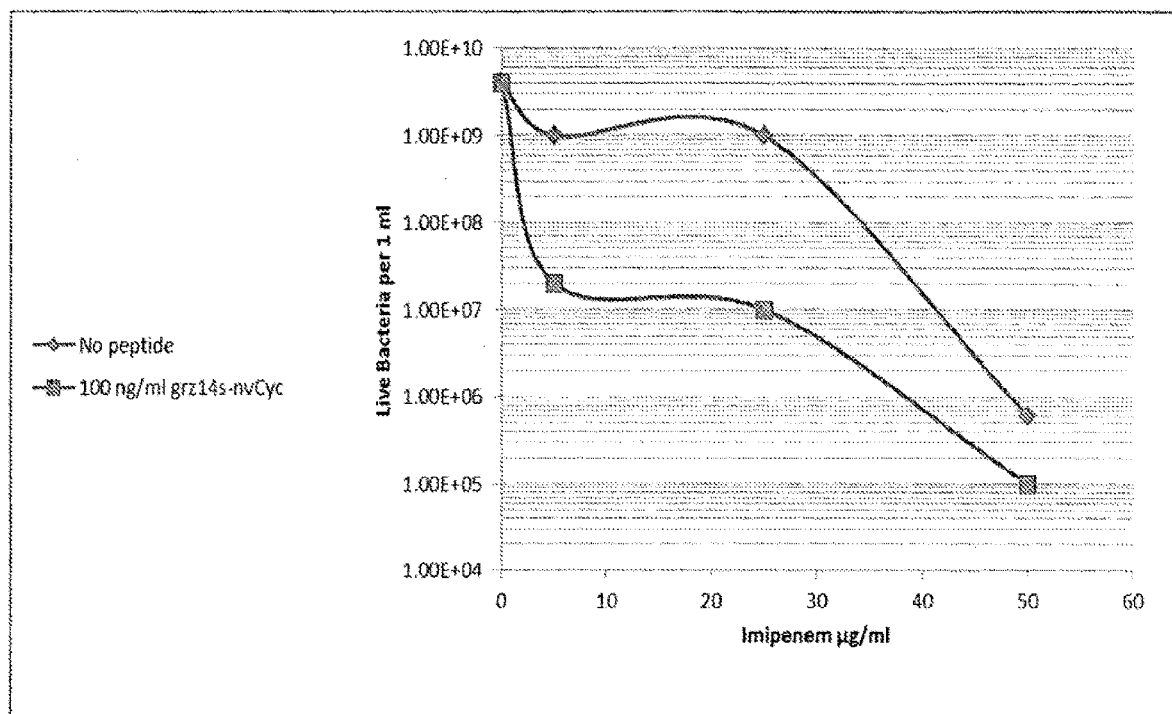
FIG. 7 shows the enhancement of Imipenem activity with grZ14s-nyCyc.
Figure 8:
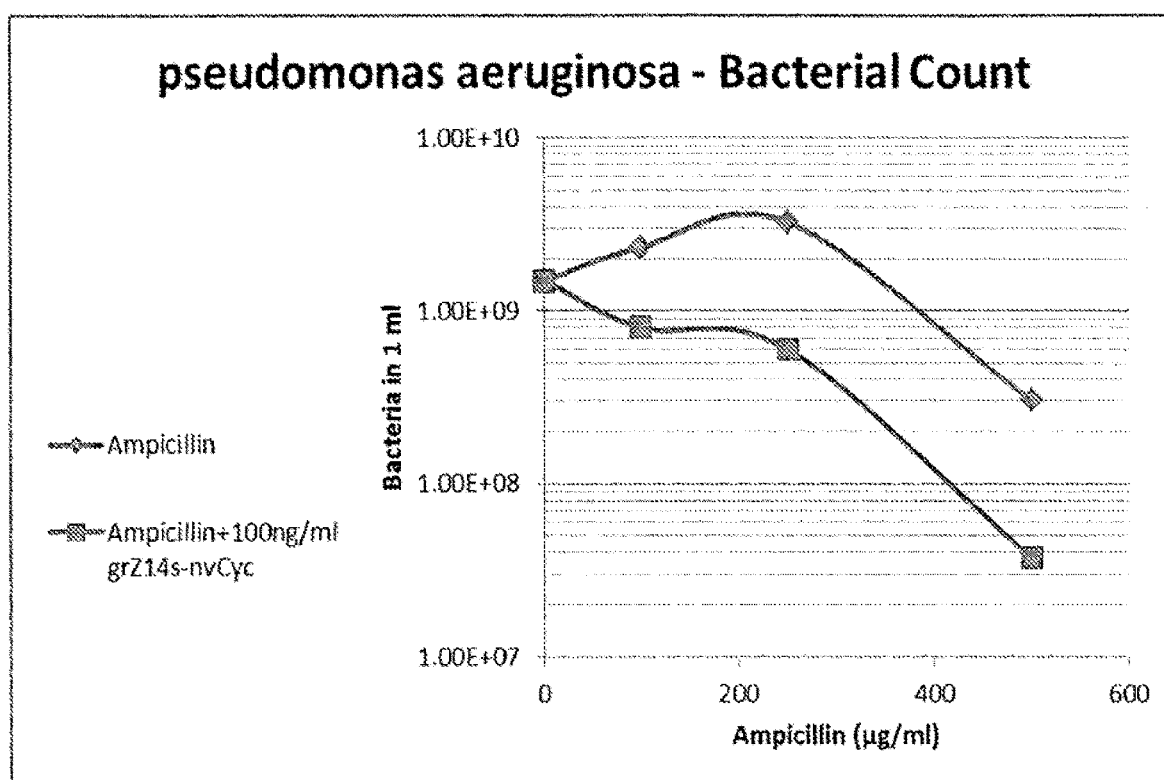
FIG. 8 shows the enhancement of Ampicillin activity with grZ14s-nyCyc.

The results are presented in FIGS. 7 and 8. As FIG. 7 demonstrates, the number of live bacteria was much lower in wells with grZ14s-nyCyc and Imipenem than in wells with Imipenem alone, thereby demonstrating that grZ14s-nvCyc enhances the activity of the antibiotic. FIG. 8 demonstrates that the number of live bacterial is much lower in wells with grZ14s-nvCyc and Ampicillin than in wells with Ampicillin alone, thereby demonstrating that grZ14s-nvCyc enhances the activity of the antibiotic.

Example 9 grZ14s-nyCyc Enhances Antibiotic Activity of Vancomycin

The ability of grZ14s-nyCyc to enhance the activity of Vancomycin was performed by first incubating the wells in a 96-well plate with *Staphylococcus aureus* for 24 hours at 37° C. and 50 rpm shaking. The plate was washed 2 times with phosphate buffer solution. The wells were then filled with either the antibiotic alone or the antibiotic with grZ14s-nyCyc (100 ng/ml). The wells were then incubated for 24 hours at 37° C. and 50 rpm shaking. 0.3% triton X-100 and 0.45% EDTA were then added to the wells, bringing the wells to a final concentration of 0.075% triton X-100 and 0.1125% EDTA. The plates were then sonicated in a bath-sonicator for 12 minutes. The wells were then serially diluted in PBS. The solutions were then seeded on a blood plate agar and incubated at 37° C. for 24 hours.

Figure 9:
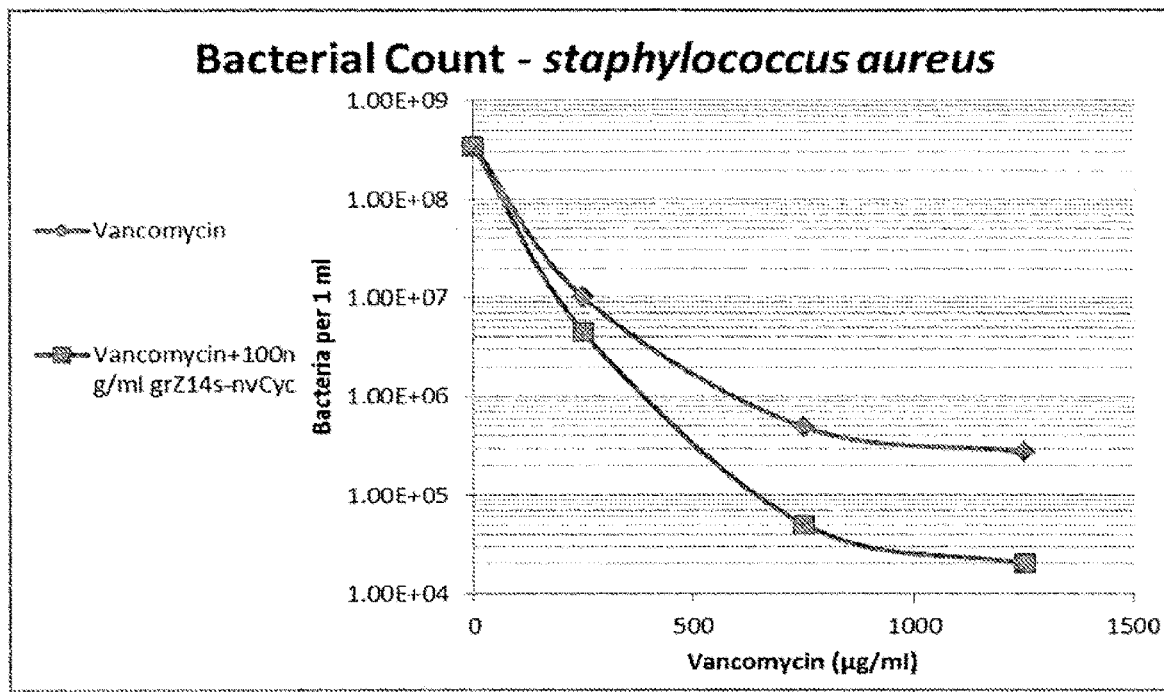
FIG. 9 shows the enhancement of Vancomycin activity with grZ14s-nvCyc.

The results are presented in FIG. 9. As the demonstrates, the number of live bacteria was much lower in wells with grZ14s-nvCyc and Vancomycin than in wells with Vancomycin alone, thereby demonstrating that grZ14s-nyCyc enhances the activity of the antibiotic.

Example 10 grZ14s-nyCyc Enhances Antifungal Activity of Amphotericin

The ability of grZ14s-nyCyc to enhance the activity of Amphotericin was performed by first incubating the wells in a 96-well plate with *Candida albicans* for 24 hours at 37° C. and 50 rpm shaking. The plate was washed 2 times with phosphate buffer solution. The wells were then filled with either the antifungal alone or the antifungal with grZ14s-nyCyc (100 ng/ml). The wells were then incubated for 24 hours at 37° C. and 50 rpm shaking. The plates were again washed 2 times with PBS. BacTiter-Glo Microbial Cell Viability Assay (Promega, USA) was used following the manufacturer protocol and luminescence read.

Figure 10:
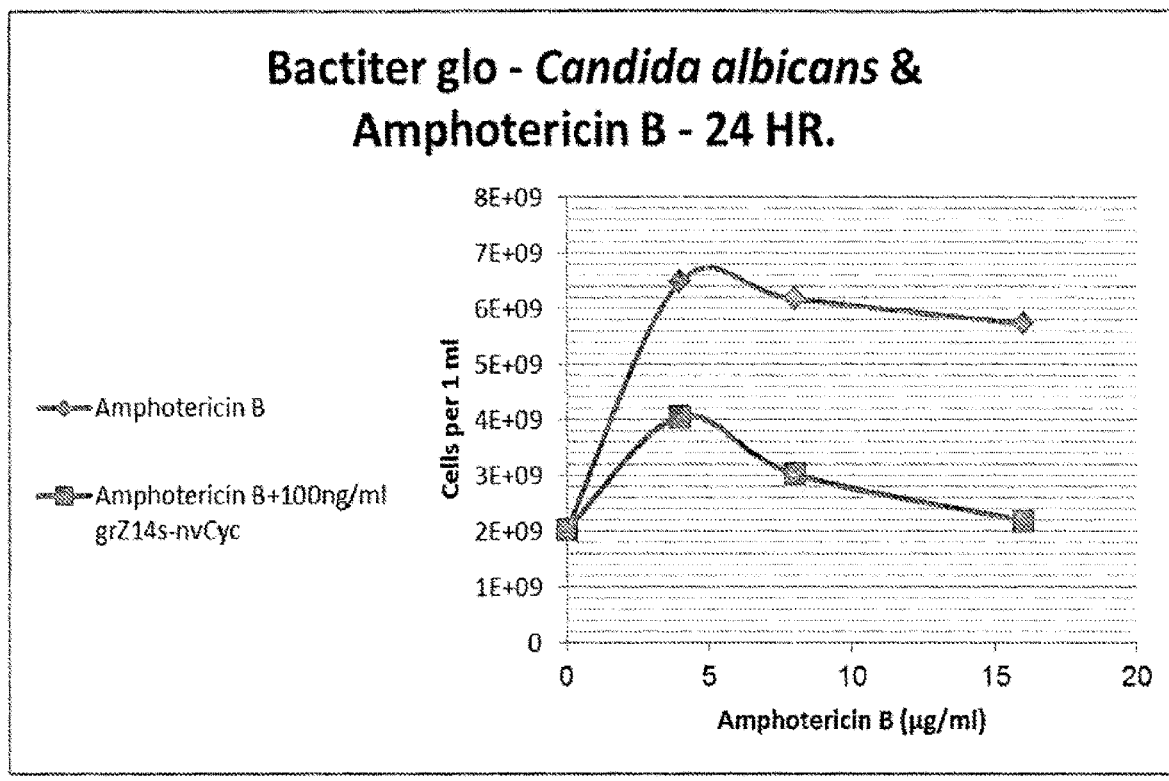
FIG. 10 shows the enhancement of Amphotericin activity with grZ14s-nyCyc.

The results are presented in FIG. 10. As the demonstrates, the number of live fungus was much lower in wells with grZ14s-nvCyc and Amphotericin than in wells with Amphotericin alone, thereby demonstrating that grZ14s-nyCyc enhances the activity of Amphotericin.

Example 11 grZ14s-nyCyc Enhances Antifungal Activity of Fluconazole

The ability of grZ14s-nyCyc to enhance the activity of Fluconazole was performed by first incubating the wells in a 96-well plate with *Candida albicans* for 24 hours at 37° C. and 50 rpm shaking. The plate was washed 2 times with phosphate buffer solution. The wells were then filled with either the antifungal alone or the antifungal with grZ14s-nyCyc (100 ng/ml). The wells were then incubated for 24 hours at 37° C. and 50 rpm shaking. The plates were again washed 2 times with PBS. BacTiter-Glo Microbial Cell Viability Assay (Promega, USA) was used following the manufacturer protocol and luminescence read.

Figure 11:
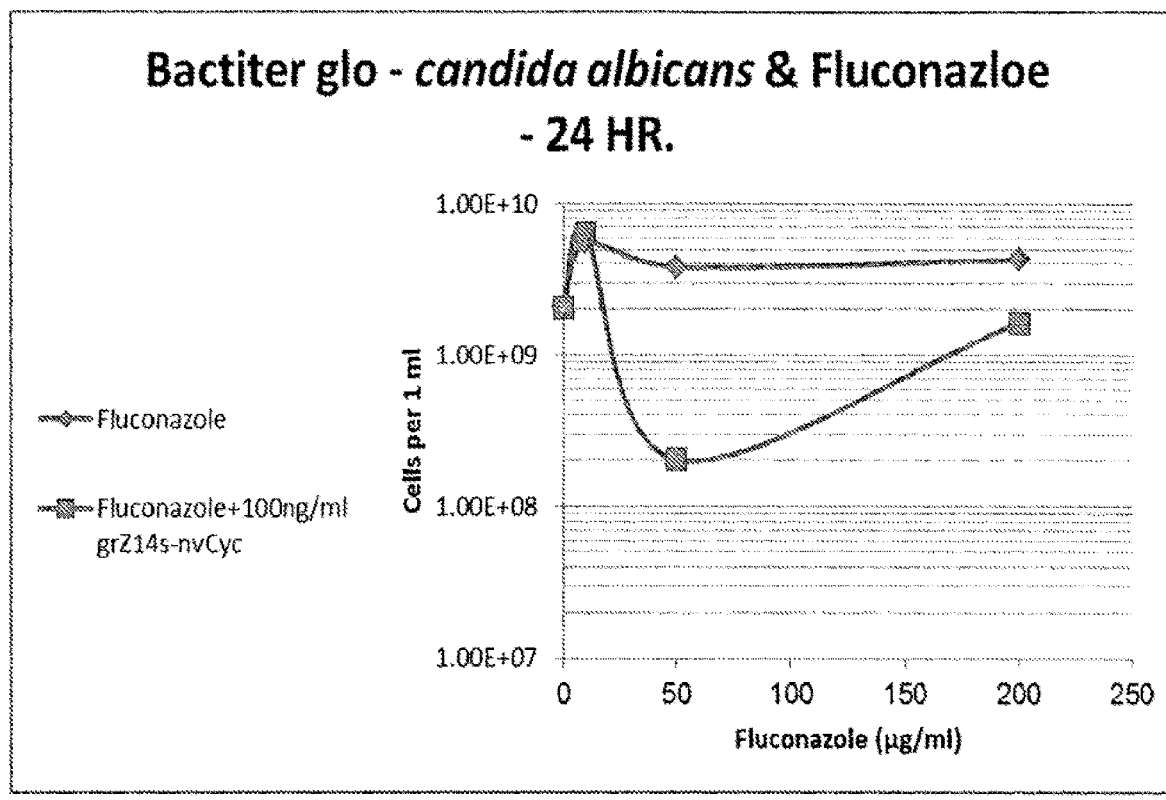
FIG. 11 shows the enhancement of Fluconazole activity with grZ14s-nvCyc

The results are presented in FIG. 11. As the demonstrates, the number of live fungus was much lower in wells with grZ14s-nvCyc and Fluconazole than in wells with Fluconazole alone, thereby demonstrating that grZ14s-nyCyc enhances the activity of Fluconazole.

Example 12 grZ14s-nyCyc Enhances Antibiotic Activity of Kanamycin

The ability of grZ14s-nyCyc to enhance the activity of Kanamycin was performed by first incubating the wells in a 96-well plate with *Pseudomonas aeruginoas* for 24 hours at 37° C. and 50 rpm shaking. The plate was washed 2 times with phosphate buffer solution. The wells were then filled with either Kanamycin alone or Kanamycin with grZ14s-nyCyc (100 ng/ml). The wells were then incubated for 24 hours at 37° C. and 50 rpm shaking. The plates were again washed 2 times with PBS. BacTiter-Glo Microbial Cell Viability Assay (Promega, USA) was used following the manufacturer protocol and luminescence read.

Figure 12:
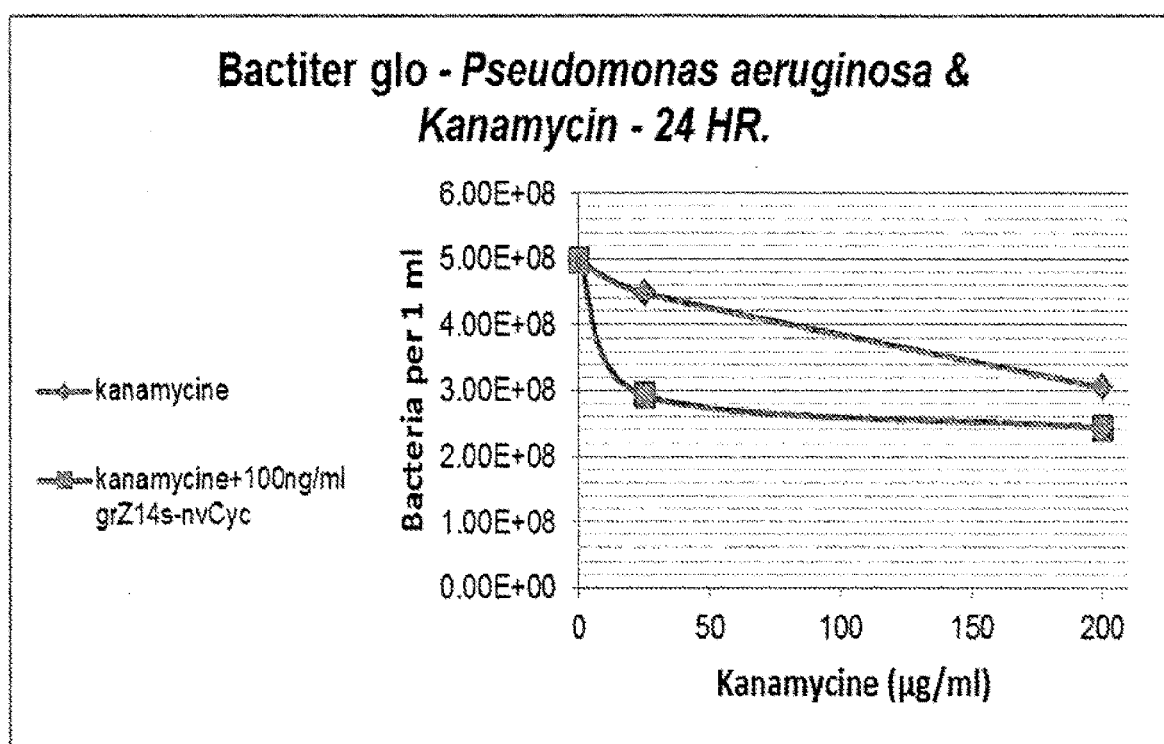
FIG. 12 shows the enhancement of Kanamycin activity with grZ14s-nyCyc
Figure 13A:
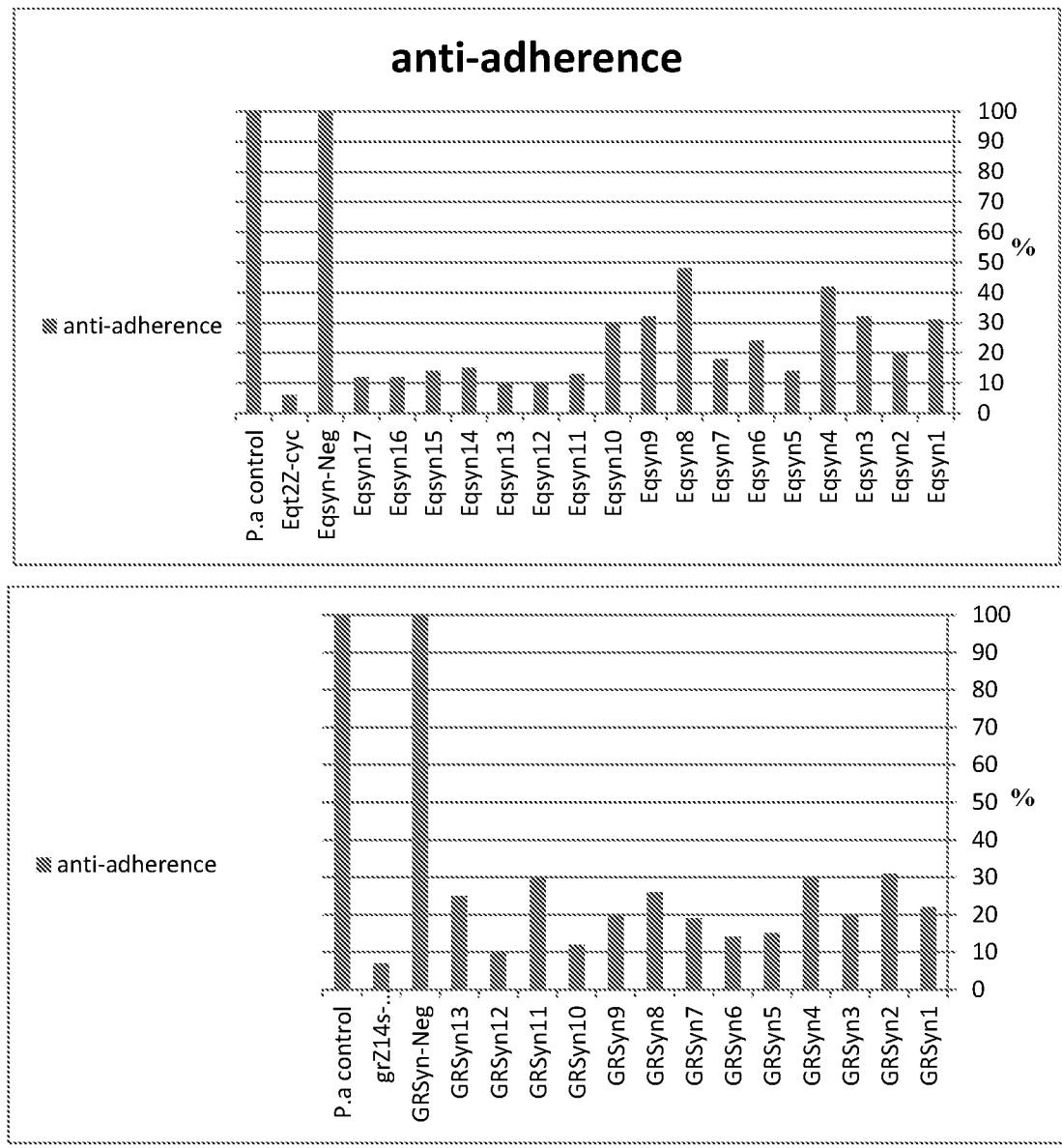
FIG. 13A shows the prevention of *Pseudomonas aeruginoas* adherence by various peptides.
Figure 13B:
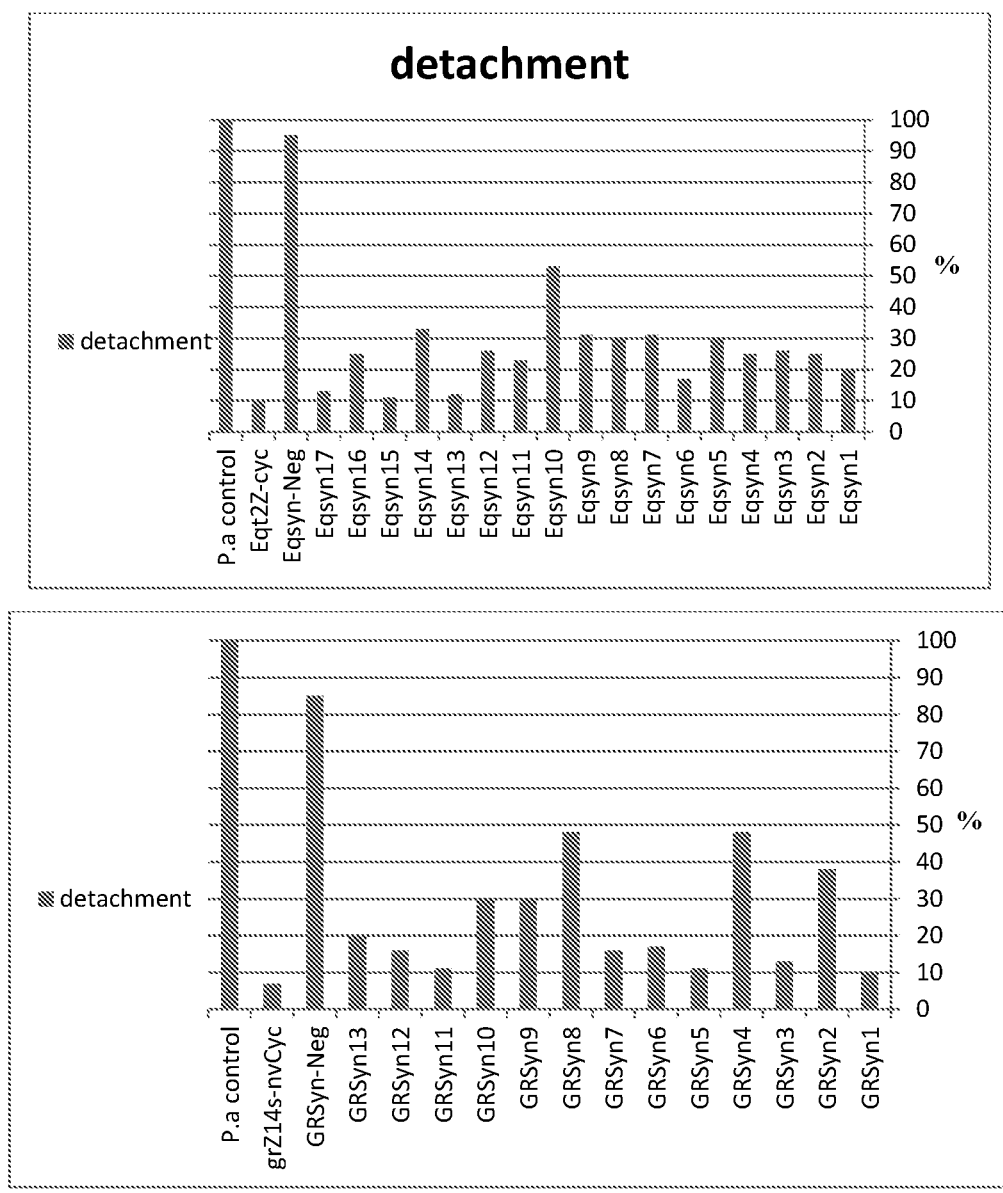
FIG. 13B shows the detachment of *Pseudomonas aeruginoas* adherence by various peptides.
Figure 14A:
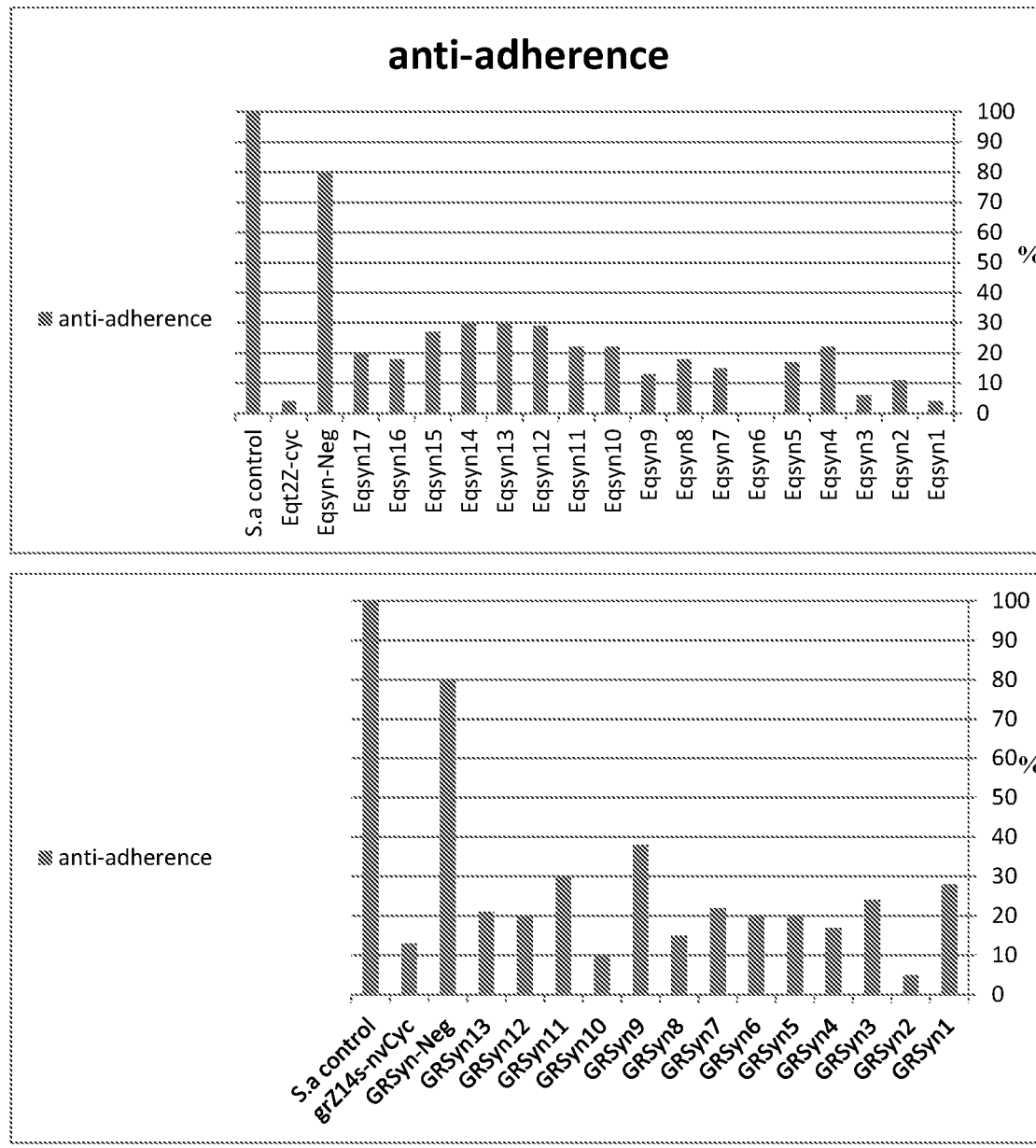
FIG. 14A shows the prevention of *Staphylococcus aureus* adherence by various peptides.
Figure 14B:
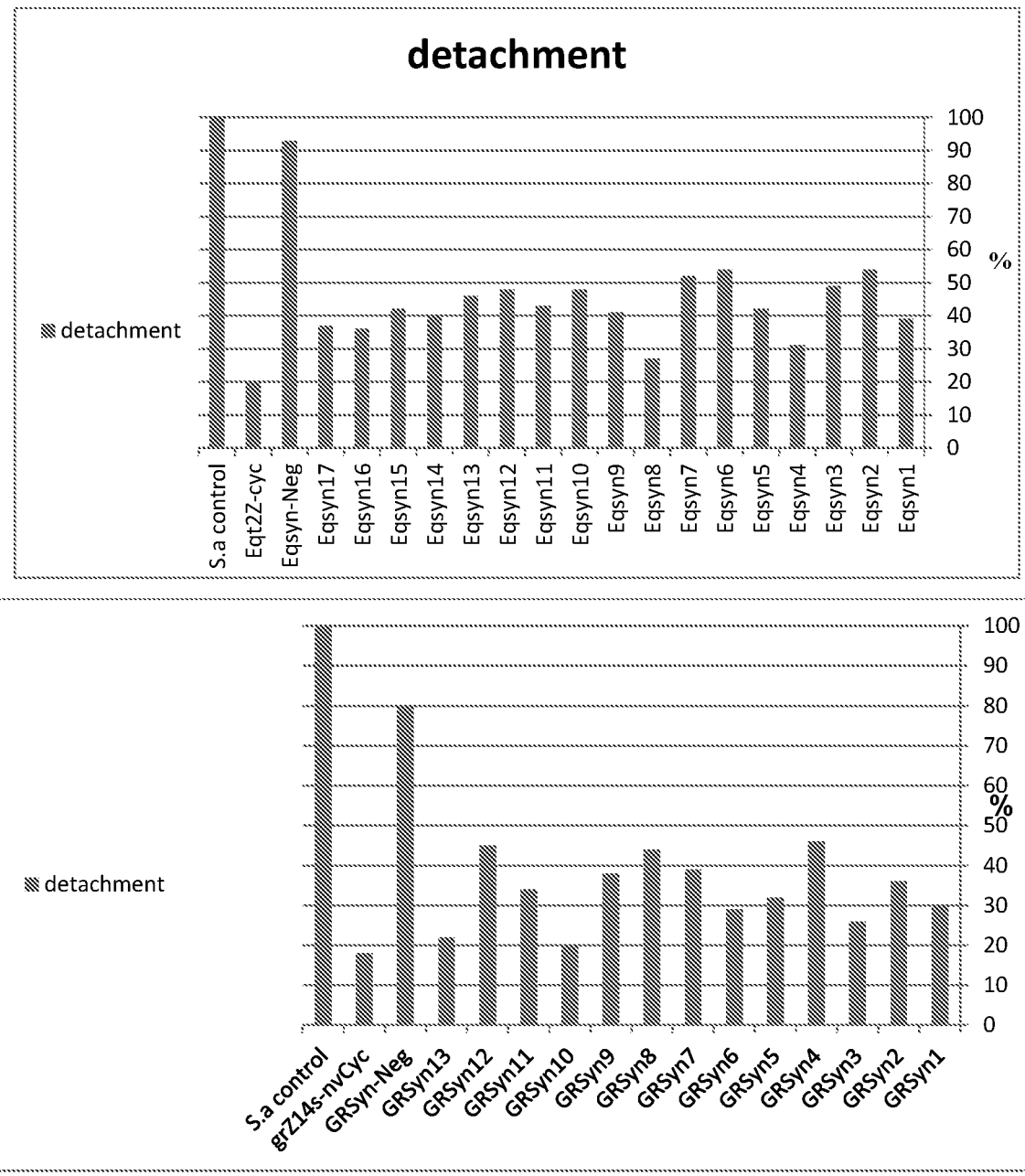
FIG. 14B shows the detachment of *Staphylococcus aureus* adherence by various peptides.
Figure 15A:
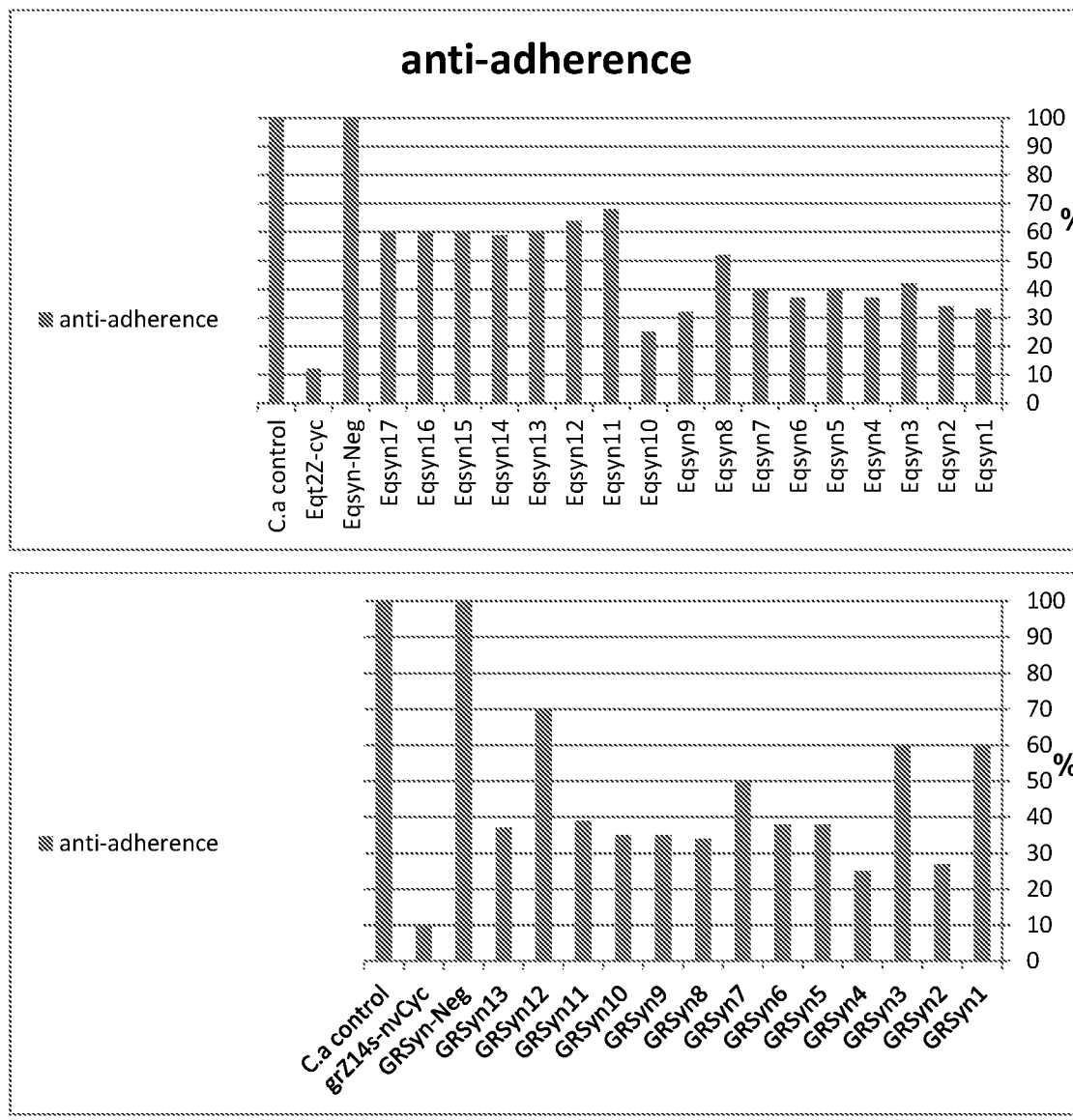
FIG. 15A shows the prevention of *Candida albicans* adherence by various peptides.
Figure 15B:
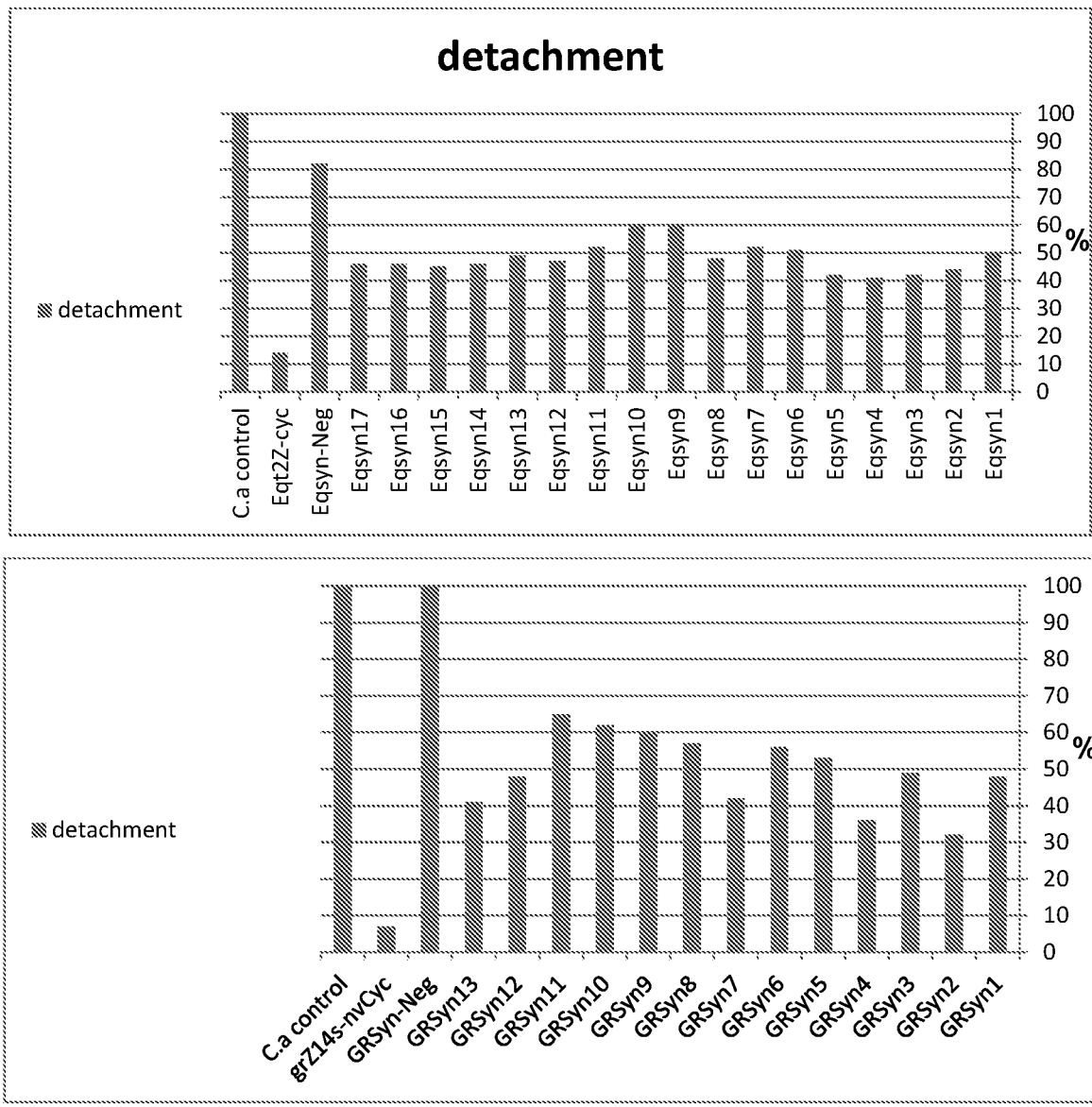
FIG. 15B shows the detachment of *Candida albicans* adherence by various peptides.
Figure 16A:
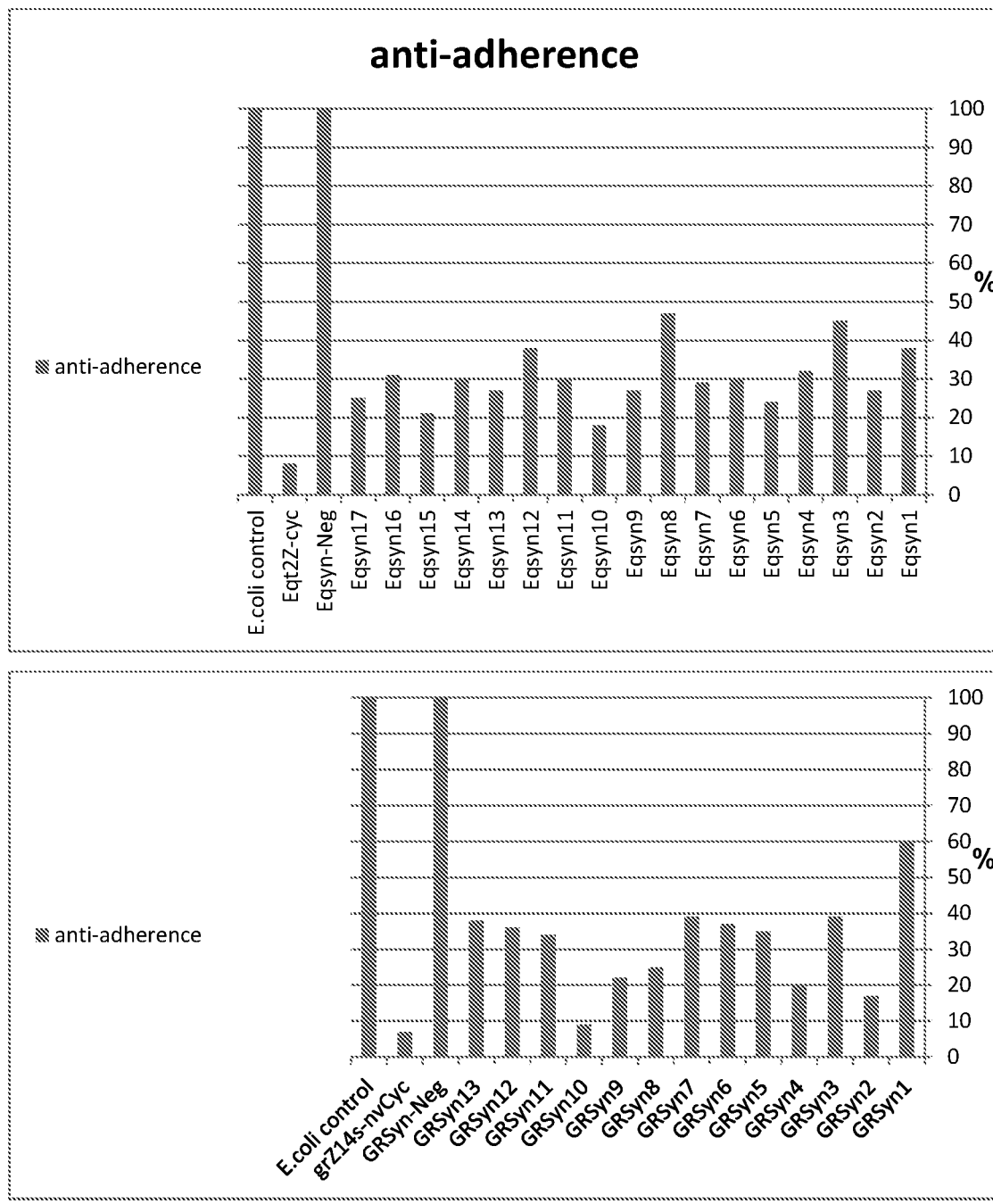
FIG. 16A shows the prevention of *Escherichia coli* adherence by various peptides.
Figure 16B:
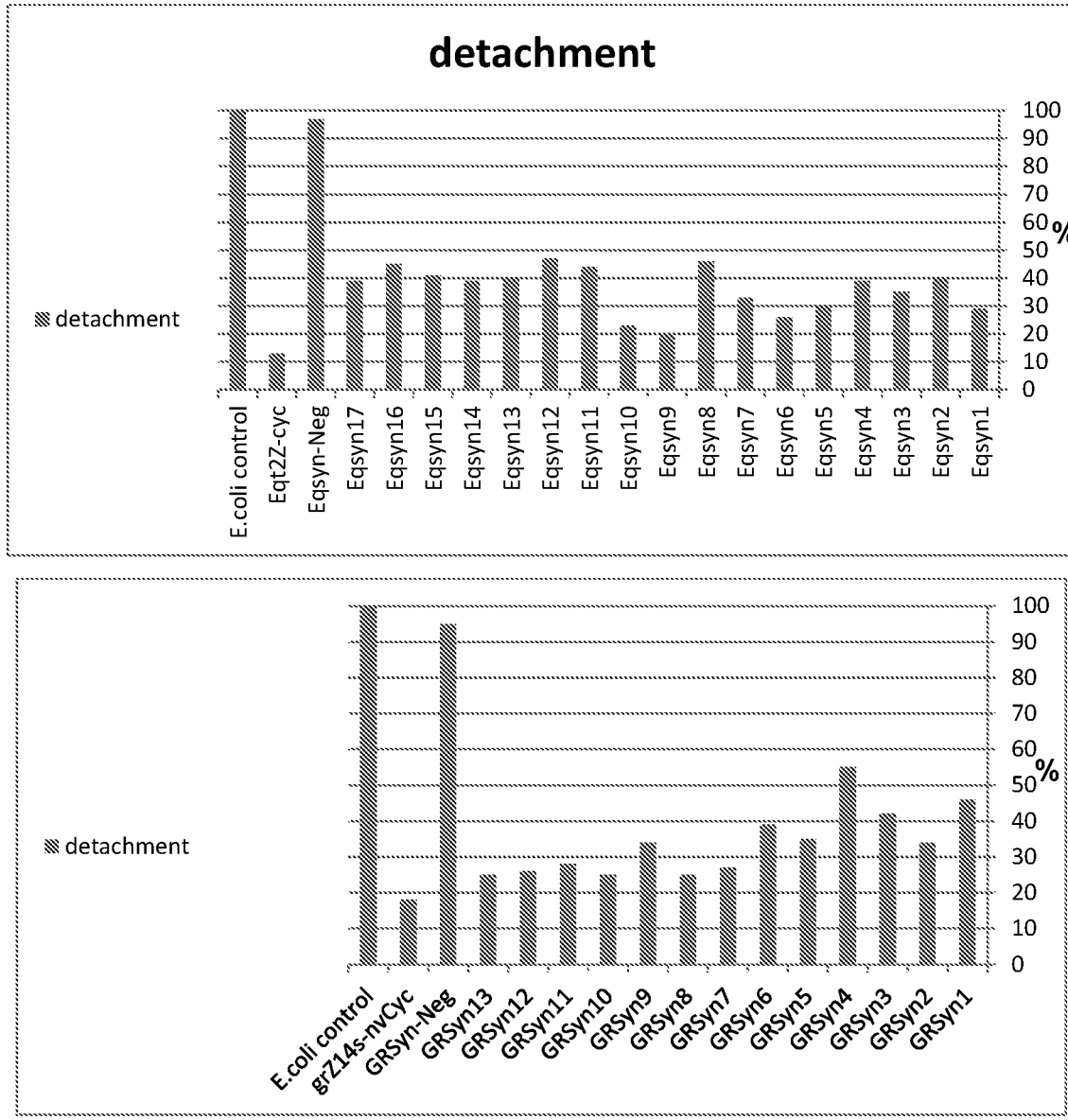
FIG. 16B shows the detachment of *Escherichia coli* adherence by various peptides.

The results are presented in FIG. 12. As the demonstrates, the number of live bacteria was much lower in wells with grZ14s-nvCyc and Kanamycin than in wells with Kanamycin alone, thereby demonstrating that grZ14s-nyCyc enhances the activity of Kanamycin.

Example 13

Preventing Adhesion and Detachment of Microorganisms with Various Peptides

The peptides depicted in Table 1 (each with a cysteine attached to the N- and C-terminus of the peptides) were synthesized using solid-phase methods and were purified to 90% (Peptron, Inc.; Taejeon, South Korea). The peptides were dissolved in 20 µl dimethyl sulfoxide and diluted in double distilled water to a concentration of 10 mg/ml. Additional dilutions were performed in phosphate buffered saline (PBS).

The ability of these peptides to prevent microbial adhesion to a surface or detach microbial adhesion from a surface were measured against the following microbial strains: *Pseudomonas aeruginoas* (ATCC27853), *Staphylococcus aureus* (ATCC25923), *Candida albicans* (ATCC14053) and *Acinetobacter baumannii* (clinical isolate). Specifically, peptides diluted to concentrations of 100 ng/ml were incubated with the foregoing microbes for 24 hours.

Biofilms of the foregoing microorganisms were grown in a 96-well found-bottom polystyrene plate. Specifically, 180 µl of overnight cultures were added to the wells with 20 µl of each peptide diluted in PBS, either simultaneously to measure prevention or after a period of time to measure detachment from 4 hours up to 24 hours post incubation. After 24 hours of incubation at 37° C., each well was washed with water and stained with 250 µl of crystal violet solution. The crystal violet solution was then removed by thoroughly washing the wells with water. To quantify the number of bacteria cells attached to the wells, the crystal violet was solubilized in 250 µl of 1% sodium dodecyl sulfate and the absorbance was measured at 595 nm. As Table 1 demonstrates, the peptides decreased the amount of microbial attachment to the wells (Table 1: "Biofilm prevention") and promoted microbial detachment (Table 1: "Detachment), thereby preventing the formation of biofilm by the microorganisms and causing them to detach where they have already adhered to a surface.

TABLE 1

Biofilm prevention and detachment by various peptides

| | Biofilm prevention (%) | Detachment (%) (100 ng/ml) |
|---|---|---|
| Peptide: SelagZ-cyc CSVPFDYNLYSNWC (SEQ ID NO: 112) | | |
| *Pseudomonas aeruginosa* ATCC27853 | 88% (100 ng/ml) | 67% |

TABLE 1-continued

Biofilm prevention and detachment by various peptides

| | Biofilm prevention (%) | Detachment (%) (100 ng/ml) |
|---|---|---|
| *Staphylococcus aureus* ATCC25923 | 88% (100 ng/ml) | 35% |
| *Candida albicans* ATCC14053 | 80% (10 ng/ml) | NA |
| *Acinetobacter baumannii* | 80% (100 ng/ml) | 50% |
| Peptide: PhyscoZ-cyc CSVPFDYNLYSNWC (SEQ ID NO: 112) | | |
| *Pseudomonas aeruginosa* ATCC27853 | 95% (100 ng/ml) | 75% |
| *Staphylococcus aureus* ATCC25923 | 65% (100 ng/ml) | 70% |
| *Candida albicans* ATCC14053 | 62% (10 ng/ml) | NA |
| *Acinetobacter baumannii* | NA | 50% |
| Peptide: EchoZ-cyc CSAPYNFNFYSNWC (SEQ ID NO: 113) | | |
| *Pseudomonas aeruginosa* ATCC27853 | 90% (100 ng/ml) | 65% |
| *Staphylococcus aureus* ATCC25923 | 85% (100 ng/ml) | 35% |
| *Candida albicans* ATCC14053 | 80% (10 ng/ml) | NA |
| *Acinetobacter baumannii* | 80% (100 ng/ml) | 60% |
| Peptide: XenoZ-S-cyc CSRYSSFDYDWYNVC (SEQ ID NO: 114) | | |
| *Pseudomonas aeruginosa* ATCC27853 | 57% (10 ng/ml) | 30% |
| *Staphylococcus aureus* ATCC25923 | 65% (100 ng/ml) | NA |
| *Candida albicans* ATCC14053 | 75% (100 ng/ml) | 50% |
| *Acinetobacter baumannii* | 95% (100 ng/ml) | 49% |
| Peptide: CionaZ-S-cyc CSELSSFNFDWYNVC (SEQ ID NO: 115) | | |
| *Pseudomonas aeruginosa* ATCC27853 | 75% (100 ng/ml) | 78% |
| *Staphylococcus aureus* ATCC25923 | 90% (100 ng/ml) | NA |
| *Candida albicans* ATCC14053 | 68% (100 ng/ml) | 42% |
| *Acinetobacter baumannii* | 52% (100 ng/ml) | 80% |
| Peptide: CanisZ-cyc CNVHSFDYDWYNVC (SEQ ID NO: 116) | | |
| *Pseudomonas aeruginosa* ATCC27853 | 95% (100 ng/ml) | 72% |
| *Staphylococcus aureus* ATCC25923 | 75% (100 ng/ml) | NA |
| *Candida albicans* ATCC14053 | 80% (100 ng/ml) | 45% |
| *Acinetobacter baumannii* | 60% (10 ng/ml) | 73% |
| Peptide: NilotiZ-cyc CRVESFNYDWYNVC (SEQ ID NO: 117) | | |
| *Pseudomonas aeruginosa* ATCC27853 | 90% (100 ng/ml) | 40% |
| *Staphylococcus aureus* ATCC25923 | 63% (100 ng/ml) | 65% |
| *Candida albicans* ATCC14053 | 30% (100 ng/ml) | 65% |
| *Acinetobacter baumannii* | 87% (100 ng/ml) | NA |
| Peptide: SalmoZ-cyc CRVESFDFDWYNIC (SEQ ID NO: 118) | | |
| *Pseudomonas aeruginosa* ATCC27853 | 90% (10 ng/ml) | 80% |
| *Staphylococcus aureus* ATCC25923 | 80% (100 ng/ml) | 75% |
| *Candida albicans* ATCC14053 | 55% (100 ng/ml) | 73% |
| *Acinetobacter baumannii* | 95% (100 ng/ml) | NA |
| Peptide: TetraoZ-cyc CRINSFDYDWYNVC (SEQ ID NO: 119) | | |
| *Pseudomonas aeruginosa* ATCC27853 | 45% (100 ng/ml) | NA |
| *Staphylococcus aureus* ATCC25923 | 52% (100 ng/ml) | 43% |
| *Candida albicans* ATCC14053 | 25% (100 ng/ml) | 55% |
| *Acinetobacter baumannii* | 70% (10 ng/ml) | NA |
| Peptide: AnoliZ-cyc CTVNSFDYDWYNVC (SEQ ID NO: 120) | | |
| *Pseudomonas aeruginosa* ATCC27853 | 95% (100 ng/ml) | 90% |
| *Staphylococcus aureus* ATCC25923 | 75% (100 ng/ml) | 72% |
| *Candida albicans* ATCC14053 | 55% (100 ng/ml) | 72% |
| *Acinetobacter baumannii* | 92% (10 ng/ml) | NA |
| Peptide: MeleagZ-cyc CKVNSFDYDWYNVC (SEQ ID NO: 121) | | |
| *Pseudomonas aeruginosa* ATCC27853 | 82% (100 ng/ml) | 65% |
| *Staphylococcus aureus* ATCC25923 | 73% (100 ng/ml) | 80% |
| *Candida albicans* ATCC14053 | 30% (100 ng/ml) | 62% |
| *Acinetobacter baumannii* | 95% (100 ng/ml) | NA |
| Peptide: CapraZ-cyc CTVHSFDYDWYNVC (SEQ ID NO: 122) | | |
| *Pseudomonas aeruginosa* ATCC27853 | 68% (100 ng/ml) | 65% |
| *Staphylococcus aureus* ATCC25923 | 42% (100 ng/ml) | 55% |
| *Candida albicans* ATCC14053 | 25% (100 ng/ml) | 60% |
| *Acinetobacter baumannii* | 90% (100 ng/ml) | NA |

Peptides listed in Table 2, synthesized in the same manner described above for Table 1, have a cysteine that was added to the N- and C-terminal ends of the peptides, as represented by the "C" at either end of the peptides. These peptides also are cyclized, as indicated by the "(C—C)" term at the end of each peptide. EqSyn-Neg- and GRSyn-Neg were added as negative controls.

TABLE 2

Various peptides

| No | Peptide ID | Sequence (SEQ ID NOS 123-141, respectively, in order of appearance) | No | Peptide ID | Sequence (SEQ ID NOS 142-156, respectively, in order of appearance) |
|---|---|---|---|---|---|
| 1 | EqSyn 1 | CNIPFNFSLNKERC (C-C) | 20 | GRSyn 1 | CSVHSWDYDWYNVC (C-C) |
| 2 | EqSyn 2 | CSVPYQYNWYSNWC (C-C) | 21 | GRSyn 2 | CSVHSYDFDWYNVC (C-C) |
| 3 | EqSyn 3 | CSVPWEYNFYSNWC (C-C) | 22 | GRSyn 3 | CTLQAFNYEWYQLC (C-C) |
| 4 | EqSyn 4 | CRIPYDRGMIVNVC (C-C) | 23 | GRSyn 4 | CKYETFEYGWYNIC (C-C) |
| 5 | EqSyn 5 | CKVPYDWDSVINLC (C-C) | 24 | GRSyn 5 | CHGDSFQYEWYNLC (C-C) |
| 6 | EqSyn 6 | CQLPYDVHTYNDWC (C-C) | 25 | GRSyn 6 | CSVHSFDWDWYNVC (C-C) |
| 7 | EqSyn 7 | CLAPYDHNRYTQWC (C-C) | 26 | GRSyn 7 | CSVHSFDYDYYNVC (C-C) |
| 8 | EqSyn 8 | CSNPYDLEAYENWC (C-C) | 27 | GRSyn 8 | CSVHSFDYDFYNVC (C-C) |
| 9 | EqSyn 9 | CSVPYDYQGYRNIC (C-C) | 28 | GRSyn 9 | CSVHSFDYDWFNVC (C-C) |
| 10 | EqSyn 10 | CSVPYDYNVYLNKC (C-C) | 29 | GRSyn 10 | CSVHSFDYDWWNVC (C-C) |
| 11 | EqSyn 11 | CIQPYDKNYFQNFC (C-C) | 30 | GRSyn 11 | CIFNPFDYDWYNVC (C-C) |
| 12 | EqSyn 12 | CVVPYDINIKDNWC (C-C) | 31 | GRSyn 12 | CQWHSFDYDWYNVC (C-C) |
| 13 | EqSyn 13 | CSVPYDYNPYSNWC (C-C) | 32 | GRSyn 13 | CDVHPFDYDWYNVC (C-C) |
| 14 | EqSyn 14 | CSVPYDYNKLKNWC (C-C) | 33 | GRSyn-Neg | CSVHSGDYDGGNVC (C-C) |
| 15 | EqSyn 15 | CSVPYDYNWRSSWC (C-C) | 34 | grZ14s-nvCyc | CSVHSFDYDWYNVC (C-C) |
| 16 | EqSyn 16 | CSVPYDYNWWSAWC (C-C) | | | |
| 17 | EqSyn 17 | CSVPYDYNWQSNWC (C-C) | | | |
| 18 | EqSyn-Neg | CSVGYDYNWYSNWC (C-C) | | | |
| 19 | Eqt2Z-cyc | CSVPYDYNWYSNWC (C-C) | | | |

The ability of these peptides to (1) prevent microbial adhesion to a surface and to (2) detach microbes already adhered to a surface were measured against the following microbial strains: *Pseudomonas aeruginoas* (ATCC27853), *Staphylococcus aureus* (ATCC25923), *Candida albicans* (ATCC14053) and/or *Escherichia coli*. The resulting percentage of prevention or detachment, relative to control wells in which the microbes was allowed to culture in the absence of peptides, are indicated in FIGS. 13 to 16. The figures demonstrate that these peptides are able to prevent microbial adhesion to a surface and detach microbes already adhered to a surface.

Example 14

Figure 17:
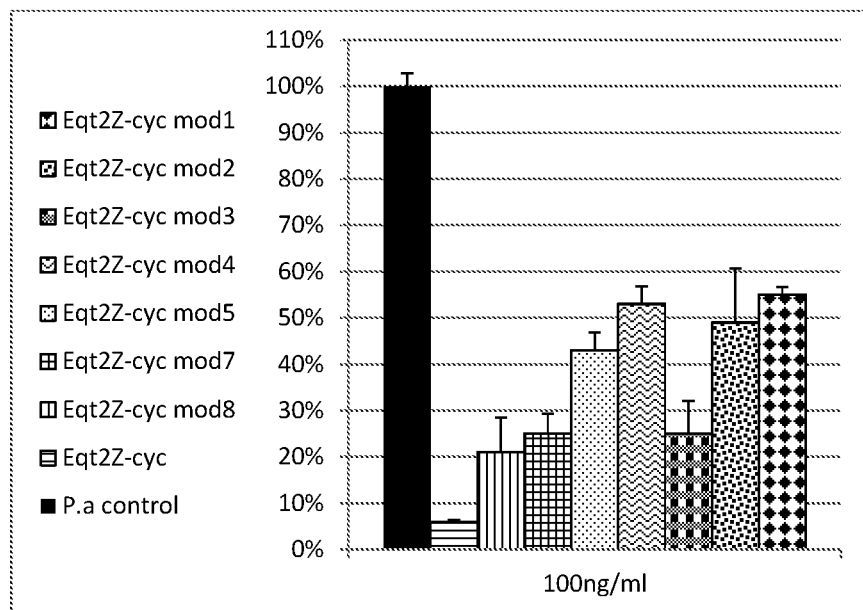
FIG. 17 shows the prevention of adhesion of *Pseudomonas aeruginoas* by various modifications of Eqt2Z-Cyc.
Figure 18:
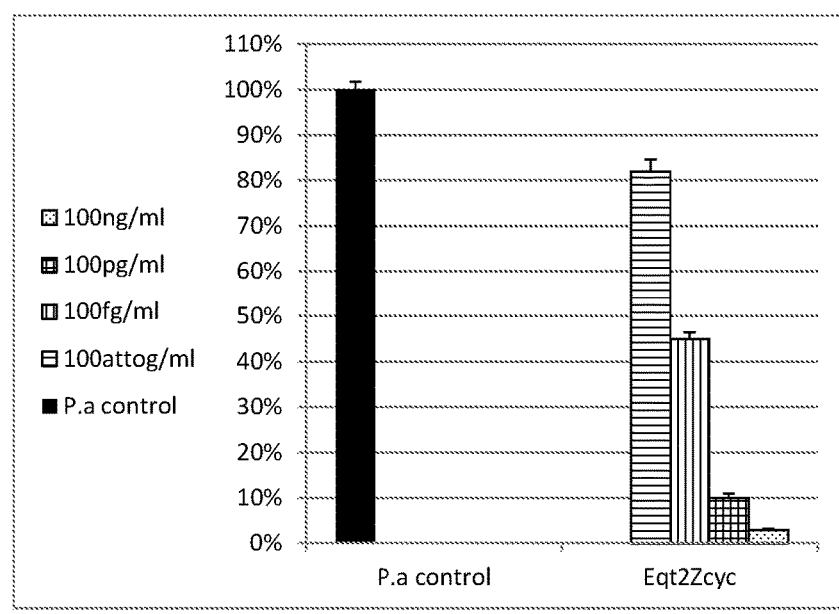
FIG. 18 shows Congo Red staining of Eqt2Z-Cyc incubated with *Pseudomonas aeruginosa*.
Figure 19:
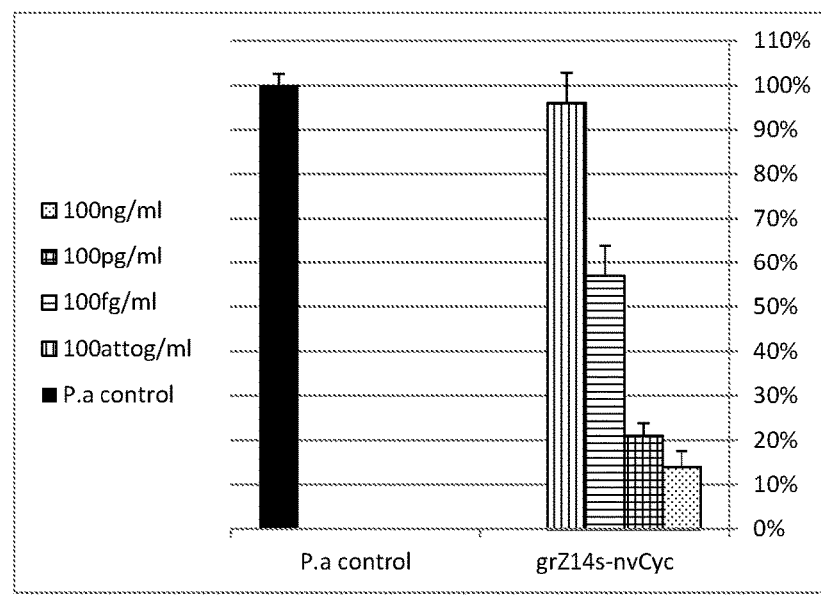
FIG. 19 shows Congo Red staining of grZ14s-nyCyc incubated with *Pseudomonas aeruginosa*.
Figure 20:
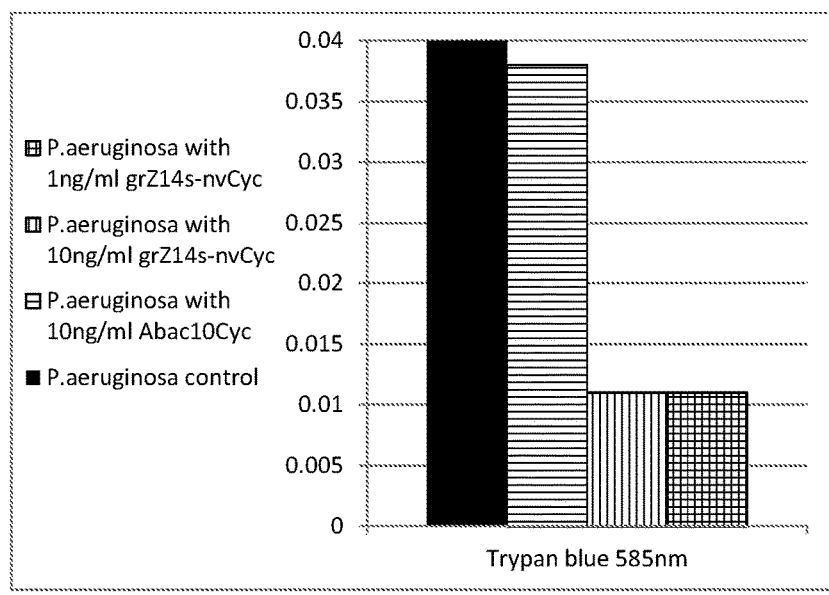
FIG. 20 shows Trypan Blue staining of grZ14s-nyCyc incubated with *Pseudomonas aeruginosa*
Figure 21:
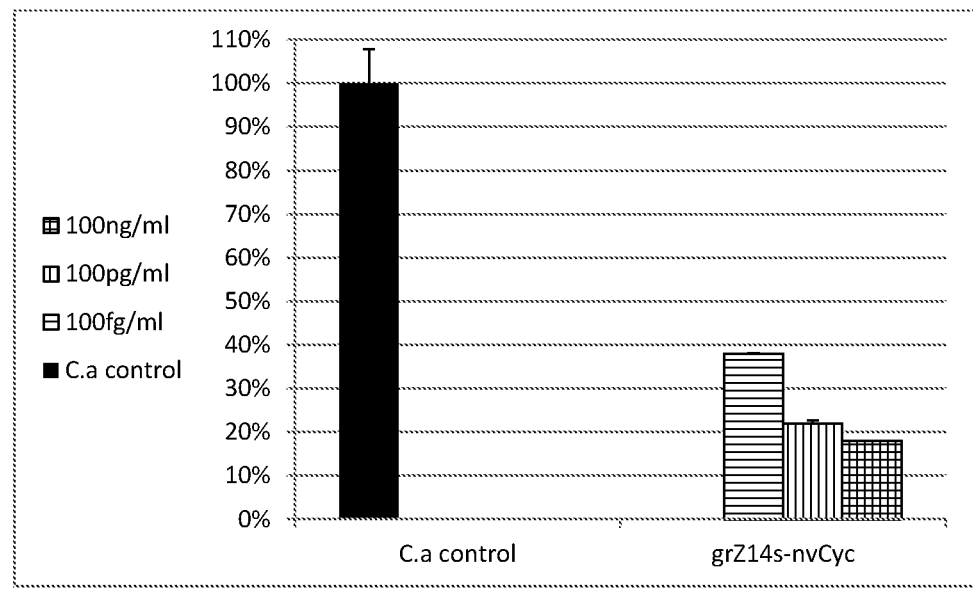
FIG. 21 shows Congo Red staining of grZ14s-nyCyc incubated with *Candida albicans*.
Figure 22:
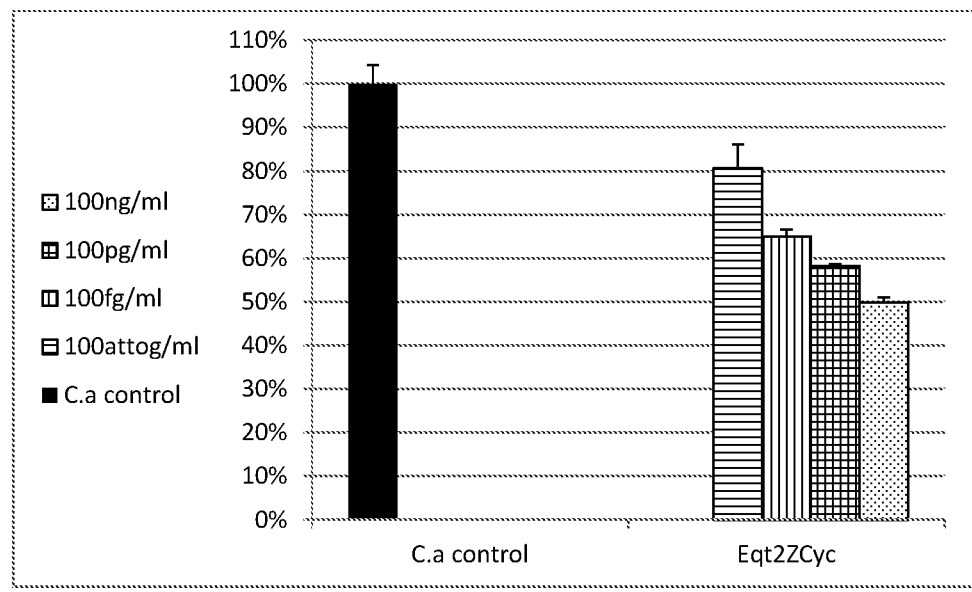
FIG. 22 shows Congo Red staining of Eqt2Z-Cyc incubated with *Candida albicans*.
Figure 23:
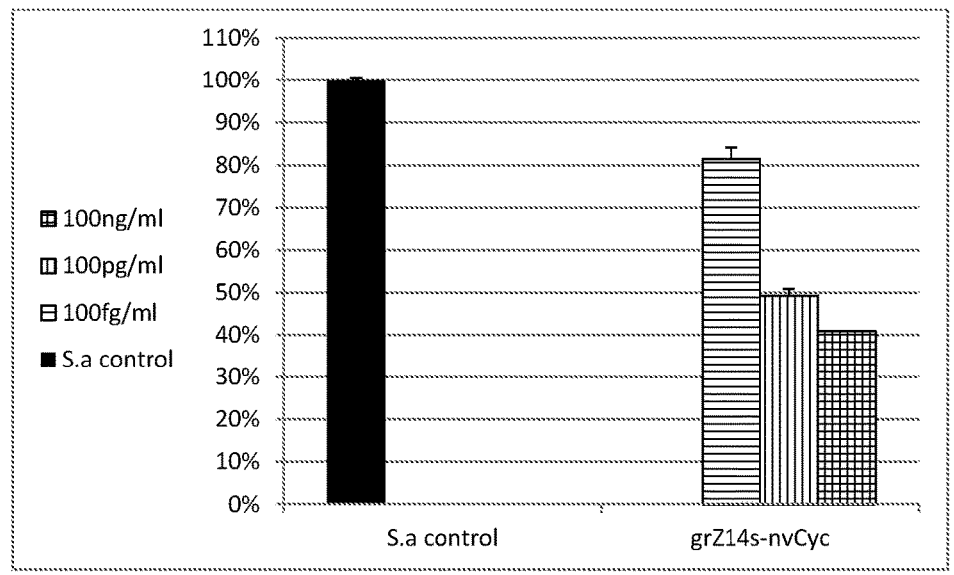
FIG. 23 shows Congo Red staining of grZ14s-nyCyc incubated with *Staphylococcus aureus*.

Preventing Adhesion of *Pseudomonas aeruginoas* with Peptides Modified from Eqt2Z-cyc The Eqt2Z-cyc peptide was modified by inserting synthetic amino acid analogs in different positions in the natural sequence. Table 3 depicts the modifications performed on Eqt2Z-cyc. The modified peptides were incubated with *Pseudomonas aeruginoas*. A biofilm was created by culturing the microorganism for 24 hours in a well at 37° C., modified Eqt2Z-cyc-mod peptide was subsequently added to the well and allowed to incubate for 24 hours. FIG. 17 depicts the results of the incubation, in which the peptides prevented adhesion of the microorganism when compared with incubation of the microorganism without any peptide.

TABLE 3

Modifications of Eqt2Z-cyc

| | |
|---|---|
| Eqt2ZCyc-mod1 | (D-form Cys)-SVPYDYNWYSNWC (C-C) |
| Eqt2ZCyc-mod2 | CSVPYDYNWYSNW-(D-form Cys) (C-C) |
| Eqt2ZCyc-mod3 | (D-form Cys)-SVPYDYNWYSNW-(D-form Cys) (C-C) |
| Eqt2ZCyc-mod4 | homoCys-SVPYDYNWYSNWC (C-C) (SEQ ID NO: 157) |
| Eqt2ZCyc-mod5 | CSVPYDYNWYSNW-homoCys (C-C) (SEQ ID NO: 158) |
| Eqt2ZCyc-mod7 | CS-(D-form V)-PYDYNWYSNWC (C-C) |
| Eqt2ZCyc-mod8 | CSV-(D-form P)-YDYNWYSNWC (C-C) |

Example 15

Peptides Contribute to Detachment of Microorganisms by Affecting Polysaccharide Matrix Production In one embodiment, peptides can cause microorganisms to detach from a surface by affecting the microorganisms' production of polysaccharide matrix. The effect of Eqt2Z-Cyc and grZ14s-nvCYC on the polysaccharide matrix production of *Pseudomonas aeruginoas, Candida albicans* and *Staphylococcus aureus* were evaluated by measuring Congo Red and/or Trypan Blue after the peptides were incubated with the microorganisms. Congo Red and Trypan Blue are dyes that bind to the polysaccharide matrix via exopolysaccharide fibrils. A reduction in absorbance of these dyes corresponds with a reduction in polysaccharide matrix production.

Specifically, Congo Red and Trypan blue binding assays were performed by growing *Pseudomonas aeruginoas, Staphylococcus aureus* and *Candida albicans* in specific growth media (LB, TSB+0.25% glucose, RPMI 1640, respectively) simultaneously with the peptides until they reached a density of $OD_{600nm}$=0.25. The cells were then pelleted, the supernant removed and the cells were resuspended in TMP buffer (contains 10.0 mM Tris/HCl (pH 8.0), 1 mM$KH_2PO_4$ and 8.0 MM $MgSO_4$) to a density of $OD_{600nm}$=0.25. Aliquots of the cell suspensions were mixed with stock solutions of Congo Red (150 μg $ml^{-1}$) and Trypan Blue (100 μg $ml^{-1}$). TPM buffer was added to the cell/dye mixtures to give final concentrations of $2.5 \times 10^8$ cells $ml^{-1}$ and either 15 μg Congo Red $ml^{-1}$ or 10 μg Trypan Blue $ml^{-1}$. Cell-free samples containing TPM buffer and 15 μg Congo Red $ml^{-1}$ or 10 μg Trypan Blue $ml^{-1}$ were used as controls. All samples were vortexed briefly and incubated in a 25° C. dark room for 30 min. Following the incubation, the cells were pelleted, and the supernatants were transferred to cuvettes. The absorbance of each supernatant sample was measured at 490 nm to detect Congo Red or at 585 nm to detect Trypan Blue, and these values were compared to the absorbance of the appropriate control sample. Each test sample and control sample was analysed three times.

The results are depicted in FIGS. 18-23. As the figures demonstrate, both peptides contributed to a reduced polysaccharide matrix production in each of the microorganisms, evident by the reduced Congo Red and Trypan Blue absorbance coming from cells incubated with the peptides as compared to cells that were not incubated with the peptides.

The invention claimed is:

1. A surface coated with a composition comprising a peptide comprising the amino acid sequence $X^1$-$X^2$-$X^3$-$X^4$-$X^5$-$X^6$-$X^7$-$X^8$-$X^9$-$X^{10}$-$X^{11}$-$X^{12}$, wherein:

(i) $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, F—, R, W, V, H, L, K or I; $X^7$ is N, S, G, D, H, E, Q or I; $X^8$ is W, L, F, M, S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E; or (ii) $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L; wherein the amino acid sequence does not comprise YDYNWY (SEQ ID NO: 49), YDYNLY (SEQ ID NO: 50), FDYNFY (SEQ ID NO: 51), FDYNLY (SEQ ID NO: 52), WDYNLY (SEQ ID NO: 53), FDYNWY (SEQ ID NO: 54), YDWNLY (SEQ ID NO: 55), YDWHLY (SEQ ID NO: 56), FDYDWY (SEQ ID NO: 46), or FNFDWY (SEQ ID NO: 48), wherein the peptide is up to 50 amino acids in length, and wherein said surface is a medical device; a household article; an article involved in water purification, water storage, or water delivery; or an article involved in food processing.

2. The surface of claim 1, wherein the medical device is selected from the group consisting of artificial blood vessels, catheters and other devices for the removal or delivery of fluids to patients, artificial hearts, artificial kidneys, orthopedic pins, prosthetic joints, plates, urinary devices, ventricular or arterio-venous shunts, prostheses, breast implants, penile prostheses, vascular grafting prostheses, aneurysm repair devices, mechanical heart valves, artificial joints, artificial larynxes, otological implants, anastomotic devices, vascular catheter ports, vascular stents, clamps, embolic devices, wound drain tubes, ocular lenses, dental implants, hydrocephalus shunts, pacemakers and implantable defibrillators, needleless connectors, and voice prostheses.

3. The surface of claim 2, wherein the catheter is selected from the group consisting of urological tubes, biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, and peritoneal catheters.

4. The surface of claim 2, wherein the medical device is an ocular lens.

5. The surface of claim 1, wherein the household article is selected from the group consisting of food processing equipment for home use, materials for infant care, tampons, soap, detergents, health and skincare products, household cleaners and toilet bowls.

6. The surface of claim 1, wherein the surface is immersed in water.

7. The surface of claim 1, wherein the amino acid sequence is selected from the group consisting of SVHSWDYDWYNV (SEQ ID NO: 33), SVHSYDFDWYNV (SEQ ID NO: 34), TLQAFNYEWYQL (SEQ ID NO: 35), KYETFEYGWYNI (SEQ ID NO: 36), HGDSFQYEWYNL (SEQ ID NO: 37), SVHSFDWDWYNV (SEQ ID NO: 38), SVHSFDYDYYNV (SEQ ID NO: 39), SVHSFDYDFYNV (SEQ ID NO: 40), SVHSFDYDWFNV (SEQ ID NO: 41), and SVHSFDYDWWNV (SEQ ID NO: 42).

8. The surface of claim 1, wherein the peptide is cyclized.

9. A medical device comprising a polymeric matrix into which a composition comprising a peptide is incorporated, wherein the peptide comprises:

the amino acid sequence $X^1$-$X^2$-$X^3$-$X^4$-$X^5$-$X^6$-$X^7$-$X^8$-$X^9$-$X^{10}$-$X^{11}$-$X^{12}$, wherein (i) $X^1$ is S, N, I, V, R, K, Q or L; $X^2$ is V, I, A, N, L or Q; $X^3$ is P; $X^4$ is Y, F or W; $X^5$ is D, N, Q or E; $X^6$ is Y, —F, R, W, V, H, L, K or I; $X^7$ is N, S, G, D, H, E, Q or I; $X^8$ is W, L, F, M, S, T, R, A, G, V, P, Y, I or K; $X^9$ is Y, N, F, K, L, R, I, V, W or Q; $X^{10}$ is S, K, N, T, E, R, L, Q, I, V, D, or K; $X^{11}$ is N, E, D, Q, S, A or I; and $X^{12}$ is W, R, V, L, I, K, F or E or (ii) $X^1$ is S, N, T, K, R, H, E, I, Q or D; $X^2$ is V, I, L, Y, G, F or W; $X^3$ is H, N, Q, E, D or S; $X^4$ is S, P, A or T; $X^5$ is F, W or Y; $X^6$ is D, N, E or Q; $X^7$ is Y, F or W; $X^8$ is D, G or E; $X^9$ is W, F or Y; $X^{10}$ is Y, F or W; $X^{11}$ is N or Q; and $X^{12}$ is V, I or L; wherein the amino acid sequence does not comprise YDYNWY (SEQ ID NO: 49), YDYNLY (SEQ ID NO: 50), FDYNFY (SEQ ID NO: 51), FDYNLY (SEQ ID NO: 52), WDYNLY (SEQ ID NO: 53), FDYNWY (SEQ ID NO: 54), YDWNLY (SEQ ID NO: 55), YDWHLY (SEQ ID NO: 56), FDYDWY (SEQ ID NO: 46), or FNFDWY (SEQ ID NO: 48), and wherein the peptide is up to 50 amino acids in length.

10. The medical device of claim 9, wherein the medical device is selected from the group consisting of artificial blood vessels, catheters and other devices for the removal or delivery of fluids to patients, artificial hearts, artificial kidneys, orthopedic pins, prosthetic joints, plates, urinary devices, ventricular or arterio-venous shunts, prostheses, breast implants, penile prostheses, vascular grafting prostheses, aneurysm repair devices, mechanical heart valves, artificial joints, artificial larynxes, otological implants, anastomotic devices, vascular catheter ports, vascular stents, clamps, embolic devices, wound drain tubes, ocular lenses, dental implants, hydrocephalus shunts, pacemakers and implantable defibrillators, needleless connectors, and voice prostheses.

11. The medical device of claim 10, wherein the catheter is selected from the group consisting of urological tubes, biliary tubes, endotracheal tubes, peripherally-insertable central venous catheters, dialysis catheters, long term tunneled central venous catheters, peripheral venous catheters, short term central venous catheters, arterial catheters, pulmonary catheters, Swan-Ganz catheters, urinary catheters, and peritoneal catheters.

12. The medical device of claim 9, wherein the medical device is an ocular lens.

13. The medical device of claim 9, wherein the amino acid sequence is selected from the group consisting of SVHSWDYDWYNV (SEQ ID NO: 33), SVHSYDFDWYNV (SEQ ID NO: 34), TLQAFNYEWYQL (SEQ ID NO: 35), KYETFEYGWYNI (SEQ ID NO: 36), HGDSFQYEWYNL (SEQ ID NO: 37), SVHSFDWDWYNV (SEQ ID NO: 38), SVHSFDYDYYNV (SEQ ID NO: 39), SVHSFDYDFYNV (SEQ ID NO: 40), SVHSFDYDWFNV (SEQ ID NO: 41), and SVHSFDYDWWNV (SEQ ID NO: 42).

14. The medical device of claim 9, wherein the peptide is cyclized.

* * * * *